United States Patent
Thorne et al.

(10) Patent No.: US 12,403,165 B2
(45) Date of Patent: Sep. 2, 2025

(54) ONCOLYTIC IMMUNOTHERAPY BY TUMOR MICRO-ENVIRONMENT REMODELING

(71) Applicant: KaliVir Immunotherapeutics, Inc., Pittsburgh, PA (US)

(72) Inventors: Stephen Howard Thorne, Pittsburgh, PA (US); Mingrui Zhang, Pittsburgh, PA (US); Daniel J. Byrd, Pittsburgh, PA (US)

(73) Assignee: KaliVir Immunotherapeutcs, Inc., Pittsburgh, PA (US)

( * ) Notice: Subject to any disclaimer, the term of this patent is extended or adjusted under 35 U.S.C. 154(b) by 0 days.

(21) Appl. No.: 18/105,374

(22) Filed: Feb. 3, 2023

(65) Prior Publication Data

US 2023/0256041 A1    Aug. 17, 2023

Related U.S. Application Data

(63) Continuation of application No. PCT/US2021/059887, filed on Nov. 18, 2021.

(60) Provisional application No. 63/116,004, filed on Nov. 19, 2020.

(51) Int. Cl.
| | | |
|---|---|---|
| *A61K 35/768* | (2015.01) | |
| *A61P 35/00* | (2006.01) | |
| *C07K 14/55* | (2006.01) | |
| *C07K 14/575* | (2006.01) | |
| *C07K 14/715* | (2006.01) | |
| *C12N 15/86* | (2006.01) | |

(52) U.S. Cl.
CPC ............ *A61K 35/768* (2013.01); *A61P 35/00* (2018.01); *C07K 14/55* (2013.01); *C07K 14/5759* (2013.01); *C07K 14/7158* (2013.01); *C12N 15/86* (2013.01); *C12N 2710/24132* (2013.01); *C12N 2710/24143* (2013.01); *C12N 2710/24171* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers |
| 4,797,368 A | 1/1989 | Carter |
| 5,139,941 A | 8/1992 | Muzyczka |
| 5,530,020 A | 6/1996 | Gunawardana |
| 5,543,158 A | 8/1996 | Gref |
| 5,912,264 A | 6/1999 | Wittman |
| 6,194,388 B1 | 2/2001 | Krieg |
| 6,198,323 B1 | 3/2001 | Offord |
| 6,207,646 B1 | 3/2001 | Krieg |
| 6,352,856 B1 | 3/2002 | Falkner |
| 6,506,559 B1 | 1/2003 | Fire |
| 6,573,099 B2 | 6/2003 | Graham |
| 6,579,865 B2 | 6/2003 | Mak |
| 6,610,860 B2 | 8/2003 | Holton |
| 6,967,023 B1 | 11/2005 | Eini |
| 6,994,863 B2 | 2/2006 | Eini |
| 7,105,184 B2 | 9/2006 | Pauly |
| 7,368,122 B1 | 5/2008 | Dow |
| 8,383,774 B2 | 2/2013 | Hill |
| 8,536,380 B2 | 9/2013 | Scheffler |
| 8,940,534 B2 | 1/2015 | Sandig |
| 9,180,091 B2 | 11/2015 | Bernick |
| 9,289,382 B2 | 3/2016 | Bernick |
| 10,232,003 B2 | 3/2019 | Mulvey |
| 10,238,700 B2 | 3/2019 | Szalay |
| 10,434,136 B2 | 10/2019 | Rammensee |
| 10,640,542 B2 | 5/2020 | Tavernier |
| 10,647,963 B2 | 5/2020 | Hemminki |
| 11,529,402 B2 | 12/2022 | Hanahan |
| 11,685,904 B2 | 6/2023 | Kirn |
| 2002/0041864 A1 | 4/2002 | Fanslow, III |
| 2002/0123099 A1 | 9/2002 | Weiner |
| 2003/0180352 A1 | 9/2003 | Patel |
| 2004/0143026 A1 | 7/2004 | Shah |
| 2004/0214783 A1 | 10/2004 | Terman |
| 2004/0248787 A1 | 12/2004 | Naito |
| 2005/0031643 A1 | 2/2005 | Szalay |
| 2005/0152903 A1 | 7/2005 | Newman |
| 2006/0057553 A1 | 3/2006 | Aguilar-Cordova |

(Continued)

FOREIGN PATENT DOCUMENTS

| | | |
|---|---|---|
| CN | 101381742 A | 3/2009 |
| CN | 1754002 B | 9/2010 |

(Continued)

OTHER PUBLICATIONS

Genbank Accession No. NM_001123041.3 Human CCR2 mRNA. Earliest priority 1988. 5 pages.*

(Continued)

*Primary Examiner* — Christopher M Babic
*Assistant Examiner* — Kimberly A Aron
(74) *Attorney, Agent, or Firm* — Greenberg Traurig, LLP

(57) ABSTRACT

The disclosure relates to modified oncolytic viruses. The modified oncolytic viruses of the disclosure comprise modification in the viral genome encoding exogenous nucleic acids to enhance the oncolytic immunotherapy by remodeling the tumor microenvironment and with enhanced systemic delivery. The disclosure further relates to compositions comprising the modified oncolytic viruses, kits containing the same, and methods of using the oncolytic viruses.

27 Claims, 7 Drawing Sheets
Specification includes a Sequence Listing.

(56) References Cited

U.S. PATENT DOCUMENTS

| | | |
|---|---|---|
| 2006/0099188 A1 | 5/2006 | Tagawa |
| 2006/0099224 A1 | 5/2006 | Kirn |
| 2006/0111278 A1 | 5/2006 | Thim |
| 2007/0029054 A1 | 2/2007 | Nien |
| 2007/0041941 A1 | 2/2007 | Weiner |
| 2007/0148195 A1 | 6/2007 | Ebert |
| 2007/0178592 A1 | 8/2007 | McArthur |
| 2007/0298054 A1 | 12/2007 | Shida |
| 2009/0004723 A1 | 1/2009 | Kirn |
| 2009/0208562 A1 | 8/2009 | Morein |
| 2009/0285860 A1 | 11/2009 | Martuza |
| 2010/0016224 A1 | 1/2010 | Bowie |
| 2010/0094560 A1 | 4/2010 | Lois |
| 2010/0112001 A1 | 5/2010 | Djurup |
| 2010/0137198 A1 | 6/2010 | Eini |
| 2010/0291139 A1 | 11/2010 | Sutter |
| 2011/0053247 A1 | 3/2011 | Baker |
| 2011/0206640 A1 | 8/2011 | Bell |
| 2011/0274711 A1* | 11/2011 | Favier ............ A61P 29/00 435/254.2 |
| 2012/0114612 A1 | 5/2012 | Evans |
| 2013/0183348 A1 | 7/2013 | Taniguchi |
| 2014/0162342 A1 | 6/2014 | Kirn |
| 2015/0105276 A1 | 4/2015 | Hofmann |
| 2016/0060311 A1 | 3/2016 | Jo |
| 2016/0152678 A1 | 6/2016 | Bancel |
| 2016/0235793 A1 | 8/2016 | Thorne |
| 2017/0016028 A1 | 1/2017 | Yla-Herttuala |
| 2017/0173092 A1 | 6/2017 | Mulvey |
| 2017/0368169 A1 | 12/2017 | Loew |
| 2018/0000733 A1 | 1/2018 | Chakroborty |
| 2018/0148694 A1 | 5/2018 | Shah |
| 2018/0214538 A1 | 8/2018 | Kirn |
| 2019/0054131 A1 | 2/2019 | Deng |
| 2019/0345204 A1 | 11/2019 | Carrió |
| 2020/0009203 A1 | 1/2020 | Sobol |
| 2020/0054677 A1 | 2/2020 | Mccoll |
| 2020/0140824 A1 | 5/2020 | Fernandez Santidrian |
| 2020/0268831 A1 | 8/2020 | Tobin |
| 2020/0330534 A1 | 10/2020 | Delgoffe |
| 2020/0330596 A1 | 10/2020 | Borriello |
| 2021/0093684 A1 | 4/2021 | Thorne |
| 2022/0033784 A1 | 2/2022 | Binder |
| 2022/0125865 A1 | 4/2022 | Thorne |
| 2023/0002740 A1 | 1/2023 | Kirn |
| 2023/0201283 A1 | 6/2023 | Binder |
| 2023/0405105 A1 | 12/2023 | Bendjama |

FOREIGN PATENT DOCUMENTS

| | | | |
|---|---|---|---|
| CN | 111556757 A | 8/2020 | |
| CN | 108350434 B | 6/2022 | |
| EP | 0119621 A1 * | 9/1984 | ............ C12N 15/00 |
| EP | 185573 A | 6/1986 | |
| EP | 488528 A | 6/1992 | |
| EP | 0689454 B1 | 3/1994 | |
| EP | 2212696 B1 | 12/2013 | |
| JP | 6012986 A | 4/1985 | |
| JP | 2007244382 A | 9/2007 | |
| KR | 20140122603 A | 10/2014 | |
| WO | 9118088 A1 | 11/1991 | |
| WO | 199309239 A1 | 5/1993 | |
| WO | 199412649 A1 | 6/1994 | |
| WO | 199426914 A1 | 11/1994 | |
| WO | 199428152 A1 | 12/1994 | |
| WO | 199428938 A1 | 12/1994 | |
| WO | 199502697 A1 | 1/1995 | |
| WO | 199622378 A1 | 7/1996 | |
| WO | 1999032619 A1 | 7/1999 | |
| WO | 0102703 A1 | 3/2001 | |
| WO | 2001036646 A1 | 5/2001 | |
| WO | 2001068836 A1 | 9/2001 | |
| WO | 2003035683 A2 | 5/2003 | |
| WO | 2004018478 A2 | 3/2004 | |
| WO | 2008023077 A2 | 2/2008 | |
| WO | 2008100292 A2 | 8/2008 | |
| WO | WO-2008142479 A2 * | 11/2008 | ............ A61K 39/12 |
| WO | 2012089225 A1 | 7/2012 | |
| WO | 2013038066 A1 | 3/2013 | |
| WO | 2014048500 A1 | 4/2014 | |
| WO | 2015027163 A1 | 2/2015 | |
| WO | 2015103438 A2 | 7/2015 | |
| WO | 2016033555 A1 | 3/2016 | |
| WO | 2016061286 A1 | 4/2016 | |
| WO | 2016144564 A2 | 9/2016 | |
| WO | 2017013419 A1 | 1/2017 | |
| WO | 2017043815 A1 | 3/2017 | |
| WO | 2017112741 A1 | 6/2017 | |
| WO | 2017165464 A1 | 9/2017 | |
| WO | 2018057755 A1 | 3/2018 | |
| WO | 2018058258 A1 | 4/2018 | |
| WO | 2018091680 A1 | 5/2018 | |
| WO | 2019089755 A1 | 5/2019 | |
| WO | 2019148109 A1 | 8/2019 | |
| WO | 2019213452 A1 | 11/2019 | |
| WO | 2020033791 A1 | 2/2020 | |

OTHER PUBLICATIONS

Genbank Accession No. NM_000586.4, *Homo sapiens* Interleukin 2 (IL2), mRNA. Earliest publication date 1992, 4 pages.*

Yu et al., Visualization of tumors and metastases in live animals with bacteria and vaccinia virus encoding light-emitting proteins. Nat Biotechnol, vol. 22, p. 313-20 (2004).

Yue et al., Targeting STAT3 in cancer: how successful are we? Expert Opin. Investig. Drugs, vol. 18(1), p. 45-56 (2009).

Zamarin et al., Intratumoral modulation of the inducible co-stimulator ICOS by recombinant oncolytic virus promotes systemic anti-tumour immunity, Nature Communication, 2017; 8: p. 1-14.

Zeh H, et al., First-in-man Study of Western Reserve Strain Oncolytic Vaccinia Virus: Safety, Systemic Spread and Anti-tumor Activity. Molecular Therapy, vol. 23, No. 1, Jan. 2015.

Zhang et al., Eradication of solid human breast tumors in nude mice with an intravenously injected light-emitting oncolytic vaccinia virus. Cancer Res, vol. 67, p. 10038-46 (2007).

Zhu et al., High-throughput screening for TLR3-IFN regulatory factor 3 signaling pathway modulators identifies several antipsychotic drugs as TLR inhibitors. Journal of Immunology, vol. 184, p. 5768-76 (2010).

Zhu et al., Innate immunity against vaccinia virus is mediated by TLR2 and requires TLR-independent production of IFN-B. Blood, vol. 109, p. 619-25 (2007).

Zufferey et al., Self-Inactivating Lentivirus Vector for Safe and Efficient In Vivo Gene Delivery, J. Virol., 1998, vol. 72, p. 9873-80.

International Search Report and Written Opinion for PCT/US2018/058456, mailed Feb. 5, 2019.

International Search Report and Written Opinion for PCT/US2020/012611, mailed Apr. 20, 2020.

International Search Report and Written Opinion for PCT/US2020/056107, mailed Mar. 1, 2021.

International Search Report and Written Opinion for PCT/US2020/056130, mailed Feb. 8, 2021.

International Search Report and Written Opinion for PCT/US2021/059887, mailed Feb. 2, 2022.

International Search Report and Written Opinion for PCT/US2022/026703, mailed Oct. 5, 2022.

International Search Report and Written Opinion for PCT/US2022/033524, mailed Nov. 23, 2022.

International Search Report for PCT/US2017/042910, mailed Mar. 6, 2018.

International Search Report for PCT/US2017/052746, mailed Feb. 13, 2018.

International Search Report for PCT/US2019/015434, mailed Apr. 5, 2019.

International Search Report for PCT/US2019/062643, mailed Mar. 31, 2020.

Pearson et al., Improved Tools for Biological Sequence Comparison, Proc. Natl. Acad. Sci. USA vol. 85, p. 2444-2448, 1988.

(56) References Cited

OTHER PUBLICATIONS

Penna, et al., Cutting Edge: Differential Chemokine Production by Myeloid and Plasmacytoid Dendritic Cells, J. Immunol., vol. 69, p. 6673-6676, (2002).
Peritt, et al., Cutting Edge: Differentiation of Human NK Cells into NK1 and NK2 Subsets, J. Immunol., vol. 161, p. 5821-5824 (1998).
Perry et al., Clinical Scale Expansion of Human Pluripotent Stem Cells, Blood, vol. 106(11), (2005), Abstract Only.
Persing et al., Taking Toll: Lipid A Mimetics as Adjuvants and Immunomodulators, Trends in Microbiology, vol. 10, No. 10, S32-S37, 2002.
Pharmaceutical Preformulation and Formulation, CRC Press LLC: Boca Raton, FL, 2004).
Pipiya et al., Hypoxia reduces adenoviral replication in cancer cells by downregulation of viral protein expression, Gene Ther 2005, vol. 12(11). pp. 911-917.
Pol et al., Preclinical Evaluation of an Oncolytic Mamba Virus Vaccine in a Simian Model. 7th International Oncolytic Viruses Meeting (Quebec City, 2013).
Prestwich et al., Immune-mediated Antitumor Activity of Reovirus is Required for Therapy and is Independent of Direct Viral Oncolysis and Replication. Clin Cancer Res, vol. 15, o4374-81 (2009).
Prestwich et al., Tumor Infection by Oncolytic Reovirus Primes Adaptive Antitumor Immunity. Clinical Cancer Research : An Official Journal of the American Association for Cancer Research, vol. 14(22), p. 7358-66 (2008).
Puhlmann et al., Vaccinia is a vector for tumor-directed gene therapy: Biodistribution of a thymidine kinase-deleted mutant, Cancer Gene Ther, vol. 7, p. 676-73, 2000.
Pulido et al., Using Virally Expressed Melanoma cDNA Libraries to Identify Tumor-associated Antigens that Cure Melanoma. Nature Biotechnology, vol. 30, p. 337-43 (2012).
Putz et al., Quantification of Antibody Responses Against Multiple Antigens of the Two Infectious Forms of Vaccinia Virus Provides a Benchmark for Smallpox Vaccination. Nat Med, vol. 12, p. 1310-5 (2006).
Rakoff-Nahoum et al. Toll-like Receptors and Cancer. Nature Reviews. Cancer, vol. 9, p. 57-63 (2009).
Reading et al., Vaccinia Virus Interleukin-18-Binding Protein Promotes Virulence by Reducing Gamma Interferon Production and Natural Killer and T-cell Activity. J Virol, vol. 77, p. 9960-8 (2003).
Rehm et al., Vaccinia Virus A35R Inhibit MHC Class II Antigen Presentation, Virology, vol. 397(1), p. 176-86, 2010.
Ricca et al., Pre-existing Immunity to Oncolytic Virus Potentiates Its Immunotherapeutic Efficacy, Mol Ther 2018, vol. 26(4), pp. 1008-1019.
Rivadeneira, et al. Oncolytic Viruses Engineered to Enforce Leptin Expression Reprogram Tumor-Infiltrating T Cell Metabolism and Promote Tumor Clearance. Immunity, vol. 51, p. 548-560. 2019.
Robins et al., Comprehensive assessment of T-cell receptor β-chain diversity in αβ T cells, Blood 2009, vol. 114(19), p. 4099-107.
Rojas J, Sampath P, Hou W, Thorne SH, Defining Effective Combinations of Immune Checkpoint Blockade and Oncolytic Virotherapy. Clin. Cancer Res., (2015), PMID: 26187615.
Roman et al., Central Leptin Action Improves Skeletal Muscle AKT, AMPK, and PGC1a Activation by Hypothalamic PI3k-Dependent Mechanism, Mol Cell Endocrinol, vol. 314(1), p. 62-9, 2010.
Rommelfanger et al., Systemic Combination Virotherapy for Melanoma with Tumor Antigen-Expressing Vesicular Stomatitis Virus and Adoptive T-Cell Transfer. Cancer Research, p. 2753-4764 (2012).
Roper et al., Characterization of the Vaccinia Vrius A35R Protein and its Role in Virulence, J of Virology, vol. 80, No. 1, p. 306-313, 2006.
Rosenberg et al., Cancer Immunotherapy: Moving Beyond Current Vaccines. Nat Med, vol. 10, p. 909-15 (2004).
Russell et al., Oncolytic Viruses as Antigen-Agnostic Cancer Vaccines, Cancer Cell 2018, vol. 33(4), pp. 599-605.
Saikh, et al., Toll-Like Receptor and Cytokine Expression Patterns of CD56+ T Cells Are Similar to Natural Killer Cells in Response to Infection with Venezuelan Equine Encephalitis Virus Replicons, J. Infect. Dis., vol. 188, p. 1562-1570, 2003.
Sakamoto, et al., Characteristics of T-cell Receptor Va24JaQ T Cells, a Human Counterpart of Murine NK1+ T Cells, from Normal Subjects, J. Allergy Clin. Immunol., vol. 103, S445-S451, 1999.
Sambrook et al. (ed.), Molecular Cloning: A Laboratory Manual 2nd ed., vol. 1-3, Cold Spring Harbor Laboratory Press, Cold Spring, Harbor, N.Y., 1989.
Sampath et al., Crosstalk Between Immune Cell and Oncolytic Vaccinia Therapy Enhances Tumor Trafficking and Antitumor Effects, Molecular Ther., vol. 21, No. 3, p. 620-628, 2013.
Sampath P, et al., Arming viruses in multi-mechanistic oncolytic viral therapy: current research and future developments, with emphasis on poxviruses. Oncolytic Virotherapy, vol. 3, p. 1-9, 2013.
Sampath P, et al., Novel therapeutic strategies in human malignancy: Combining immunotherapy and oncolytic virotherapy. Oncolytic Virotherapy, vol. 4, p. 75-82, (2015).
Samuelsson et al., Survival of Lethal Poxvirus Infection in Mice Depends on TLR9, and Therapeutic Vaccination Provides Protection. J Clin Invest, vol. 118, p. 1776-84 (2008).
Santos-Alvarez et al., Human Leptin Stimulates Proliferation and Activation of Human Circulating Monocytes, Cell Immunol, vol. 194, p. 6-11, 1999.
Sasaki et al., Regulation of DNA-raised Immune Responses by Cotransfected Interferon Regulatory Factors. Journal of Virology, vol. 76, 6652-9 (2002).
Satija et al., Spatial reconstruction of single-cell gene expression, Nat Biotechnol 2015, vol. 33(5), pp. 495-502.
Sato et al., Toll/IL-1 Receptor Domain-Containing Adaptor Inducing IFN-B (TRIF) Associates . . . in the Toll-Like Receptor Signaling1, Journal of Immunology, vol. 171, p. 4304-10 (2003).
Sautes-Fridman et al., Tumor Microenvironment is Multifaceted. Cancer Metastasis Reviews, vol. 30, vol. 13-25, 2011.
Schafer et al., Vaccinia virus-mediated intra-tumoral expression of matrix metalloproteinase 9 enhances oncolysis of PC-3 xenograft tumors, BMC Cancer, 2012, vol. 12, No. 366, p. 1-9.
Scharping et al., Efficacy of PD-1 Blockade is Potentiated by Metformin-induced Reduction of Tumor Hypoxia, Cancer Immunol. Res., vol. 5, p. 9-16, 2017.
Scharping et al., The Tumor Microenvironment Represses T Cell Mitochondrial Biogenesis to Drive Intratumoral T Cell Metabolic Insufficiency and DysfunctionImmunity 2016; vol. 45(3), p. 374-388, 2016.
Schmidt, Amgen Spikes Interest in Live Virus Vaccines for Hard-to-Treat Cancers. Nature Biotechnology, vol. 29, p. 295-6 (2011).
Senzer et al., Phase II Clinical Trial of a Granulocyte-Macrophage Colony-stimulating Factor-encoding, Second-generation Oncolytic Herpesvirus in Patients with Unresectable Metastatic Melanoma. J Clin Oncol, vol. 27, p. 5763-71 (2009).
Setoguchi et al., Homeostatic Maintenance of Natural Foxp3(+) CD25(+) CD4(+) Regulatory T Cells by Interleukin (IL)-2 and Induction of Autoimmune Disease by IL-2 Neutralization. The Journal of Experimental Medicine, vol. 201, p. 723-35 (2005).
Shao L et al., (2019) IRF1 Inhibits Antitumor Immunity through the Upregulation of PD-L1 in the Tumor Cell. Cancer Immunol Res., vol. 7, Issue 8:1258-1266.
Sharma et al, The PTEN Pathway in Tregs is a Critical Driver of the Suppressive Tumor Microenvironment, Sci. Advance, p. 1-15, 2015.
Sharma et al., Primary, Adaptive, and Acquired Resistance to Cancer Immunotherapy, Cell, vol. 168(4), p. 707-23, 2017.
Sibelius et al., Role of Listeria Monocytogenes Exotoxins Listeriolysin and Phosphatidylinositol-Specific Phospholipase C in Activation of Human Neutrophils, Infection Immunity, vol. 67, p. 1125-1130, 1999.
Sidobre, et al., The T Cell Antigen Receptor Expressed by Va14i NKT Cells has a Unique Mode of Glycosphingolipid Antigen Recognition, Proc. Natl. Acad. Sci., vol. 101, p. 12254-12259, 2004.
Silva et al., Aldehyde Dehydrogenase in Combination with CD 133 Defines Angiogenic Ovarian Cancer Stem Cells that Portend Poor Patient Survival. Cancer Research, vol. 71, p. 3991-4001 (2011).
Siveen et al., Targeting the STAT3 Signaling Pathway in Cancer: Role of Synthetic and Natural Inhibitors, Biochimica et Biophysica Acta, vol. 1845, p. 136-154 (2014).

(56) References Cited

OTHER PUBLICATIONS

Kobayashi, et al., Bacterial Pathogens Modulate an Apoptosis Differentiation Program in Human Neutrophils, Proc. Natl. Acad. Sci. USA, vol. 100, p. 10948-10953, 2003.

Kochneva et al., Engineering of double recombinant vaccinia virus with enhanced oncolytic potential for solid tumor virotherapy, Oncotarget, 2016, vol. 7, No. 45, p. 74171-74188.

Kolb-Maurer et al., Listeria Monocytogenes-Infected Human Dendritic Cells: Uptake and Host Cell Response, Infection Immunity, vol. 68, p. 3680-3688, 2000.

Kowalsky et al., Superagonist IL-15Armed Oncolytic Virus Elicits Potent Antitumor Immunity and Therapy that are Enchanced with PD-1 Blockadge, Molecular Therapy, Nature Publishing Group, 2018, vol. 26, No. 10, p. 2476-2486.

La Cava et al., The Weight of Leptin in Immunity, Nat Rev Immunol, vol. 4, p. 371-379, 2004.

La-Beck et al., Erratum, 2015 Pharmacotherapy Publications, Inc.

Lalvani et al., Rapid Effector Function in CD8+ Memory T Cells, J. Exp. Med., vol. 186, p. 859-865, 1997.

Langland et al., The Role of the PKR-Inhibitory Genes, E3L and K3L, in Determining Vaccinia Virus Host Range, Virology. vol. 299(1), p. 133-41, 2002.

Lawler et al. Oncolytic Viruses in Cancer Treatment, JAMA Oncology, Jun. 1, 2017, vol. 3, No. 6, pp. 841-849.

Le et al., CDS(+) Foxp3(+) Tumor Infiltrating Lymphocytes Accumulate in the Context of an Effective Anti-tumor Response. International Journal of Cancer. Journal International du Cancer, vol. 129, p. 636-47 (2011).

Lemoine et al., Massive Expansion of Regulatory T-cells Following Interleukin 2 Treatment During a Phase 1-11 Dendritic Cell-based Immunotherapy of Metastatic Renal Cancer. International Journal of Oncology, vol. 35, No. 569-81 (2009).

Levero et al., Defective and Nondefective Adenovirus Vectors for Expressing Foreign Genes in Vitro and in Vivo, Gene, 1991, vol. 101, p. 195-202, 1991.

Li et al., CCL5-armed oncolytic virus augments CCR5-engineered NK cell infiltration and antitumor efficiency. J Immunother Cancer. 8(1):e000131, 2020, PMID: 32098828.

Li J, et al., (2011) Chemokine Expression From Oncolytic Vaccinia Virus Enhances Vaccine Therapies of Cancer. Molecular Therapy, vol. 19, No. 5, pp. 650-657, 2011.

Liu et al., The Targeted Oncolytic Poxvirus JX-594 Demonstrates Antitumoral, Antivascular, and Anti-HBV Activities in Patients with Hepatocellular Carcinoma. Mol Ther, vol. 16, p. 1637-42 (2008).

Loffreda et al., Leptin Regulates Proinflammatory Immune Responses, FASEB J, vol. 12, 57-65, 1998.

Longhi, M.P., et al., Dendritic cells require a systemic type I interferon response to mature and induce CD4+ Th1 immunity with poly IC as adjuvant. The Journal of Experimental Medicine, vol. 206, p. 1589-1602 (2009).

Lun et al., "Effects of Intravenously Administered Recombinant Vesicular Stomatitis Virus (VSV-delta-M51) on Multifocal and Invasive Gliomas", Journal of the National Cancer Institute, 2006, vol. 98, No. 21, p. 1546-1556.

Mahoney et al., Combination cancer immunotherapy and new immunomodulatory targets, Cancer Immunotherapy, Nature Reviews, Drug Discovery, vol. 14, Aug. 2015, pp. 561-584.

Mailliard et al., Alpha-type-I Polarized Dendritic Cells: A Novel Immunization Tool with Optimized CTL-inducing Activity. Cancer Res, vol. 64, p. 5934-7, (2004).

Martin-Romero et al., Human Leptin Enhances Activation and Proliferation of Human Circulating T Lymphocytes, Cell Immunol, vol. 199(1), p. 15-24, 2000.

Mccart et al., Systemic cancer therapy with a tumor-selective vaccinia virus mutant lacking thymidine kinase and vaccinia growth factor genes. Cancer Res, vol. 61, p. 8751-7 (2001).

Mcheyzer-Williams et al., Enumeration and Characterization of Memory Cells in the Th Compartment, Immunol. Rev., vol. 150, p. 5-21, 1996.

Mcintosh et al., Vaccinia Virus Glycoprotein A34R is Required for Infectivity of Extracellular Enveloped Virus. J Virol, vol. 70:, p. 272-81, 1996.

Mcmanus et al., Gene Silencing Using Micro-RNA Designed Hairpins, RNA, vol. 8, p. 842-850, (2002).

Mcmichael et al., A New Look at T Cells, J. Exp. Med., vol. 187(9), p. 1367-1371, 1998.

Meyer et al., Mapping of Deletions in the Genome of the Highly Attenuated Vaccinia Virus MVA and Their Influence on Virulence, J. of General Virology, vol. 72, p. 1031-1038, 1991.

Millipore Sigma, Benzonase endonuclease, SAFC, 2018, pp. 1-40.

Moleirinho et al., Clinical-grade Oncolytic Adenovirus Purification Using Polysorbate 20 as an Alternative for Cell Lysis, Current Gene Therapy, 2018, vol. 18, p. 366-374.

Moon EK et al., Intra-tumoral delivery of CXCL 11 via a vaccinia virus, but not by modified T cells, enhances the efficacy of adoptive T cell therapy and vaccines. Oncoimmunology, vol. 7, Issue 3, 2018.

Moss B. Poxviridae: The Viruses and Their Replication. Field's Virology (eds. D.M., K., Fields, B.N. & Howley, P.M.) Ch.84 (Lippincott-Raven, Philadelphia, 2001).

Myers and Miller, Approximate matching of regular expressions, Bulletin of Mathematical Biology, vol. 51, Issue 1, p. 5-37; (1989).

Paul et al., Tumor Gene Therapy by MVA-Mediated Expression of T-Cell-Stimulating Antibodies, Cancer Gene Ther., vol. 9, p. 470-7, 2002.

Najjar et al., Clinical Perspectives on Targeting of Myeloid Derived Suppressor Cells in the Treatment of Cancer, Frontiers in Oncology, vol. 3(49), p. 1-9, 2013.

Naldini, Nuclear Acid Delivery: Lentiviral and Retroviral Vectors, Curr. Opin. Biotechnol., vol. 9, p. 457-63, 1998.

Narang et al., Improved Phosphotriester Method for Synthesis of Gene Fragments, Meth. Enzymol., vol. 68, p. 90-99, 1979.

Needham-Vandevanter et al., Characterization of an Adduct between CC-1065 and a Defined Oligodeoxynucleotide Duplex, Nucl. Acids Res., vol. 12, p. 6159-6168, 1984.

Needleman et al., A General Method Applicable to the Search for Similarities in the Amino Acid Sequence of Two Proteins,, J. Mol. Biol., vol. 48, p. 443-453, 1970.

Nestle et al., Cancer Vaccines: The Next Generation of Tools to Monitor the Anticancer Immune Response. PLoS Med 2, e339 (2005).

Ning et al., Cancer Stem Cell Vaccination Confers Significant Antitumor Immunity. Cancer Research, vol. 72, p. 1853-64 (2012).

Nishio et al., Oncolytic Virus Expressing RANTES and IL-15 Enhances Function of CAR-Modified T Cells in Solid Tumors, Oncoimmunology, Mar. 6, 2015 (Mar. 6, 2015), vol. 4, No. 2, pp. 1-3.

O'Gorman et al., Alternate Mechanisms of Initial Pattern Recognition Drive Differential Immune Responses to Related Poxviruses. Cell Host & Microbe, vol. 8, p. 174-85 (2010).

Okada et al., Induction of CD8+ T-cell Responses Against Novel Glioma-associated Antigen Peptides and . . . Carboxymethylcellulose in Patients with Recurrent Malignant Glioma. Journal of Clinical Oncology : Official Journal of the American Society of Clinical Oncology, vol. 29, p. 330-6 (2011).

Okamura, H., et al. Cloning of a new cytokine that induces IFN-gamma production by T cells. Nature, vol. 378, p. 88-91 (1995).

O'Neill et al., Therapeutic Targeting of Toll-like Receptors for Infectious and Inflammatory Diseases and Cancer. Pharmacological Reviews, vol. 61, p. 177-97 (2009).

Orubu et al., Expression and Cellular Immunogenicity of a Transgenic Antigen Driven by Endogenous Poxviral Early Promoters at Their Authentic Loci in MVA, PLOS One 7:e40167, 2012.

Ottolino-Perry et al. Intelligent Design: Combination Therapy With Oncolytic Viruses, Molecular Therapy, Feb. 28, 2010, vol. 18, No. 2, pp. 251-263.

Parato et al., The Oncolytic Poxvirus JX-594 Selectively Replicates in and Destroys Cancer Cells Driven by Genetic Pathways Commonly Activated in Cancers, Molecular Therapy, vol. 20, No. 4, p. 749-758, 2012.

(56) References Cited

OTHER PUBLICATIONS

Park et al., Use of a Targeted Oncolytic Poxvirus, JX-594, in Patients with Refractory Primary or Metastatic Liver Cancer: A Phase I Trial. Lancet Oncol, vol. 9, p. 533-42 (2008).
Benfield et al., Vaccinia virus protein K7 is a virulence factor that alters the acute immune response to infection; Journal of General Virology, 2013, vol. 94, p. 1647-1657.
Di Pilato et al., NFκB activation by modified vaccinia virus as a novel strategy to enhance neutrophil migration and HIV-specific T-cell responses, PNAS, 2015, p. E1333-E1342.
Furusato et al., CXCR4 and Cancer, AM Fulton, Chemokine Receptors in Cancer, Cancer Drug Discovery and Development, 2009, p. 31-45.
KaliVir Poster Presentation 894; A novel oncolytic immunotherapy, VET3-TGI, overcomes TGFB1 mediated immunosuppression, augments type-1 immune response, and displays potent therapeutic activity in multiple mouse tumor models; Published Nov. 7, 2022.
Kleinpeter et al., Vectorization in an oncolytic vaccinia virus of an antibody, a Fab and a scFv against programmed cell death-1 (PD-1) allows their intratumorial delivery and an improved tumor-growth inhibition, Oncoimmunology, 2016; vol. 5, No. 10, e1220467, p. 1-14.
Lim et al., Targeting the CCL2-CCR2 signaling axis in cancer metastasis, Oncotarget, 2016, vol. 7, No. 19, p. 28697-28710.
Lin et al., Direct Priming of CD8+ T Cells Persists in the Face of Cowpox Virus Inhibitors of Antigen Presentation, Journal of Virology, 2021, vol. 95, Issue 10, e00186_21, p. 1-15.
Muthuswamy et al., A novel oncolytic immunotherapy, VET3-TGI, overcomes TGFB1 mediated immunosuppression, augments type-1 immune response, and displays potent therapeutic activity in multiple mouse tumor models, Journal for ImmunoTherapy of Cancer 2022, vol. 10, Abstract.
Ogata et al., Overexpression of PIAS3 Suppresses Cell Growth and Restores the Drug Sensitivity of Human Lung Cancer Cells in Association with PI3-K/Akt Inactivation, Neoplasia, 2006, vol. 8, No. 10, p. 817-825.
Oghumu et al., Transgenic Expression of CXCR3 on T Cells Enhances Susceptibility to Cutaneous Leishmania major Infection by Inhibiting Monocyte Maturation and Promoting Th2 Response, Infection and Immunity, 2015, vol. 83, No. 1, p. 67-76.
Pozzobon et al., CXCR4 signaling in health and disease, Immunology Letters, 2015, vol. 177, p. 6-15.
Raemdonck et al., CXCR3 ligands in disease and therapy, Cytokine & Growth Factor Reviews, 2015, vol. 26, p. 311-327.
Wang et al., An optimized HMGB1 expressed by recombinant rabies virus enhances immunogenicity through activation of dendritic cells in mice, Oncotarget, 2017, vol. 8, No. 48, p. 83539-83554.
Wu et al., Altered CXCR3 isoform expression regulates prostate cancer cell migration and invasion, Molecular Cancer, 2012, vol. 11, No. 3, p. 1-16.
Wu et al., Structures of the CXCR4 Chemokine GPCR with Small-Molecule and Cyclic Peptide Antagonists, Science, 2010, vol. 330, p. 1066-1071.
Yoshie, Chemokine receptors as therapeutic targets, Japanese Journal of Clinical Immunology, 2013, vol. 36, No. 4, pp. 189-196.
Godin-Ethier, et al., Indoleamine 2,3-dioxygenase Expression in Human Cancers: Clinical and Immunologic Perspectives. Clinical Cancer Research: An Official Journal of the American Association for Cancer Research, vol. 17, p. 6985-91 (2011).
Goldufsky et al., Oncolytic virus therapy for cancer. Oncolytic Virotherapy, 2013, vol. 2, p. 31-46.
Graham et al., Characteristics of a Human Cell Line Transformed by DNA from Human Adenovirus Type 5, J. Gen. Virol., vol. 36, p. 59-72, 1977.
Graham, Covalently Closed Circles of Human Adenovirus DNA are Infectious, EMBO J., vol. 3, p. 2917, 1984.
Green, D.R. et al., Immunogenic and Tolerogenic Cell Death. Nature Reviews, Immunology, vol. 9, p. 353-63 (2009).
Guedan et al., Hyaluronidase expression by an oncolytic adenovirus enhances its intratumoral spread and suppresses tumor growth, Molecular Therapy, 2010, vol. 18(7), p. 1275-83.
Gulley, et al., Pilot Study of Vaccination with Recombinant CEA-MUC-1-TRICOM Poxviral-based Vaccines in Patients with Metastatic Carcinoma. Clin Cancer Res, vol. 14, p. 3060-9 (2008).
Guo et al., Oncolytic Immunotherapy: Conceptual Evolution, Current Strategies, and Future Perspectives, Front. Oncol., vol. 8, p. 1-15, 2017.
Guo et al., Oncolytic Immunotherapy: Dying the Right Way is a Key to Eliciting Potent Antitumor Immunity, Frontiers in Oncology, Apr. 10, 2014 (Apr. 10, 2014), vol. 4, No. 74, pp. 1-11.
Guo et al., Rapid Generation of Multiple Loci-Engineered Marker-free Poxvirus and Characterization of a Clinical-Grade Oncolytic Vaccinia Virus, Molecular Therapy, Methods and Clinical Development, 2017, vol. 7, p. 112-122.
Guo, et al., Oncolytic Virotherapy: Molecular Targets in Tumor-Selective Replication and Carrier Cell-mediated Delivery of Oncolytic Viruses. Biochim Biophys Acta (2008).
Guo, et al., The Enhanced Tumor Selectivity of an Oncolytic Vaccinia Lacking the Host Range and Antiapoptosis Genes SPI-1 and SPI-2. Cancer Res, vol. 65, p. 9991-8 (2005).
Guy, et al., Expression of the Neu Protooncogene in the Mammary Epithelium of Transgenic Mice Induces Metastatic Disease. Proceedings of the National Academy of Sciences of the United States of America, vol. 89, p. 10578-82 (1992).
Hannon, G J., A Conserved Biological Response to Double-stranded RNA, RNA Interference, Nature, vol. 418, p. 244-251, 2002.
Hart et al., Genotypic and phenotypic assessment of hyaluronidase among type strains of a select group of staphylococcal species, International Journal of Microbiology, 2009, vol. 2009, Article 614371, p. 1-8.
Hennessy, et al, Targeting Toll-like Receptors: Emerging Therapeutics? Nature Reviews. Drug Discovery, vol. 9, p. 293-307 (2010).
Herbst et al., Predictive Correlates of Response to the Anti-PD-L1 Antibody MPDL3280A in Cancer Patients, Nature, vol. 515(7528), p. 563-567, 2014.
Higgins, et al., CLUSTAL: a package for performing multiple sequence alignment ona microcomputer, Gene, vol. 73, p. 237-244, 1988.
Higgins, et al., Fast and Sensitive Multiple Sequence Alignments on a Microcomputer, Cabios, vol. 5, No. , p. 151-153, 1989.
Hiley et al., Lister strain vaccinia virus, a potential therapeutic vector targeting hypoxic tumours, Gene Therapy, 2010, vol. 17(2), p. 281-287.
Hokey et al., Tumor Cell Loaded Type-I Polarized Dendritic Cells Induce Th1-mediated Tumor Immunity. Cancer Research, vol. 65, p. 10059-67 (2005).
Hornemann et al., Replication of Modified Vaccinia Virus Ankara . . . Inteferon Resistance Gene E3L, Journal of Virology, vol. 77, No. 15, p. 394-8407, 2003.
Hou W, et al. (2014) Oncolytic Vaccinia Virus Demonstrates Antiangiogenic Effects Mediated by Targeting of VEGF. Int J Cancer. 2014, vol. 135, p. 1238-1246.
Hsu et al., Leptin-Induced Mitochondrial Fusioni Mediates Hepatic Lipid Accumulation, Int J Obes (Lond) 2015, vol. 39(12), p. 1750-6.
Huang B, et al., Synergistic anti-tumor effects between oncolytic vaccinia virus and paclitaxel are mediated by the IFN response and HMGB1. Gene Therapy, vol. 18, p. 164-172, 2010.
Hughes et al., A rapid Orthopoxvirus purification protocol suitable for high-containment laboratories, Journal of Virological Methods, 2017, vol. 243, p. 68-73.
Hynes, et al., Analysis of a Second Bacteriophage Hyaluronidase Gene from *Streptococcus pyogenes*: Evidence for a Third Hyaluronidase Involved in Extracellular Enzymatic Activity, Infection and Immunity, 1995, vol. 63, No. 8, p. 3015-3020.
Iwasaki, et al., Enhanced CTL Responses Mediated by Plasmid DNA Immunogens Encoding Costimulatory Molecules and Cytokines. Journal of Immunology, vol. 158, p. 4591-601, 1997.
Janssens and Beyaert, Role of Toll-Like Receptors in Pathgen Recognition, Clinical Microb. Revs., vol. 16, p. 637-646, 2003.
Jhawar et al., Oncolytic Viruses—Natural Genetically Engineered Cancer Immunotherapies, Front. Oncol., vol. 7, p. 1-11, 2017.

(56) References Cited

OTHER PUBLICATIONS

Jiang et al., Toll-like Receptor 3-Mediated Activation of NF-kappaB and IRF3 Diverges at Toll-IL-I Receptor Domain-Containing Adapter Inducing IFN-beta. Proceedings of the National Academy of Sciences of the United States of America, vol. 101, p. 3533-8 (2004).
Jinushi, et al., MFG-ES-mediated Uptake of Apoptotic Cells by APCs Links the Pro-and-anti-inflammatory activities of GM-CSF. The Journal of Clinical Investigation, vol. 117, p. 1902-13 (2007).
Jones et al., Therapeutic Strategies for the Clinical Blockade of IL-6/gpl30 Signaling. The Journal of Clinical Investigation, vol. 121, p. 3375-83 (2011).
Kafri et al., A Packaging Cell Line for Lentivirus Vectors, J. Virol., vol. 73, No. 1, p. 576-584, 1999.
Kalinski et al., Regulation of Immune Responses by Prostaglandin E2. Journal of Immunology, vol. 188, p. 21-8 (2012).
Kalinski et al., T-cell Priming by Type-I and Type-2 Polarized Dendritic Cells: The Concept of a Third Signal. Immunol Today, vol. 20, 561-7 (1999).
Kalinski, P. & Okada, H. Polarized dendritic cells as cancer vaccines: directing effector-type T cells to tumors. Seminars in immunology 22, 173-82 (2010).
Kang et al., "HMGB1 in Cancer: Good, Bad, or Both?", Clinical Cancer Research, vol. 19, No. 15, May 30, 2013, pp. 4046-4057.
Karlin et al., Applications and Statistics for Multiple High-scoring Segments in Molecular Sequences, Proc. Natl. Acad. Sci. USA, vol. 90, p. 5873-5877 (1993).
Kaufman et al., Oncolytic viruses: a new class of immunotherapy drugs, Nature Reviews, Drug Discovery, 2015, vol. 14(9), p. 642-62.
Kelly et al., Real-time Intraoperative Detection of Melanoma Lymph Node Metastases using Recombinant Vaccinia Virus GL V-1 h68 in an Immunocompetent Animal Model. International Journal of Cancer. vol. 124, p. 911-8 (2009).
Kendrew et al. (eds.), The Encyclopedia of Molecular Biology, published by Blackwell Science Ltd., 1994.
Khuri et al., A Controlled Trial of Onyx-015, an EIB Gene-deleted Adenovirus, in Combination with Chemotherapy in Patients with Recurrent Head and Neck Cancer. Nature Medicine, vol. 6, p. 879-885 (2000).
Kim et al., Antibody Association with HER-2/neu-targeted Vaccine Enhances CD8 T Cell Responses in Mice Through Fe-mediated Activation of DCs. The Journal of Clinical Investigation, vol. 118, p. 1700-11 (2008).
Kim et al., Oncolytic and Immunotherapeutic Vaccinia Induces Antibody-mediated Complement-dependent Cancer Cell Lysis in Humans. Science Translational Medicine, vol. 5, 185ra63 (2013).
Kim et al., Systemic Armed Oncolytic and Immunologic Therapy for Cancer with JX-594, a Targeted Poxvirus Expressing GM-CSF. Mol Ther, vol. 14, p. 361-70 (2006).
Kirn et al., Enhancing Poxvirus Oncolytic Effects through Increased Spread and Immune Evasion. Cancer Res, vol. 68, p. 2071-5 (2008).
Kirn et al., Replication-selective Virotherapy for Cancer: Biological Principles, Risk Management and Future Directions. Nat Med, vol. 7, p. 781-7 (2001).
Kirn et al., Targeted and Armed Oncolytic Poxviruses: A Novel Multi-mechanistic Therapeutic Class for Cancer. Nat Rev Cancer, vol. 9, p. 64-71 (2009).
Kirn et at., Targeting of Interferon-beta to Produce a Specific, Multi-mechanistic Oncolytic Vaccinia Virus. PLoS Med, vol. 4, e353 (2007).
Asagoe, et al; Down-Regulation of CXCR2 Expression on Human Polymorphonuclear Leukocytes by TN F-a1. J Immunol, 1998, vol. 160, No. 9, p. 4518-4525.
Billottet et al., CXCR3, a double-edged sword in tumor progression and angiogenesis, Biochimica et Biophysica Acta, 2013, vol. 1836, p. 287-295.
Cronin et al., Bacterial-Mediated Knockdown of Tumor Resistance to an Oncolytic Virus Enhances Therapy, Mol Ther, 2014, vol. 22, No. 6, p. 1188-1197.

Dey et al., Intranasal Oncolytic Virotherapy with CXCR4-Enhanced Stem Cells Extends Survival in Mouse Model of Glioma, Stem Cell Reports, 2016, vol. 7, p. 471-482.
Malvoisin E, et al, Soluble chemokine receptor CXCR4 is present in human sera. Anal Biochem., 2011, vol. 414, No. 2, p. 202-7.
Manthey et al., "Complement component 5a (C5a)". The International Journal of Biochemistry & Cell Biology, 2009, vol. 41, No. 11, p. 2114-2117.
Pettit et al., Vaccinia Virus Transfection of Hippocampal Slice Neurons, Neuron, 1995, vol. 14, p. 685-688.
Rein, D.T., et al., Evaluation of tissue-specific promoters in carcinomas of the cervix uteri. J. Gene Med., 2004, vol. 6, p. 1281-1289.
Schonbeck U, "The CD40/CD154 receptor/ligand dyad". Cellular and Molecular Life Sciences. 2001, vol. 58, No. 1, p. 4-43.
Zhang JM, An J. Cytokines, inflammation, and pain. Int Anesthesiol Clin., 2007, vol. 45, No. 2, p. 27-37.
Zhou et al., Tumor-targeting bacteria engineered to fight cancer, Nat Rev Cancer, 2018, vol. 18, p. 727-743.
Konetschny et al., Generation of Transduction-Competent Retroviral Vectors by Infection with a Single Hybrid Vaccinia Virus, Journal of Virology, 2003, vol. 77, No. 12, p. 7017-7025.
Paolino et al., Drug delivery systems, Encyclopedia of Medical Devices and Instrumentation, 2006, p. 437-495.
Cohen et al., Impact of the Tumor Microenvironment on Tumor-Infiltrating Lymphocytes: Focus on Breast Cancer, Breast Cancer: Basic and Clinical Research, 2017, vol. 11, p. 1-12.
Deng et al., Oncolytic efficacy of thymidine kinase-deleted vaccinia virus strain Guang9. Oncotarget, 2017, vol. 8, No. 25, p. 40533-40543.
Harte et al. The poxvirus protein A52R targets Toll-like receptor signaling complexes to suppress host defense. J Exp Med. 2003, vol. 197, No. 3, p. 343-351.
Muller et al., Engineering NK Cells Modified with an EGFRvIII-specific Chimeric Antigen Receptor to Overexpress CXCR4 Improves Immunotherapy of CXCL12/SDF-1α-secreting Gliobastoma, J Immunother, 2015, vol. 38, No. 5, p. 197-210.
Sanchez-Puig et al., Susceptibility of different leukocyte cell types to Vaccinnia virus infection, Virgology Journal, 2004, vol. 1, No. 10, p. 1-7.
Schcheilkunov, Human Monkeypox and small pox viruses: genomic comparison, FEBS Letters, 2001, vol. 509, p. 66-70.
Wallace et al., The role of chemokines and their receptors in ocular disease, Progress in Retinal and Eye Research, 2004, p. 435-448.
Wendel et al., Natural Killer Cell Accumulation in Tumors is Dependent on IFNγ and CXCR3 Ligands, Cancer Res., 2008, vol. 68, No. 20, p. 8437-8445.
Zhao et al., CXCR4 over-expression and survival in cancer: A system review and meta-analysis, Oncotarget, 2014, vol. 6, No. 7, p. 5022-5044.
Zhang et al., Optimizing DC Vaccination by Combination with Oncolytic Adenovirus Coexpressiong IL-12 and GM-CSF, Molecular Therapy, Aug. 1, 2011, v19(8), p. 155-1568.
Chen, et al., Cancers take Their Toll—The Function and Regulation of Toll-like Receptors in Cancer Cells. Oncogene, vol. 27, p. 225-33 (2008).
Chen, et al., Regulating Cytokine Function Enhances Safety and Activity of Genetic Cancer Therapies. Molecular Therapy : The Journal of the American Society of Gene Therapy, vol. 21, p. 167-74 (2013).
Cheng et al., Anticancer Function of Polyinosinic-Polycytidylic Acid. Cancer Biology & Therapy, vol. 10, p. 1219-23 (2011).
Chertova et al. "Characterization and Favorable in Vivo Properties of Heterodimeric Soluble IL-15/IL-15Rα Cytokine Compared to IL-15 Monomer," Journal of Biological Chemistry, May 6, 2013, vol. 288, pp. 18093-18103.
Cho, et al., Isolation and Molecular Characterization of Cancer Stem Cells in MMTV-Wnt-1 Murine Breast Tumors. Stem Cells, vol. 26, p. 364-71, 2008.
Choi et al., From benchtop to bedside: a review of oncolytic virotherapy, Biomedicines, 2016, vol. 4(3), p. 1-20.
Coffin, R. Clinical Updates with oncolytic HSV. in 7th International Oncolytic Virus Meeting (Quebec City, 2013).

(56) References Cited

OTHER PUBLICATIONS

Colamonici et al., Vaccinia Virus B18R Gene Encodes a Type 1 Interferon-Binding Protein that Blocks Interferon a Transmembrane Signaling, J. Biol. Chem. vol. 270(27):, p. 5974-8. 1005, 1995.
Corpet et al., Multiple Sequence Alignment with Hierarchical Clustering, Nucleic Acids Research, vol. 16, p. 10881-10890, 1988.
Couedel et al., Diverse CD1d-Restricted Reactivity Patterns of Human T Cells Bearing "invariant" AV24BV11 TCR, Eur. J. Immunol., vol. 28, p. 4391-4397, 1988.
Dankort et al., BRafV600E cooperates with Pten silencing to elicit metastatic melanoma, Nat. Genet. 2009; vol. 41, No. 5, pp. 544-552.
Davies et al., The E3L and K3L vaccinia virus gene products stimulate translation through inhibition of the double-stranded RNA-dependent protein kinase by different mechanisms, J. Virol., vol. 67(3), p. 1688-92, 1993.
Dehoon et al., Open source clustering software, Bioinformatics 2004, vol. 20(9), pp. 1453-1454.
Delgoffe et al., Enhanced interaction between Hsp90 and raptor regulates mTOR signaling upon T cell activation, Mol. Immunol. 2009; vol. 46(13), p. 2694-8.
Di Pilato M, et al., Distinct Roles of Vaccinia Virus NF-κB Inhibitor Proteins A52, B15, and K7 in the Immune Response, J Virology, vol. 91, Issue 13, e00575-17, 2017.
Doe et al., Induction of HIV-1 envelope (gp120)-specific cytotoxic T lymphocyte responses in mice by recombinant CHO cell-derived gp120 is enhanced by enzymatic removal of N-linked glycans, Eur. J. Immunol., (1994), vol. 24, p. 2369-2376.
Donnenberg, et al., Rare-Event Analysis of Circulating Human Dendritic Cell Subsets and Their Presumptive Mouse Counterparts, Transplantation, vol. 72, p. 1946-1951, 2001.
Dowty and Wolff, ed, Gene Therapeutics, Methods and Applications of Direct Gene Transfer, Birkhauser, Boston, USA (1994).
Drugs and Pharmaceutical Sciences, Pharmaceutical Preformulation and Formulation, 2nd Edition, Gibson Ed., CRC Press LLC: Boca Raton, FL, 2004.
Durham et al. "Oncolytic VSV Primes Differential Responses to Immuno-oncology Therapy," Molecular Therapy, Aug. 30, 2017 (Aug. 30, 2017), vol. 25, No. 8, pp. 1917-1932.
Earl et al., Native oligomeric human immunodeficiency virus type 1 envelope glycoprotein elicits diverse monoclonal antibody reactivities, J of Virology, vol. 68, No. 5, 1994.
Earl et al., Removal of cryptic poxvirus transcription termination signals from the human immunodeficiency virus type 1 envelope gene enhances expression and immunogenicity of a recombinant vaccinia virus, J. Virol., vol. 64, p. 2448-2451, 1990.
Ehrlich, et al., Engagement of NKG2D by cognate ligand or antibody alone is insufficient to mediate costimulation of human and mouse CD8+ T cells, J. Immunol., vol. 174, p. 1922-1931, 2005.
Eisenberg, et al, Real-time Intraoperative Detection of Breast Cancer Axillary Lymph Node Metastases using a Green Fluorescent Protein-expressing Herpes Virus. Annals of surgery, vol. 243, p. 824-30; discussion 830-2 (2006).
Elbashir, S. M. et al., RNA Interference is Mediated by 21- and 22-Nucleotide RNAs, Genes & Development, vol. 15; p. 188-200, 2001.
Emoto, et al., Transient Control of Interleukin-4-Producing Natural Killer T Cells in Liver of Listeria Monocytogenes-Infected Mice by Interleukin 12, Infection Immunity, vol. 65, p. 5003-5009, 1997.
Enzler, et al., Deficiencies of GM-CSF and Interferon Gamma Link Inflammation and Cancer. The Journal of Experimental Medicine, vol. 197, p. 1213-9 (2003).
Ercolini et al., Recruitment of Latent Pools of High-avidity CDS(+) T Cells to the Antitumor Immune Response. The Journal of Experimental Medicine, vol. 201, p. 1591-602 (2005).
Erickson et al., Hepatitis C Virus-Specific CTL Responses in the Liver of Chimpanzees with Acute and Chronic Hepatitis C, J. Immunol., vol. 151. p. 4189-4199, 1993.

Errington, F., et al., Fusogenic membrane glycoprotein-mediated tumour cell fusion activates human dendritic cells for enhanced IL-12 production and T-cell priming. Gene Therapy, vol. 13, p. 138-49 (2006).
Evans et al., Enhancement of Antigen-Specific Immunity via the TLR4 Ligands MPL Adjuvant and Ribi.529, Summary of Clinical Trials, Expert Review Vaccines, vol. 2, No. 2, 2003.
Fahy et al., Vaccinia Virus Protein C16 Acts Intracellularly to Modulate the Host Response and Promote Virulence, J. Gen. Virol., vol. 89, p. 2377-2387, 2008.
Falivene et al., Improving the MVA vaccine Potential by Deleting the Viral Gene Coding for the IL-18 Binding Protein. PLoS One 7, e32220, 2012.
Falkner et al., Transient Dominant Selection of Recombinant Vaccinia Viruses, J Virol., vol. 64(6), p. 3108-3111, 1990.
Farrell et al., Cloning, nucleotide sequence determination and expression of the Staphylococcus aureus hyaluronate lyase gene, FEMS Microbiology Letters, 1995, vol. 130(1), p. 81-85.
Feoktistova, et al., cIAPs Block Ripoptosome Formation, a RIPI/caspase-8 Containing Intracellular Cell Death Complex Differentially Regulated by cFLIP Isoforrns. Molecular Cell, vol. 43, p. 449-63 (2011).
Feuerer et al., Fat Treg Cells: a Liaison Between the Immune and Metabolic Systems, Nat Med, vol. 15(8), p. 930-9, 2009.
Filipazzi et al., Identification of a New Subset of Myeloid Suppressor Cells . . . Antitumor Vaccine. Journal of Clinical Oncology : Official Journal of the American Society of Clinical Oncology, vol. 25, p. 2546-53 (2007).
Fountzilas et al., Review: Oncolytic Virotherapy, Updates and Future Directions, Oncotarget, vol. 8, p. 102617-39, 2017.
Friedman et al., Hypoxia Moderates γ134.5-Deleted Herpes Simplex Virus Oncolytic Activity in Human Glioma Xenoline Primary Cultures, Transl Oncol 2012, vol. 5(3), p. 200-7.
Fujita, et al.COX-2 Blockade Suppresses Gliomagenesis by Inhibiting Myeloid-Derived Suppressor Cells. Cancer Research, vol. 71, p. 2664-74, 2011.
Fukata et al., Role of Toll-like Receptors in Gastrointestinal Malignancies. Oncogene, vol. 27, p. 234-43 (2008).
Furtek et al., Strategies and Approaches of Targeting STAT3 for Cancer Treatment, ACS Chem. Biol., vol. 11(2), p. 308-318 (2016).
Galon J. et al., Type, Density, and Location of Immune Cells within Human Colorectal Tumors Predict Clinical Outcome. Science, vol. 313, p. 1960-4 (2006).
Garber, K., China Approves World's First Oncolytic Virus Therapy for Cancer Treatment. J Natl Cancer Inst, vol. 98, p. 298-300 (2006).
Gaston et al., Production of Bioactive Soluble Interleukin-15 in Complex with Interleukin-15 Receptor Alpha from a Conditionally-Replicating Oncolytic HSV-1, PLOS One, 2013, vol. 8, No. 11, p. e81768.
Gil et al., Targeting CXCL 12/CXCR4 Signaling with Oncolytic Virotherapy Disrupts Tumor, Vasculature and Inhibits Breast Cancer Metastases, Proceedings of the National Academy of Sciences, Mar. 13, 2013, vol. 110, No. 14, pp. 1291-1300.
Ginestier, et al. CXCR1 Blockade Selectively Targets Human Breast Cancer Stem Cells in Vitro and in Xenografts. The Journal of Clinical Investigation, vol. 120, p. 485-97 (2010).
Gmachl et al., The human sperm protein PH-20 has hyaluronidase activity; FEBS Letters, 1993, vol. 336, No. 3, p. 545-548.
Gnant et al., Tumor-specific Gene Delivery using Recombinant Vaccinia Virus in a Rabbit Model of Liver Metastases. J Natl Cancer Inst, vol. 91, p. 1744-50 (1999).
Aitken et al, "Brief Communication; A Heterologous Oncolytic Bacteria-Virus Prime-Boost Approach for Anticancer Vaccination in Mice", J Immunother, vol. 41, p. 125-129, 2018.
Borkotoky et al., The highly efficient T7 RNA polymerase: A wonder macromolecule in biological realm, Int. Journ of Biological Macromolecules, 2018, vol. 118, p. 49-50.
Chan et al., Oncolytic Pxviruses, Annu Rev Viro, 2014, vol. 1, p. 191-214.
Chen et al., Oncolytic Viruses, Advances in Virology, vol. 2012, Article 320206, 2 pages.
Czajkowsky et al., Fe-fusion proteins: new developments and future perspectives. EMBO Mol Med. 2012, vol. 4, p. 1015-1028.

(56) References Cited

OTHER PUBLICATIONS

Davanloo et al., Cloning and expression of the gene for bacteriophage T7 RNA polymerase, Proc Natl Acad Sci USA, Apr. 1984, vol. 81, p. 2035-2039.
Guo et al., Life after death: targeting high mobility group box 1 in emergent cancer therapies. Am J Cancer Res. 2013, v3(1), p. 1-20.
Hoffman, Tumor-seeking *Salmonella* amino acid auxotrophs, Current Opinion in Biotecnology, 2011, vol. 22, p. 917-923.
Jorgensen et al., Specific Contacts between the Bacteriophage T3, T7, and SP6 RNA Polymerases and Their Promoters*, Journ of Biological Chemistry, 1991, vol. 266, No. 1, p. 645-651.
Liu et al. CXCL 11-Armed oncolytic poxvirus elicits potent antitumor immunity and shows enhanced therapeutic efficacy. Oncoimmunology. 2016, vol. 5, No. 3; e1091554, 10 pages.
Lubyova et al., Kaposi's sarcoma-associated herpesvirus-encoded vIRF-3 stimulates the transcriptional activity of cellular IRF-3 and IRF-7, Journal of Biological Chemistry, 2004, vol. 279, No. 9, p. 7643-7654.
Morris et al., Cloning and expression of the bacteriophage T3 RNA polymerase gene, Gene, 1986, vol. 41, 193-200.
Sokolovski et al., Thermodynamic Protein Destabilization by GFP Tagging: A Case of Interdomain Allostery. Biophysical Journal., 2015, v109, p. 1157-1162.
Tang et al. Facilitating T Cell Infiltration in Tumor Microenvironment Overcomes Resistance to PD-L 1 Blockade. Cancer Cell, 2016, vol. 9, p. 285-296.
Thirunavukarasu et al., A Rationally Designed A34R Mutant Oncolytic Poxvirus: Improved Efficacy in Peritoneal Carcinomatosis, Mol Ther, 2013, vol. 21, No. 5, p. 1024-1033.
Ungerechts et al., Moving oncolytic viruses into the clinic: clinical-grade production, purification, and characterization of diverse oncolytic viruses. Mol Ther Methods Clin Dev. 2016, v3, art16018, p. 1-12.
Vaccinia Virus and Poxvirology, Methods and Protocols, vol. 269 Ed. By Stuart N. Isaacs (Humana Press (2004), Chapter 8, Growing Poxviruses and determining Virus Titer, Kotwal and Abrahams).
Whatcott et al., Targeting the tumor microenvironment in cancer: why hyaluronidase deserves a second look. Cancer Discov. 2011, v1(4), p. 291-296.
Yang et al., High Mobility Group Box Protein 1 (HMGB1): The Prototypical Endogenous Danger Molecule. Mol Med. 2015, v21 Suppl 1, S6-S12.
Youn et al., Nucleocytoplasmic Shuttling of HMGB1 Is Regulated by Phosphorylation That Redirects It toward Secretion1. J Immunol Dec. 1, 2006; v177, p. 7889-7897.
Albarnaz, Modulating Vaccinia Virus Immunomodulators to Improve Immunological Memory, Viruses, 2018, vol. 10, p. 1-33.
Albelda SM, et al., (2014) Giving Oncolytic Vaccinia Virus More BiTE. Mol Ther., vol. 22(1), p. 6-8.
Alcami et al., A Soluble Receptor for Interleukin-1B Encoded by Vaccinia Virus: A Novel Mechanism of Virus Modulation of the Host Response to Infection, 1992, Cell. 71(1), p. 153-67.
Alferink et al., Compartmentalized Production of CCL17 In Vivo . . . (2003) J. Exp. Med. 197, p. 585-599.
Altschul et al., Basic Local Alignment Search Tool, J. Mol. Biol., 1990, vol. 215, p. 403-410.
Altschul et al., Issues in Searching Molecular Sequence Databases, Nature Genet., vol. 6, p. 119-129, 1994.
Altschul, S. et al., Gapped BLAST and PSI-BLAST: a new generation of protein database search programs, Nucleic Acids Res., vol. 25, p. 3389-3402 (1997).
Alvarez-Breckenridge et al., NK Cells Impede Glioblastoma Virotherapy Through NKp30 and NKp46 Natural Cytotoxicity Receptors. Nature Medicine, vol. 18, p. 1827-34 (2012).
Andre et al., Hyal2 is a glycosylphosphatidylinositol-anchored, lipid raft-associated hyaluronidase, Biochemical and Biophysical Research Communications, 2011, vol. 411, p. 175-179.
Andtbacka et al., Talimogene Laherparepvec Improves Durable Response Rate in Patients with Advanced Melanoma.J Clin Oncol 2015; vol. 33(25), p. 2780-8.

Arming et al., In vitro mutagenesis of PH-20 hyaluronidase from human sperm, Eur. J. Biochem, 199, vol. 247, p. 810-814, 1995.
Bahar et al., Structure and Function of A41, a Vaccinia Virus Chemokine Binding Protein. PLoS Pathog 4, e5 (2008).
Baldrick et al., Safety Evaluation of a New Allergy Vaccine Containing the Adjuvant Monophosphoryl Lipid A (MPL) for the Treatment of Grass Pollen Allergy, Journal of Applied Toxicology, vol. 24, p. 261-268, 2004.
Baldrick et al., Safety Evaluation of Monophosphoryl Lipid A (MPL): An Immunostimulatory Adjuvant, Reg. Toxi. and Pharma., vol. 35, p. 398-413, 2002.
Baldridge, et al., Monophosphoryl lipid A enhances mucosal and systemic immunity to vaccine antigens following intranasal administration. Elsevier, Vaccine, 2000, vol. 18, p. 2416-2425.
Banaszynski et al., Chemical control of protein stability and function in living mice. Nat Med, vol. 14(10), p. 1123-127, 2008.
Banchereau et al., Dendritic cells as therapeutic vaccines against cancer. Nat Rev Immunol, vol. 5, 296-306 (2005).
Barve et al., Induction of Immune Responses and Clinical Efficacy in a Phase II Trial of IDM-2101, a 10-Epitope Cytotoxic T-Lymphocyte Vaccine, in Metastatic Non-Small-Cell Lung Cancer, J Clin Oncol 2008; vol. 26(27), p. 4418-25.
Beard et al., Transcription Mapping of Mouse Adenovirus Type 1 Early Region 3, Virology, 1990, 175, p. 81-90.
Beaucage & Caruthers, Deoxynucleoside Phosphoramidites—A New Class of Key Intermediates for Deoxypolynucleotide Synthesis, Tetra. Letts. 22(20):1859-1862, 1981.
Becker, Immunological and Regulatory Functions of Uninfected and Virus Infected Immature and Mature Subtypes of Dendritic Cells—a Review, Virus Genes, 2003, vol. 26, p. 119-130.
Belyakov, et al., What Role does the Route of Immunization Play in the Generation of Protective Immunity Against Mucosal Pathogens? Journal of Immunology, vol. 183, p. 6883-92 (2009).
Bernard, et al. Chronic Inhibition of Cyclooxygenase-2 Attenuates Antibody Responses Against Vaccinia Infection. Vaccine, vol. 28, p. 1363-72 (2010).
Binz et al., Chemovirotherapy: Combining chemotherapeutic treatment with oncolytic virotherapy, Oncolytic Virotherapy, 2015, vol. 4, p. 39-48.
Bischoff, et al., An Adenovirus Mutant that Replicates selectively in p53-Deficient Human Tumor Cells. Science, vol. 274, p. 373-6 (1996).
Bitter et al., Expression and Secretion Vectors for Yeast, Methods in Enzymology, vol. 153, p. 516-544, 1987.
Blasco el al., Dissociation of progeny vaccinia virus from the cell membrane is regulated by a viral envelope glycoprotein: effect of a point mutation in the lectin homology domain of the A34R gene, American Society for Microbiology Journals, Jun. 1, 1993, vol. 67, Iss. 6, pp. 3319-3325.
Boonstra, et al., Flexibility of mouse classical and plasmacytoid-derived dendritic cells in directing T helper type 1 and 2 cell development: dependency on antigen dose and differential toll-like receptor ligation, J. Exp. Med., vol. 197, p. 101-109 , 2003.
Brader, et al., Imaging of Lymph Node Micrometastases using an Oncolytic Herpes Virus and [18F]FEAU PET. PLoS One, vol. 4, e4789 (2009).
Breitbach, et al., Intravenous Delivery of a Multi-Mechanistic Cancer-Targeted Oncolytic Poxvirus in Humans. Nature, vol. 477, p. 99-102 (2011).
Brown et al., "The pI4 FAST Protein of Reptilian Reovirus Increases Vesicular Stomatitis Virus Neuropathogenesis", Journal of Virology, 2009, vol. 83, No. 2, p. 552-561.
Brown et al., Cancer Immunotherapy with Recombinant Poliovirus Induces IFN-Dominant Activation of Dendritic Cells and Tumor Antigen-Specific CTLs; Sci Trans Med. 2017; vol. 9, No. 408, pp. 1-37.
Brown, et al., Chemical Synthesis and Cloning of a Tyrosine tRNA Gene, Meth. Enzymol., vol. 68, p. 109-151, 1979.
Brummelkamp et al., Stable Suppression of Tumorigenicity by Virus-Mediated RNA Interference, Cancer Cell, vol. 2, p. 243-247 (2002).

(56) References Cited

OTHER PUBLICATIONS

Brzoza, et al., Cytoplasmic Entry of Listeria Monocytogenes Enhances Dendritic Cell Maturation and T Cell Differentiation and Function, J. Immunol., vol. 173, p. 2641-2651, 2004.

Bu et al., GRIM-19 Inhibits the STAT3 Signaling Pathway and Sensitizes Gastric Cancer Cells to Radiation, Gene, vol. 512(2), p. 198-205 (2013).

Buijs et al., Oncolytic viruses: From bench to bedside with a focus on safety, Human Vaccines & Immunotherapeutics, 2015, vol. 11(7), p. 1573-1584.

Buller et al., Decreased virulence of recombinant vaccinia virus expression vectors is associated with a thymidine kinase-negative phenotype, Nature 1985, vol. 317(6040), p. 813-5.

Buller et al., Poxvirus Pathogenesis, Microbiological Reviews, vol. 55, No. 1, Mar. 1991, p. 80-122.

Cantoni et al., Role of NK cells in immunotherapy and virotherapy of solic tumors, Immunotherapy, 2015, vol. 7, No. 8, p. 861-882.

Carine, et al., Mouse Strain Differences in Plasmacytoid Dendritic Cell Frequency and Function Revealed by a Novel Monoclonal Antibody, J. Immunol., vol. 171, p. 6466-6477, 2003.

Carpenter et al., STAT3 Target Genes Relevant to Human Cancers, Cancers, vol. 6, p. 897-925, 2014.

Carrillo et al., "Enhanced adaptation of vesicular stomatitis virus in cells infected with vaccinia virus", Infection, Genetics and Evolution, Elsevier, Amsterdam, NL, 2008, vol. 8, No. 5, pp. 614-620.

Chakir, et al., Differential of Murine NK Cells into Distinct Subsets Based on Variable Expression of the IL-12Rb2 Subunit, J. Immunol., vol. 165, p. 4985-4993, 2000.

Chakrabarti et al., Compact, Synthetic, Vaccinia Virus Early/Late Promoter for Protein Expression, Biotechniques, vol. 23, p. 1094-1097, Dec. 1997.

Chang et al., The E3L Gene of Vaccinia Virus Encodes an Inhibitor of the Interferon-Induced, Double-Stranded RNA-Dependent Protein Kinase, Proc. Natl. Acad. Sci., vol. 89(11), p. 4825-9, Jun. 1992.

Chang, et al., Treatment with Cyclooxygenase-2 Inhibitors Enables Repeated Administration of Vaccinia Virus for Control of Ovarian Cancer, Molecular Therapy, The Journal of the American Society of Gene Therapy 17, 1365-72 (2009).

Charafe, Jauffret et al., Breast Cancer Cell Lines Contain Functional Cancer Stem Cells with Metastatic Capacity and a Distinct Molecular Signature. Cancer Research, vol. 69, p. 1302-13 (2009).

Chartier et al., Efficient Generation of Recombinant Adenovirus Vectors by Homologous Recombination in *Escherichia coli*, Journal of Virology, Jul. 1996, vol. 7, No. 7, p. 4805-4810.

Contag, et al., Definition of an Enhanced Immune Cell Therapy in Mice that can Target Stem-like Lymphoma Cells. Cancer Research, vol. 70, p. 9837-45 (2010).

Smith et al., Comparison of Biosequences, Adv. Appl. Math., vol. 2, p. 482-489, 1981.

Smith et al., Immune Modulation by Proteins Secreted from Cells Infected by Vaccinia Virus. Arch Virol, Suppl 15, p. 111-29 (1999).

Smith et al., Infectious Poxvirus Vectors have Capacity for at Least 25 000 Base Pairs of Foreign DNA. Gene, vol. 25, p. 21-28 (1983).

Smith et al., Intracellular Cytokine Staining and Flow Cytometry: Considerations for Application in Clinical Trials of Novel Tuberculosis Vaccines, PLoS One (2015), vol. 10(9), e0138042.

Smith et al., Nonstochastic Coexpression of Activation Receptors on Murine Natural Killer Cells, J. Exp. Med., vol. 191, p. 1341-1354, (2000).

Smith G.L., et al., Vaccinia virus immune evasion. Immunol Rev, vol. 159, p. 137-154 (1997).

Sukumar et al., Mitochondrial Membrane Potential Identifies Cells with Enhanced Stemness for Cellular Therapy, Cell Metab, vol. 23(1), p. 63-76, 2016.

Sunderkotter, et al., Subpopulations of Mouse Blood Monocytes Differ in Maturation Stage and Inflammatory Response, J. Immunol., vol. 172, p. 4410-4417, 2004.

Sutter et al., A Recombinant Vector Derived from the Host Range-restricted and Highly Attenuated MVA Strain of Vaccinia Virus Stimulates Protective Immunity in Mice to Influenza Virus, Vaccine, vol. 12, No. 11, p. 1032-1040, 1994.

Symons et al., The vaccinia virus C 12L protein inhibits mouse IL-18 and promotes virus virulence in the murine intranasal model. J Gen Virol 83, 2833-2844 (2002).

Symons et al., Vaccinia Virus Encodes a Soluble Type I Interferon Receptor of Novel Structure and Broad Species Specificity, Cell., vol. 81(4), p. 551-60, 1995.

Takeshita et al., Toll-like Receptor Adaptor Molecules Enhance DNA-raised Adaptive Immune Responses Against Influenza and Tumors Through Activation of Innate Immunity. Journal of Virology, vol. 80, p. 6218-6224, 2006.

Tang et al., Endogenous HMGB1 regulates autophagy, J Cell Biol, vol. 190, No. 5, p. 881-892, 2010.

Taniguchi et al., The Regulatory Role of Va14 NKT Cells in Innate and Acquired Immune Response, Annu. Rev. Immunol., vol. 21, p. 483-513, 2003.

Terajima et al., Role of Indoleamine 2,3-Dioxygenase in Antiviral Activity of Interferon-gamma Against Vaccinia Virus. Viral Immunology, vol. 18, 722-9 (2005).

Thorne et al., Rational strain selection and engineering creates a broad-spectrum, systemically effective oncolytic poxvirus, JX-963. J Clin Invest, vol. 117, p. 3350-3358 (2007).

Thorne et al., Targeted and Armed Oncolytic Poxviruses: A Novel Multi-mechanistic Therapeutic Class for Cancer, Nat Rev Cancer, vol. 9, p. 64-71, 2009.

Thorne et al., Targeting localized immune suppression within the tumor through repeat cycles of immune cell-oncolytic virus combination therapy. Molecular Therapy : The Journal of the American Society of Gene Therapy, vol. 18, p. 1698-705 (2010).

Thorne SH, Design and testing of novel oncolytic vaccinia strains. Methods Mol Biol., Gene Therapy of Cancer, vol. 542, p. 635-647, 2009.

Thorne, Enhancing Biological Therapy through Conditional Regulation of Protein Stability. Expert Reviews in Molecular Medicine, vol. 12, e2 (2010).

Thorne, Immunotherapeutic Potential of Oncolytic Vaccinia Virus. Immunologic Research, vol. 50, p. 286-93 (2011).

Thorne, S. H. "Immunotherapeutic potential of oncolytic vaccinia virus," Frontiers in Oncology, Jun. 17, 2014, vol. 4, No. 155, pp. 1-5.

Thorne, Virus fuels NK cell killing of leukemia, 2016, Blood, vol. 127, Issue21, 2509.

Torres et al., Toll-Like Receptor 2 is Required for Optimal Control of Listeria monocytogenes Infection, Infection and Immunity, vol. 72, p. 2131-2139, 2004.

Tosic et al., Myxoma Virus Expressing a Fusion Protein of Interleukin-15 (IL15) and IL 15 Receptor Alpha has Enhanced Antitumor Activity, PLOS One, 2014, vol. 9, No. 10, p. 3109801.

Trumpfheller et al., The microbial mimic poly IC induces durable and protective CD4+ T cell immunity together with a dendritic cell targeted vaccine. Proceedings of the National Academy of Sciences of the United States of America, vol. 105, p. 2574-9 (2008).

Tsukamoto et al., Expression of the int-I gene in transgenic mice is associated with mammary gland hyperplasia and adenocarcinomas in male and female mice. Cell, vol. 55, p. 619-625, 1988.

Tuschl T. et al., Targeted mRNA degradation by double-stranded RNA in vitro, Genes & Development, vol. 13, p. 3191-3197, 1999.

Tvinnereim et al., Neutrophil Involvement in Cross-Priming CD8+ T Cell Responses to Bacterial Antigens, J. Immunol., vol. 17. p. 1994-2002, 2004.

Umemura et al. Defective NF-kappaB signaling in metastatic head and neck cancer cells leads to enhanced apoptosis by double-stranded RNA. Cancer Research, vol. 72, p. 45-55 (2012).

Van Der Windt et al., CD8 memory T cells have a bioenergetic advantage that underlies their rapid recall ability, PNAS, vol. 110(35), p. 14336-41, 2013.

Van Der Windt et al., Mitochondrial Respiratory Capacity Is A Critical Regulator Of CD8+ T Cell Memory Development, Immunity, vol. 36(1), p. 68-78, 2012.

Van Eijl et al., The Vaccinia Virus A36R Protein Is a Type Ib Membrane Protein Present on Intracellular but Not Extracellular Enveloped Virus Particles, Virology, vol. 271, p. 26-36, 2000.

(56) References Cited

OTHER PUBLICATIONS

Vella et al., Healthy individuals have T-cell and antibody responses to the tumor antigen cyclin BI that when elicited in mice protect from cancer. Proceedings of the National Academy of Sciences of the United States of America, vol. 106, p. 14010-5 (2009).

Visus et al., Targeting ALDH (bright) human carcinoma-initiating cells with ALDHIAI-specific CDS(+) T cells. Clinical Cancer Research : An Official Journal of the American Association for Cancer Research, vol. 17, p. 6174-84 (2011).

Von Beust, In vivo priming of bovine T lymphocytes with vaccinia viruses expresssing the bovine leukemia virus envelope gene together with bovine interleukin-4 or bovine interleukin-12, Washington State University, 1997, p. 1-18.

Walzer et al., Differential In Vivo Persistence of Two Subsets of Memory Phenotype CD8 T Cells Defined by CD44 and CD122 Expression Levels, J. Immunol., vol. 168, p. 2704-2711, 2002.

Wang et al., Treating Tumors With a Vaccinia Virus Expressing IFNbeta Illustrates the Complex Relationships Between Oncolytic Ability and Immunogenicity. Molecular Therapy : The Journal of the American Society of Gene Therapy, vol. 20, No. 4, p. 736-748, (2012).

Weber et al., antiSMASH 3.0—a comprehensive resource for the genome mining of biosynthetic gene clusters, Nucleic Acids Research, vol. 43, W237-W243, 2015.

Wei et al., Interleukin-2 administration alters the CD4+FOXP3+ T-cell pool and tumor trafficking in patients with ovarian carcinoma. Cancer Research, vol. 67, p. 7487-94 (2007).

Weiss et al., Trafficking of high avidity HER-2/neu-specific T cells into HER-2/neu-expressing tumors after depletion of effector/memory-like regulatory T cells. PLoS One 7, vol. 7, e31962 (2012).

Wesa et al., Polarized type-I dendritic cells (DCI) producing high levels of IL-12 family members rescue patient THI-type antimelanoma CD4+ T cell responses in vitro. J Immunother, vol. 30, p. 75-82 (2007).

Whitman et al., In vitro and in vivo kinetics of recombinant vaccinia virus cancer-gene therapy. Surgery. Surgery 1994; vol. 116(2), p. 183-8.

Wong et al., Helper Activity of Natural Killer Cells During the Dendritic Cell-mediated Induction of Melanoma-specific Cytotoxic T Cells. Journal of Immunotherapy, vol. 34, 270-8 (2011).

Workenhe et al., Mitoxantrone synergizes with oncolytic herpes simplex virus to regress established breast tumors in part by increasing recruitment of CDS+ T cells. 7th International Oncolytic Viruses Meeting (Quebec City, 2013).

Worschech A., et al, Systemic treatment of xenografts with vaccinia virus GLV-I h68 reveals the immunologic facet of oncolytic therapy. BMC Genomics vol. 10, 301 (2009).

Yan et al., (2012) High mobility group box 1 activates caspase-1 and promotes hepatocellular carcinoma invasiveness and metastases. Hepatology. Jan. 11, 2012, vol. 55, Issue 6, pp. 1863-1875.

Yang et al, Mechanisms of Monophosphoryl Lipid A Augmentation of Host Responses to Recombinant HagB from Porphyromonas gingivalis, Infection and Immunity, Jul. 2002, vol. 70, No. 7, p. 3557-3565.

Yang et al., Persistent Toll-like receptor signals are required for reversal of regulatory T cell-mediated CD8 tolerance. Nature Immunology, vol. 5, p. 508-15 (2004).

\* cited by examiner

FIG. 1

ONCOLYTIC IMMUNOTHERAPY BY TUMOR MICRO-ENVIRONMENT REMODELING

CROSS REFERENCE

This application is a continuation application of PCT/US2021/059887, filed Nov. 18, 2021, which claims the benefit of U.S. Provisional Application No. 63/116,004, filed Nov. 19, 2020, which application is incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties. In the event of a conflict between a term as used herein and the term as defined in the incorporated reference, the definition of this disclosure controls.

SEQUENCE LISTING

The instant application contains a Sequence Listing which has been submitted electronically in AT.26 (xml) format and is hereby incorporated by reference in its entirety. Said AT.26 (xml) copy, created on Apr. 18, 2023, is named 199249_703301_xml and is 14,572 bytes in size.

BACKGROUND

In recent years, immunotherapy has emerged as an extremely efficient tool for cancer treatments. In solid tumors, immunotherapies using monoclonal antibody-mediated "checkpoint" blockade of Programmed Death 1 (PD-1) and cytotoxic T-lymphocyte-associated antigen (CTLA-4) have resulted in durable responses, leading to US Food and Drug Administration (FDA) approval in a variety of indications (La-Beck et al., 2015; Mahoney et al., 2015). These single-agent immunotherapies do not result in long-term durable benefits in most patients (Herbst et al., 2014; Weber et al., 2015) because of the more dominant immunosuppressive mechanisms that limit T-cell function in the tumor microenvironment (Sharma et al, 2015). There is a need for the development of an improved oncolytic immunotherapy to remodel the tumor microenvironment to enhance T-cell function and differentiation and is capable of enhanced systemic delivery of the virus.

BRIEF SUMMARY

Provided herein are modified oncolytic vaccinia viruses comprising: an exogenous nucleic acid encoding a fusion protein comprising a metabolic modulating protein or a functional fragment or a variant thereof, wherein the exogenous nucleic acid encoding for the fusion protein comprises: a polypeptide comprising IL-2 or a functional fragment thereof, and a polypeptide comprising leptin or a functional fragment thereof; an exogenous nucleic acid encoding a chemokine receptor or a functional fragment or a variant thereof, wherein the chemokine receptor is CCR2; and a genetic modification in a viral genome of the modified oncolytic virus. Further provided herein are modified oncolytic viruses, wherein the exogenous nucleic acid encoding the chemokine receptor comprises a codon optimized variant of the human coding sequence of the chemokine receptor. Further provided herein are modified oncolytic viruses, wherein the fusion protein further comprises a cytokine or a functional fragment or a variant thereof. Further provided herein are modified oncolytic viruses, wherein the genetic modification in the viral backbone is a mutation or a deletion of the A52R gene. Further provided herein are modified oncolytic viruses, wherein the deletion is a complete or a partial deletion. Further provided herein are modified oncolytic viruses, wherein the oncolytic virus further comprises a deletion of thymidine kinase gene. Further provided herein are modified oncolytic viruses, wherein the oncolytic virus comprises measles virus, poliovirus, poxvirus, vaccinia virus, an adenovirus, an adeno-associated virus, herpes simplex virus, vesicular stomatitis virus, reovirus, Newcastle disease virus, Seneca virus, lentivirus, mengovirus, or a myxoma virus. Further provided herein are modified oncolytic viruses, wherein the oncolytic virus is a pox virus. Further provided herein are modified oncolytic viruses, wherein the pox virus is a vaccina virus. Further provided herein are modified oncolytic viruses, wherein the vaccinia virus is a Western Reserve strain Vaccinia virus, a Copenhagen strain, an IHD strain, a Wyeth strain, a NYCBOH strain, a Tian Tan strain, a Lister strain, an Ankara strain, a USSR strain, an ACAM2000 strain, a Paris strain, a Bern strain, a Temple of Heaven strain, a Dairen strain, an EM-63 strain, an Evans strain, a King strain, a Patwadangar strain, or a Tash Kent strain. Further provided herein are modified oncolytic viruses, wherein the exogenous nucleic acid encoding the fusion protein is cloned into the locus of thymidine kinase gene. Further provided herein are modified oncolytic viruses, wherein the exogenous nucleic acid encoding the chemokine receptor is cloned into a locus of an A52R gene. Further provided herein are modified oncolytic viruses, wherein the polypeptide encoding IL-2 or a functional fragment thereof comprises a sequence that is at least about 75%, about 80%, about 85%, about 90%, about 95%, about 96%, about 97%, about 98%, about 99%, or about 100% homologous to the sequence of SEQ ID NO: 5. Further provided herein are modified oncolytic viruses, wherein polypeptide encoding leptin or a functional fragment thereof comprises a sequence that is at least about 75%, about 80%, about 85%, about 90%, about 95%, about 96%, about 97%, about 98%, about 99%, or about 100% homologous to the sequence of SEQ ID NO: 4. Further provided herein are modified oncolytic viruses, wherein the exogenous nucleic acid encoding the fusion protein comprising a metabolic modulating protein or a functional fragment or a variant thereof comprises a sequence that is at least about 75%, about 80%, about 85%, about 90%, about 95%, about 96%, about 97%, about 98%, about 99%, or about 100% homologous to the sequence of SEQ ID NO: 1. Further provided herein are modified oncolytic viruses, wherein the exogenous nucleic acid encoding the chemokine receptor or a functional fragment or a variant thereof comprises a sequence that is at least about 75%, about 80%, about 85%, about 90%, about 95%, about 96%, about 97%, about 98%, about 99%, or about 100% homologous to the sequence of SEQ ID NO: 2 or SEQ ID NO: 3. Further provided herein are modified oncolytic viruses, further comprising an exogenous nucleic acid encoding a hyaluronidase. Further provided herein are modified oncolytic viruses, wherein the hyaluronidase is PH-20 or HysA.

Provided herein are modified oncolytic viruses comprising an exogenous nucleic acid encoding a leptin-interleukin (IL)-2 fusion protein; an exogenous nucleic acid encoding CCR2, and a deletion of A52R gene. Further provided herein are modified oncolytic viruses, wherein the oncolytic virus comprises measles virus, poliovirus, poxvirus, vaccinia virus, an adenovirus, an adeno-associated virus, herpes simplex virus, vesicular stomatitis virus, reovirus, Newcastle disease virus, Seneca virus, lentivirus, mengovirus, or a myxoma virus. Further provided herein are modified oncolytic viruses, wherein the oncolytic virus is a pox virus. Further provided herein are modified oncolytic viruses, wherein the pox virus is a vaccina virus. Further provided herein are modified oncolytic viruses, wherein the vaccinia virus is a Western Reserve strain Vaccinia virus, a Copenhagen strain, an IHD strain, a Wyeth strain, a NYCBOH strain, a Tian Tan strain, a Lister strain, an Ankara strain, a USSR strain, an ACAM2000 strain, a Paris strain, a Bern strain, a Temple of Heaven strain, a Dairen strain, an EM-63 strain, an Evans strain, a King strain, a Patwadangar strain, or a Tash Kent strain. Further provided herein are modified oncolytic viruses, wherein the oncolytic virus further comprises a deletion of a thymidine kinase gene. Further provided herein are modified oncolytic viruses, wherein the exogenous nucleic acid encoding the leptin-interleukin (IL)-2 fusion protein is cloned into the locus of the thymidine kinase gene. Further provided herein are modified oncolytic viruses, wherein the nucleic acid encoding CCR2 is cloned into a locus of A52R gene. Provided herein are modified oncolytic viruses of any of the previous disclosures, further comprising a mutation or a deletion of a viral gene selected from the group consisting of: A1, A2, VH1, A33, 17, K7R, B8R, C12L, B15R, B14R, K1L, N1L, M2L, A49R, A46R. E3L. C4, C16, and a functional domain or a fragment or a variant thereof, or any combinations thereof. Further provided herein are modified oncolytic viruses, further comprising an exogenous nucleic acid coding for at least one of: HMGB1, PIAS3, LIGHT, fractalkine, ITAC, IL15, IL15Ralpha, CCL5, a functional domain or a fragment or a variant thereof, or any combinations thereof.

Provided herein are pharmaceutical compositions comprising a modified oncolytic virus according to any of the previous disclosures. Further provided herein are pharmaceutical compositions, further comprising at least one of: a solubilizing agent, an excipient, or a pharmaceutically acceptable carrier. Further provided herein are pharmaceutical compositions, wherein the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combinations thereof. Further provided herein are pharmaceutical compositions, wherein the excipient comprises di-sodium hydrogen phosphate dihydrate, sodium dihydrogen phosphate dihydrate, sodium chloride, myo-inositol, sorbitol, or any combinations thereof. Further provided herein are pharmaceutical compositions, that do not comprise a preservative. Further provided herein are pharmaceutical compositions, further comprising one or more of a preservative, a diluent, and a carrier. Further provided herein are pharmaceutical compositions, further comprising an additional active ingredient or a salt thereof. Further provided herein are pharmaceutical compositions, wherein the solubilizing agent is sterile water. Further provided herein are pharmaceutical compositions, further comprising an additional active ingredient, wherein the additional active ingredient is an anti-cancer agent or a further oncolytic virus.

Provided herein are kits comprising the modified oncolytic virus of any of the previous disclosures. Provided herein are kits comprising the pharmaceutical composition of any of the previous disclosures. Further provided herein are kits further comprising at least one of: an anti-cancer agent or an additional oncolytic virus.

Provided herein are methods of enhancing therapeutic effect of a modified oncolytic virus upon systemic delivery of the modified oncolytic virus to a subject, relative to a systemic administration of a reference virus comprising a TK mutation but not the exogenous nucleic acid encoding the fusion protein or the exogenous nucleic acid encoding the chemokine receptor, comprising a systemic administration of the modified oncolytic virus according to any of the previous disclosures, or the pharmaceutical composition as defined in any of the previous disclosures.

Provided herein are methods of treatment comprising administering to a subject the oncolytic virus according to any of the previous disclosures, or the pharmaceutical composition of any of the previous disclosures, wherein the administering results in an enhanced systemic immune response in the subject, relative to administering to the subject a reference oncolytic virus that comprises a deletion of a thymine kinase gene (TK−), does not comprise the exogenous nucleic acid encoding a fusion protein comprising a metabolic modulating protein or functional fragment or variant thereof or the exogenous nucleic acid encoding the chemokine receptor or functional fragment or variant thereof. Further provided herein are methods, wherein the administering is a systemic administration. Further provided herein are methods, wherein the systemic administration comprises at least one of: intratumoral, intravenous, parenteral, intradermal, intramuscular, transdermal, rectal, intraurethral, intravaginal, intranasal, intrathecal, intraperitoneal, intradental, subcutaneous, percutaneous, intratracheal, intraarterial, intravesical, inhalation, oral or any combinations thereof. Further provided herein are methods, wherein the administration is intratumoral. Further provided herein are methods, wherein the administration is intravenous. Further provided herein are methods, wherein the subject has a cancer.

Provided herein are methods of treating a cancer in a subject, said method comprising administering to said subject a therapeutically effective amount of the modified oncolytic virus of any of the previous disclosures. Further provided herein are methods, wherein the cancer is at least one of: a melanoma, a hepatocellular carcinoma, a breast cancer, a lung cancer, a Non-small lung cancer, a peritoneal cancer, a prostate cancer, a bladder cancer, an ovarian cancer, a leukemia, a lymphoma, a renal cell carcinoma, a pancreatic cancer, an epithelial carcinoma, a gastric/GE junction adenocarcinoma, a cervical cancer, a colon carcinoma, a colorectal cancer, a duodenal cancer, a pancreatic adenocarcinoma, an adenoid cystic, a sarcoma, a mesothelioma, a glioblastoma multiforme, a astrocytoma, a multiple myeloma, a prostate carcinoma, a hepatocellular carcinoma, a cholangiocarcinoma, a pancreatic adenocarcinoma, a head and neck squamous cell carcinoma, a cervical squamous-cell carcinoma, an osteosarcoma, an epithelial ovarian carcinoma, an acute lymphoblastic lymphoma, a myeloproliferative neoplasm, or any combinations thereof. Further provided herein are methods, wherein the modified oncolytic virus, or the pharmaceutical composition is administered at a dosage that comprises about $10^6$ PFU/mL to about $10^{10}$ PFU/mL of the oncolytic virus. Further provided herein are methods, wherein the modified oncolytic virus, or the pharmaceutical composition is administered at a dosage that comprises about $5 \times 10^9$ PFU/mL of the oncolytic virus. Further provided herein are methods, wherein the modified oncolytic virus, or the pharmaceutical composition is administered, independently, in an initial dose for a first period of time, an intermediate dose for a second period of time, and a high dose for a third period of time. Further provided herein are methods, comprising administration of the initial, the intermediate, and the high dose, independently, wherein the initial dose is lower than the intermediate dose and the intermediate dose is lower than the high dose. Further provided herein are methods Further provided herein are, wherein the first, second, and third periods of time are each from about 1 week to about 3 weeks. Further provided herein are methods, wherein the modified oncolytic virus, and the pharmaceutical composition independently comprises a liquid dosage form that is administered at a volume of about 1 mL to about 5 mL, about 5 mL to 10 mL, about 15 mL to about 20 mL, about 25 mL to about 30) mL, about 30) mL to about 50 mL, about 50) mL to about 100 mL, about 100 mL to 150 mL. about 150 mL to about 200 mL, about 200 mL to about 250 mL, about 250) mL to about 300 mL, about 300) mL to about 350) mL, about 350) mL to about 400 mL, about 400 mL to about 450) mL, about 450) mL to 500 mL, about 500 mL to 750 mL, or about 750) mL to 1000 mL. Further provided herein are methods, wherein the modified oncolytic virus or the pharmaceutical composition is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein are methods, wherein the modified oncolytic virus or the pharmaceutical composition is administered for a duration of about 1 week, about 2 weeks, about 3 weeks, about 4 weeks, about 6 weeks, about 7 weeks, about 8 weeks, about 9 weeks, about 10, weeks, or about 12 weeks. Further provided herein are methods, wherein the modified oncolytic virus, or the pharmaceutical composition is administered once daily, twice daily, once every week, once every two weeks, or once every three weeks. Further provided herein are methods, wherein the modified oncolytic virus, or the pharmaceutical composition is administered intravenously, intraperitoneally, or by an intratumoral injection. Further provided herein are methods, wherein the modified oncolytic virus or the pharmaceutical composition is administered as a bolus injection or a slow infusion. Further provided herein are methods, wherein the administration of the modified oncolytic virus or the pharmaceutical composition results in a first peak viral load after about 1 hour to about 3 days and a second peak viral load after about 3 days to about 10 days from administration of a first dose. Further provided herein are methods, comprising administration of a further therapy, wherein the further therapy is administered for a duration of about 1 week, about 2 weeks, about 3 weeks, about 4 weeks, about 6 weeks, about 7 weeks, about 8 weeks, about 9 weeks, about 10, weeks, or about 12 weeks. Further provided herein are methods, wherein the further therapy is administered once daily, once every week, once every two weeks, or once every three weeks. Further provided herein are methods, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein are methods, wherein the further therapy is administered for a duration of about 1 week, about 2 week, about 3 weeks, about 4 weeks, about 6 weeks, about 7 weeks, about 8 weeks, about 9 weeks, about 10, weeks, or about 12 weeks. Further provided herein are methods, wherein the further therapy is administered once daily, once every week, once every two weeks, or once every three weeks. Further provided herein are methods, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein are methods, wherein the further therapy is administered orally, intravenously, by an intratumoral injection, or by radiation. Further provided herein are methods, wherein the subject is human. Further provided herein are methods, wherein prior to administration of the modified oncolytic virus or the pharmaceutical composition the subject has been diagnosed with a cancer. Further provided herein are methods, wherein prior to administration of the modified oncolytic virus or the pharmaceutical composition or the further therapy the subject has been diagnosed with a cancer. Further provided herein are methods, wherein the further therapy comprises chemotherapy, radiation, oncolytic viral therapy with an additional virus, treatment with immunomodulatory proteins, a CAR T cellular therapy, an anti-cancer agent, or any combinations thereof. Further provided herein are methods, wherein the further therapy comprises administration of an immunomodulatory agent comprising anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist. Further provided herein are methods, comprising administration of the further therapy, wherein the further therapy comprises administration of the anti-cancer agent, wherein the anti-cancer agent is a chemotherapeutic agent.

BRIEF DESCRIPTION OF THE DRAWINGS

The novel features of the disclosure are set forth with particularity in the appended claims. A better understanding of the features and advantages of this disclosure will be obtained by reference to the following detailed description that sets forth illustrative embodiments, in which the principles of this disclosure are utilized, and the accompanying drawings of which.

FIG. 1 shows a diagrammatic representation of the genes deleted from the vaccinia virus backbone and exogenous genes substituted at the respective loci to engineer the exemplary modified vaccinia virus (abbreviated as "MMC") of the present disclosure.

DETAILED DESCRIPTION

Definitions

Figure 2A:
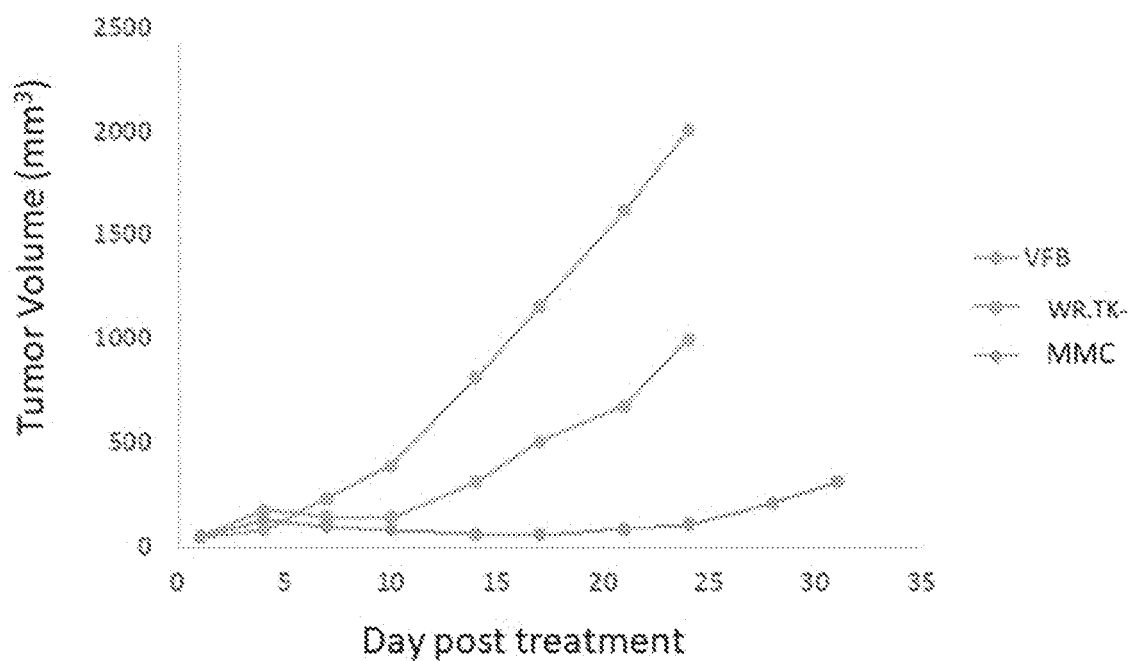
FIG. 2A-2D show an exemplary modified vaccinia virus (abbreviated as "MMC") modified to delete A52R and TK genes and inserting CCR2 and LEPTIN-IL-2 shows enhanced therapeutic effect and systemic delivery in LLC (Lewis Lung Carcinoma) tumor models.

The terminology used herein is for the purpose of describing particular cases only and is not intended to be limiting. As used herein, the singular forms "a", "an" and "the" can include the plural forms as well, unless the context clearly indicates otherwise. Furthermore, to the extent that the terms "contains," "containing," "including", "includes," "having," "has", "with", or variants thereof are used in either the detailed description and/or the claims, such terms are intended to be inclusive in a manner similar to the term "comprising."

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value, such as #10% of the value modified by the term "about".

The terms "individual," "patient," or "subject" can be used interchangeably. None of the terms require or are limited to situations characterized by the supervision (e.g., constant or intermittent) of a health care worker (e.g., a doctor, a registered nurse, a nurse practitioner, a physician's assistant, an orderly, or a hospice worker). In some embodiments, patients, subjects, or individuals can be under the supervision of a health care worker.

The terms "heterologous nucleic acid sequence," or "exogenous nucleic acid sequence," as used herein, in relation to a specific virus can refer to a nucleic acid sequence that originates from a source other than the specified virus. A "heterologous" gene, nucleic acid, antigen, or protein is understood to be a nucleic acid or amino acid sequence which is not present in the wild-type poxviral genome (e.g., MVA or MVA-BN). A "heterologous gene," when present in a vaccinia virus such as MVA or MVA-BN, can be incorporated into the poxviral genome in such a way that, following administration of the modified vaccinia virus to a host cell, it is expressed as the corresponding heterologous gene product, such as the "heterologous antigen" and/or "heterologous protein." Expression can be achieved by operatively linking the heterologous gene to regulatory elements that allow expression in the vaccinia virus-infected cell. The regulatory elements include a natural or synthetic vaccinia virus promoter.

As used herein, the terms "expressed," "express," "expression," and the like which can be used interchangeably may denote the transcription alone as well as both the transcription and translation of a sequence of interest. Thus, in referring to expression of a nucleotide sequence present in the form of DNA, the product resulting from this expression may be either RNA (resulting from transcription alone of the sequence to be expressed) or a polypeptide sequence (resulting from both transcription and translation of the sequence to be expressed). The term "expression" may also include the possibility that both RNA and polypeptide product result from said expression and remain together in the same shared milieu. For example, this is the case when the mRNA persists following its translation into polypeptide product. As used herein, the term "expression cassette" can be defined as a part of a vector or recombinant virus typically used for cloning and/or transformation. An expression cassette can be comprised of a) one or more coding sequences (e.g., open reading frame (ORF), genes, nucleic acids encoding a protein and/or antigen), and b) sequences controlling expression of one or more coding sequences (e.g., a promoter). Additionally, an expression cassette may comprise a 3' untranslated region (e.g., a transcriptional terminator such as a vaccinia transcriptional terminator). "Expression cassette" can be used interchangeably with the term "transcriptional unit."

The term "mutation," as used herein, can refer to a deletion, an insertion of a heterologous nucleic acid, an inversion or a substitution, including an open reading frame ablating mutations as commonly understood in the art.

The term "gene," as used herein, can refer to a segment of nucleic acid that encodes an individual protein or RNA (also referred to as a "coding sequence" or "coding region"), optionally together with associated regulatory regions such as promoters, operators, terminators, and the like, which may be located upstream or downstream of the coding sequence.

The terms "mutant virus" and "modified virus," as used interchangeably herein, can refer to a virus comprising one or more mutations in its genome, including but not limited to deletions, insertions of heterologous nucleic acids, inversions, substitutions, or combinations thereof.

The term "naturally-occurring," as used herein with reference to a virus, can indicate that the virus can be found in nature, i.e., it can be isolated from a source in nature and has not been intentionally modified.

The terms "inhibiting," "reducing" or "prevention," or any variation of these terms, referred to herein, can include any measurable decrease or complete inhibition to achieve a desired result.

A "promoter," as used herein, can be a control sequence that is a region of a nucleic acid sequence at which initiation and rate of transcription are controlled. In certain embodiments, a promoter may contain genetic elements at which regulatory proteins and molecules may bind such as RNA polymerase and other transcription factors. The terms "operatively positioned," "operatively linked," "operably linked," "under control" and "under transcriptional control" can mean that a promoter is in a correct functional location and/or orientation in relation to a nucleic acid sequence to control transcriptional initiation and/or expression of that sequence. In certain embodiments, a promoter may or may not be used in conjunction with an "enhancer," which refers to a cis-acting regulatory sequence involved in the transcriptional activation of a nucleic acid sequence.

As used herein, the term "promoter" can denote a regulatory region of a nucleic acid, usually DNA, located upstream of the sequence of a nucleic acid to be expressed, which contains specific DNA sequence elements, that are recognized and bound e.g., by protein transcription factors and polymerases responsible for synthesizing the RNA from the coding region of the gene being promoted. As promoters are typically immediately adjacent to the gene in question, positions in the promoter are designated relative to the transcriptional start site, where transcription of DNA begins for a particular gene (i.e., positions upstream are negative numbers counting back from −1, for example, −100 is a position 100 base pairs upstream). Thus, the promoter sequence may comprise nucleotides until position −1. However, nucleotides from position +1 are not part of the promoter, i.e., in this regard it has to be noted that the translation initiation codon (ATG or AUG) is not part of the promoter. A "natural vaccinia virus promoter" can be an endogenous promoter of the vaccinia virus genome. A "synthetic vaccinia virus promoter" can mean a recombinant engineered promoter active to direct transcription of the nucleic acid to be expressed by a vaccinia virus (e.g., a modified vaccinia virus in CEF cells).

As used herein, "operably linked" means that the components described are in relationship permitting them to function in their intended manner e.g., a promoter to transcribe the nucleic acid to be expressed. A first nucleic acid sequence is operably linked to a second nucleic acid sequence when the first nucleic acid sequence is placed in a functional relationship with the second nucleic acid sequence. For example, a promoter is operably linked to a coding sequence if the promoter is placed in a position where it can direct transcription of the coding sequence. Generally, operably linked DNA sequences are contiguous and, where necessary to join two protein-coding regions, in the same reading frame.

The term "nucleic acid." "nucleotide sequence," "nucleic acid sequence" and "polynucleotide" can be used interchangeably and refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides, or solid support. The polynucleotides can be obtained by chemical synthesis or derived from a microorganism.

The term "open reading frame" (ORF) can refer to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, such as, by gene-technological means. An ORF can code for a protein where the amino acids into which it can be translated form a peptide-linked chain.

As used herein, the term "essential ORF" can mean an ORF which when being experimentally partially or fully deleted e.g., in a modified vaccinia virus, the modified vaccinia virus replication, growth or both replication and growth are reduced (e.g., by at least 15 fold in the mutant compared to a modified vaccinia virus without the deletion). Methods to determine MVA virus replication and growth of the virus are well known to the skilled person. For example, methods are described in Vaccinia Virus and Poxvirology, Methods and Protocols, Volume 269 Ed. By Stuart N. Isaacs (Humana Press (2004), see e.g., Chapter 8, Growing Poxviruses and determining Virus Titer, Kotwal and Abrahams). Viral growth rates of MVA may be determined by GFP fluorescence as, for example, described in Orubu et al. (2012) PLOS One 7: e40167 using e.g., CEF cells or the method as described in Hornemann et al. (2003), Journal of Virology 77:8394-8407.

Codon optimization is a technique that may be used to maximize the protein expression in an organism by increasing the translational efficiency of the gene of interest. Different organisms often show particular preferences for one of the several codons that encode the same amino acid due to mutational biases and natural selection. For example, in fast growing microorganisms such as E. coli, optimal codons reflect the composition of their respective genomic tRNA pool. Therefore, the codons of low frequency of an amino acid may be replaced with codons for the same amino acid but of high frequency in the fast growing microorganism. Accordingly, the expression of the optimized DNA sequence is improved in the fast growing microorganism. As provided herein, polynucleotide sequences may be codon optimized for optimal polypeptide expression in a particular organism, such as a human. The polynucleotides of the disclosure can include sequences that are degenerate as a result of the genetic code, e.g., optimized codon usage or codon usage adaptation for expression in a specific host in particular for mammalian expression. As used herein, "optimized" or "optimization" can refer to a polynucleotide that is genetically engineered to increase its expression in a given species. To provide optimized polynucleotides coding for a protein expressed by a modified vaccinia virus of this disclosure, for instance, a chemokine receptor protein, the DNA sequence of the chemokine receptor protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of the chemokine receptor protein in said species can be achieved by utilizing the distribution frequency of codon usage in eukaryotes and prokaryotes, or in a particular species. The term "frequency of preferred codon usage" can refer to the preference exhibited by a specific host cell in usage of nucleotide codons to specify a given amino acid. There are 20 natural amino acids, most of which are specified by more than one codon. Therefore, all degenerate nucleotide sequences can be included in the disclosure as long as the amino acid sequence of the protein (e.g., a chemokine receptor protein) encoded by the nucleotide sequence is functionally unchanged.

The term "recombinant" when applied to a nucleic acid, vector, e.g., a modified vaccinia virus vector and the like can refer to a nucleic acid, vector, or made by an artificial combination of two or more otherwise heterologous segments of nucleic acid sequence, or to a nucleic acid, vector or comprising such an artificial combination of two or more otherwise heterologous segments of nucleic acid sequence. The artificial combination is most commonly accomplished by artificial manipulation of isolated segments of nucleic acids, using well-established genetic engineering techniques. Generally, a "recombinant" modified vaccinia virus as described herein can refer to modified vaccinia viruses that can be produced by standard genetic engineering methods. For instance, in some aspects, the modified vaccinia viruses of the present disclosure can thus be genetically engineered or genetically modified vaccinia viruses. The term "recombinant MVA" can thus include modified vaccinia viruses (e.g., MVA-BN) which have stably integrated recombinant nucleic acid, e.g., in the form of a transcriptional unit, in their genome. A transcriptional unit may include a promoter, enhancer, terminator and/or silencer. Recombinant modified vaccinia viruses of this disclosure may express heterologous antigenic determinants, polypeptides, or proteins (antigens) upon induction of the regulatory elements.

As used herein, "transcriptional terminator" can be comprised of a DNA sequences involved in specific termination of an RNA transcript by an RNA polymerase. Vaccinia virus including MVA RNA polymerase terminates transcription downstream of an RNA signal (UUUUUNU, TTTTTNT or T5NT on the DNA level) in the nascent RNA (Earl et al. (1990), J. Virol. 64:2448-2451). "Transcriptional terminator" can sometimes be referred to as a "termination signal" in the literature and thus can be used interchangeably.

The terms "protein," "peptide," "polypeptide" and "polypeptide fragment" can be used interchangeably herein and can refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

The term "homology," as used herein, may be to calculations of "homology" or "percent homology" between two or more nucleotide or amino acid sequences that can be determined by aligning the sequences for optimal comparison purposes (e.g., gaps can be introduced in the sequence of a first sequence). The nucleotides at corresponding positions may then be compared, and the percent identity between the two sequences may be a function of the number of identical positions shared by the sequences (i.e., % homology=# of identical positions/total # of positions×100). For example, a position in the first sequence may be occupied by the same nucleotide as the corresponding position in the second sequence, then the molecules are identical at that position. The percent homology between the two sequences may be a function of the number of identical positions shared by the sequences, taking into account the number of gaps, and the length of each gap, which need to be introduced for optimal alignment of the two sequences. In some embodiments, the length of a sequence aligned for comparison purposes may be at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search may determine homology between two sequences. The homology can be between the entire lengths of two sequences or between fractions of the entire lengths of two sequences. The two sequences can be genes, nucleotides sequences, protein sequences, peptide sequences, amino acid sequences, or fragments thereof. The actual comparison of the two sequences can be accomplished by well-known methods, for example, using a mathematical algorithm. A non-limiting example of such a mathematical algorithm may be described in Karlin, S. and Altschul, S., Proc. Natl. Acad. Sci. USA, 90)-5873-5877 (1993). Such an algorithm may be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In another embodiment, the percent identity between two amino acid sequences can be accomplished using, for example, the GAP program in the GCG software package (Accelrys, Cambridge, UK).

The term "subject" can refer to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

An "animal," as used herein can include mammals, birds, and the like. Animal or host can include mammals and humans. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish.

The terms "treat," "treating," and "treatment" can be meant to include alleviating or abrogating a disorder, disease, or condition; or one or more of the symptoms associated with the disorder, disease, or condition; or alleviating or eradicating the cause(s) of the disorder, disease, or condition itself. Desirable effects of treatment can include, but are not limited to, preventing occurrence or recurrence of disease, alleviation of symptoms, diminishing any direct or indirect pathological consequences of the disease, preventing metastasis, decreasing the rate of disease progression, amelioration or palliation of the disease state and remission or improved prognosis.

The term "therapeutically effective amount" can refer to the amount of a compound that, when administered, can be sufficient to prevent development of, or alleviate to some extent, one or more of the symptoms of the disorder, disease, or condition being treated. The term "therapeutically effective amount" can also refer to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient." "physiologically acceptable carrier," or "physiologically acceptable excipient" can refer to a pharmaceutically-acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See. *Remington: The Science and Practice of Pharmacy,* 21st Edition; Lippincott Williams & Wilkins: Philadelphia, PA, 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, FL, 2004).

The term "pharmaceutical composition" can refer to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, and the like.

A "formulation" can refer to a composition containing an active pharmaceutical or biological ingredient e.g., a modified vaccinia virus of this disclosure, along with one or more additional components. The term "formulation" can be used interchangeably with the terms "pharmaceutical composition," "vaccine composition," and "vaccine formulation" herein. The formulations can be liquid or solid (e.g., lyophilized).

The term "immunogenic composition" or "immunological composition," can cover a composition that may elicit an immune response against an antigen of interest expressed from a modified vaccinia virus as described herein. The term "vaccine or vaccine composition," can cover any composition that may induce a protective immune response against the antigens of interest, or which may efficaciously protect against the antigen of interest; e.g., after administration or injection into the animal or human elicits a protective immune response against the antigen or provides efficacious protection against the antigen expressed from a modified vaccinia virus vector. The composition can be administered alone, or can be administered sequentially with other compositions or therapeutic compositions thereby providing a combination composition, a cocktail or multivalent mixture of two or more, such as three, four, five or six compositions.

An "anti-cancer agent," as used herein, can refer to an agent or therapy that is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Non-limiting examples of anti-cancer agents can include biological agents (biotherapy), chemotherapy agents, and radiotherapy agents.

The term "prime-boost vaccination" can refer to a vaccination strategy using a first, priming injection of a vaccine targeting a specific antigen followed at intervals by one or more boosting injections of the same vaccine. Prime-boost vaccination may be homologous or heterologous. A homologous prime-boost vaccination can use a vaccine comprising the same immunogen and vector for both the priming injection and the one or more boosting injections. A heterologous prime-boost vaccination uses a vaccine comprising the same immunogen for both the priming injection and the one or more boosting injections but different vectors for the priming injection and the one or more boosting injections. For example, a homologous prime-boost vaccination may use a modified vaccinia virus vector comprising the same nucleic acids expressing antigens of interest for both the priming injection and the one or more boosting injections. In contrast, a heterologous prime-boost vaccination may use a modified vaccinia virus vector comprising nucleic acids expressing one antigenic protein for the priming injection and another modified vaccinia virus vectors expressing another antigenic protein not contained in the priming injection or vice versa. Heterologous prime-boost vaccination may also encompass various combinations such as, for example, use of a plasmid encoding an immunogen in the priming injection and use of a modified vaccinia virus encoding the same immunogen in the one or more boosting injections, or use of a recombinant protein immunogen in the priming injection and use of a modified vaccinia virus vector encoding the same protein immunogen in the one or more boosting injections.

Viruses

Methods and systems provided herein can be applicable to manufacturing a variety of different viruses, e.g., oncolytic viruses, e.g., recombinant oncolytic viruses. In some cases, the methods and systems provided herein can be applicable to manufacturing vaccinia viruses, e.g., recombinant vaccinia viruses.

Exemplary oncolytic viruses that the methods and system provided herein are applicable to include measles virus, poliovirus, poxvirus, vaccinia virus, adenovirus, adeno-associated virus, herpes simplex virus, vesicular stomatitis virus, reovirus, Newcastle disease virus, Seneca virus, lentivirus, mengovirus, and myxoma virus. In some embodiments, the modified oncolytic virus can comprise the poxvirus. In certain examples, the oncolytic virus can be a vaccinia virus. In some embodiments, the modified oncolytic virus can be suitable for systemic delivery.

Modified Vaccinia Viruses

As used herein, the term "modified vaccinia virus" or a "recombinant vaccinia virus," can relate to a vaccinia virus that has been modified, for example, by a modification such as introducing viral backbone mutations, to express genes/epitopes of a pathogens (viral, bacterial or parasite pathogens causing infectious diseases), to express genes which increases the T-cell response such as TRIF expression, expression of other upstream and downstream molecules of TRIF pathway. In some embodiments, introducing a viral backbone mutation comprises a complete deletion or a partial deletion of one or more virulence genes, or substitutions with one or more viral virulence genes (non-limiting examples include genes that are known to inhibit cytokines involved in the Th1 immune response, or in innate immune signaling, or inhibitors of other components of the immune response, or with vaccinia virulence genes exchanged with more or less potent genes of equivalent function from other poxviruses).

Modified vaccinia viruses of this disclosure can, in some embodiments, be selected from the group consisting of: a wild type vaccinia virus strain and an attenuated vaccinia virus strains. Nonlimiting examples of vaccinia virus strains can include a Western Reserve strain of vaccinia virus (ATCC VR-1354), a thymidine kinase negative Western Reserve vaccinia virus, a Copenhagen strain, an IHD strain, a Wyeth (NYCBOH) strain (ATCC VR-1536), a Tian Tan strain, a Lister strain, an NYVAC strain, a modified vaccinia virus Ankara (MVA) (ATCC VR-1508 or ATCC VR-1566), a USSR strain, an ACAM2000 strain, a Paris strain, a Bern strain, a Temple of Heaven strain, a Dairen strain, an EM-63 strain, an Evans strain, a King strain, a Patwadangar strain, or a Tash Kent strain.

In some embodiments, to develop a modified oncolytic vaccinia virus showing an enhanced systemic delivery and an immune remodeling of tumor microenvironment to enhance T-cell function and differentiation, the Western reserve strain of vaccinia virus was modified by deleting the two non-essential regions in the genome and addition of foreign genomes to express a fusion protein and a chemokine receptor. The loci in the viral backbone of vaccinia virus from where the non-essential genome was deleted was also engineered to receive the foreign genomes.

Modifications to the Vaccinia Virus Backbone

Figure 1:
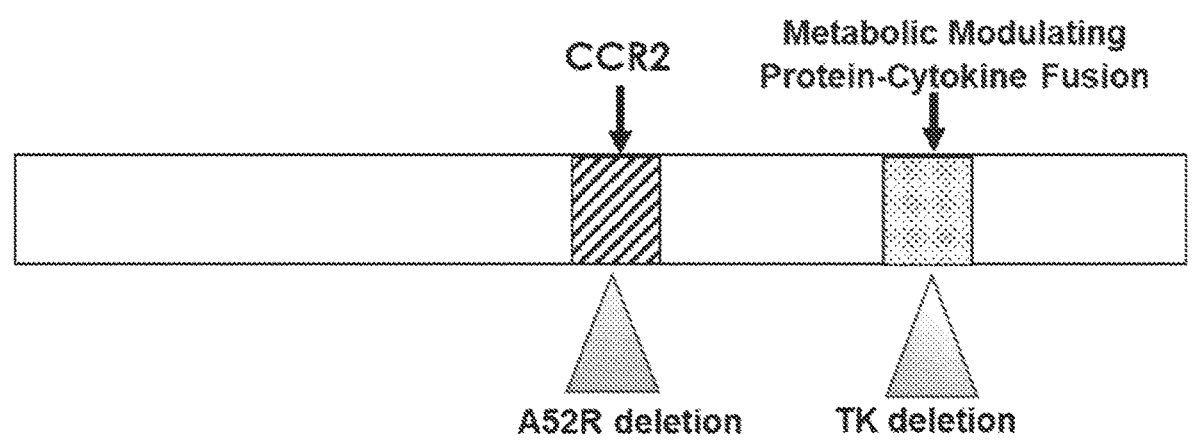

The regions deleted and the foreign genes added at the respective loci are detailed in FIG. 1. The list of nonessential genes deleted from the viral backbone includes thymidine kinase gene (shown as "TK–") and A52R gene (shown as "A52R–"). Thus, in some embodiments, the modified oncolytic vaccinia virus can comprise a heterologous nucleic acid sequence that exhibits enhanced systemic delivery and an immune remodeling of tumor microenvironment to enhance T-cell function and differentiation. Therefore, the heterologous nucleic acid, in some examples, may encode one or more fusion proteins. The heterologous nucleic acid encoding a peptide or protein can be cloned into the locus of the thymidine kinase (TK) gene of the virus.

The complete deletion of thymidine kinase gene from the viral backbone is well recognized U.S. Food and Drug administration as a known tumor targeting safety modification as it limits viral replication to cells expressing cellular thymidine kinase, which is upregulated in most tumors.

The deletion of A52R gene, an NF-kB inhibitor, from the viral backbone enhances the memory T-cell response resulting in enhanced immune response (Di Pilato M, et al. J Virol 91: e00575-17). The deletion of A52R gene is highly effective as cancer therapy as unlike many other deletions this does not reduce viral replication in-vitro.

Combining the deletions of TK gene and A52R gene in the same vaccinia virus backbone produced a double safety mechanism and a highly effective oncolytic vector.

In some cases, the deletion loci of A52R gene on the vaccinia backbone can be substituted with exogeneous nucleic acid which codes for chemokine receptors. More specifically, the chemokine receptor can be CCR2 receptor which can have a target CCL2 expressed on the tumor. Chemokine receptor expression on the virus leads to in situ cell-based targeted and enhanced systemic delivery.

In some cases, the deletion loci of TK gene on the vaccinia backbone can be substituted with the exogenous nucleic acid which codes for a fusion protein. More specifically, the fusion protein can be Leptin-Interleukin (IL)-2 fusion protein. The Leptin-IL-2 fusion protein increases the activity by targeting Leptin more effectively to T-cells (to increase activity) and regulatory T-cells (to suppress their activity) and away from the stromal leptin receptor in the tumor. Moreover, the fusion of IL-2 with leptin created additional therapeutic activity through co-stimulating IL-2 receptors. The fusion protein further created a large molecule which will be more effectively trapped in the tumor and prevent systemic effects. The structure and features of the fusion protein is described in WO2019148109 (the entire disclosure of which is hereby expressly incorporated by reference herein).

Other Multiple Modifications

Provided herein in some embodiments are vaccines comprising modified vaccinia viruses with insertions, mutations, or deletions in the viral genome (also referred to herein as the viral backbone). The vaccinia viruses are modified or selected to have low toxicity and to accumulate in the target tissue. In some embodiments, the modifications in the viral backbone/viral genome are modifications that render the vaccinia virus non-replicating or comprise a poor replicative capacity. Non-limiting examples of such modifications can include mutations in the following viral genes: A1, A2, VH1, A33, and 17.

In some embodiments, the viral backbone mutation is selected from the group consisting of: a complete or partial deletion of the B15R gene; a complete or partial deletion of the K7R gene; a complete or partial deletion of the B14R gene; a complete or partial deletion of the N1L gene; a complete or partial deletion of the K1L gene; a complete or partial deletion of the M2L gene; a complete or partial deletion of the A49R gene; a complete or partial deletion of the VH1 gene; a complete or partial deletion of A33 gene; a complete or partial deletion of A1; a complete or partial deletion of A2 gene; a complete or partial deletion of 17 gene, and a complete or partial deletion of the A46R gene. As used herein, the reference to a viral gene can be made by reference to the protein encoded by the gene (e.g., A33 gene can mean a gene that codes for the A33 protein).

In some embodiments, the viral backbone mutation, including any combinations of substitution, insertion, and deletion, can result in a sequence with less than 100%, 99%, 98%, 97%, 96%, 95%, 94%, 93%, 92%, 91%, 90% or less sequence homology to the wild-type sequence of the viral gene or a viral protein coded by the gene. The viral gene and protein coded by the same, in some embodiments, is selected from the group consisting of: B15R, K7R, B14R, N1L, K1L, M2L, A49R, VH1, A33, A1, A2, 17, and A46R.

In some embodiments, the viral backbone can comprise 1, 2, 3, 4, 5, or more mutations in the amino acid sequence of the viral protein (e.g., a viral antigen). The viral antigen is in some examples selected from the group consisting of: B15R, K7R, B14R, N1L, K1L, M2L, A49R, VH1, A33, A1, A2, 17, and A46R.

The disclosure provides in some embodiments, modified vaccina viruses containing one more mutation in the genome of the virus (virus back bone) such that the mutation increases the T-cell arm of the immune response. A mutation may be addition, deletion, or substitution of one or more nucleic acid in the viral genome (wild type or attenuated native strains of vaccinia virus).

In non-limiting examples, the mutation can be complete or partial deletion of genes that are known to inhibit cytokines involved in the Th1 immune response. As non-limiting examples, the mutation may be deletion of nucleic acid encoding B8R (interferon gamma (IFN-g) binding proteins); C12L (interleukin-18 (IL-18) binding proteins).

In a further non-limiting example, the mutation can be complete or partial deletion of genes in innate immune signaling. As non-limiting examples, the mutation may be deletion of nucleic acid encoding (B18R (type I interferon (IFN)-binding proteins); A52R (nuclear factor κB (NF-κB) inhibitor proteins); E3L (protein kinase (PKR) inhibitors); C4, C16 (STING pathway inhibitors).

In a further non-limiting example, the mutation can be complete or partial deletion of genes encoding proteins for inhibition of other components of the immune response. As non-limiting examples, the mutation may be a complete or partial deletion of nucleic acid encoding B15, K7, B14, N1, K1, M2, A49, VH1, A46 or combination thereof. The viral backbone mutation may also include substituting the vaccinia virulence genes with mostly potent genes of equivalent function from other poxviruses.

Amino acid sequence variants of the polypeptides of the present disclosure can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids of the polypeptide, as compared to wild-type.

Deletion variants may lack one or more residues of the native or wild-type protein. Individual residues can be deleted or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of an immunoreactive epitope or simply one or more residues. Terminal additions, called fusion proteins, may also be generated.

Substitutional variants typically contain the exchange of one amino acid for another at one or more sites within the protein and may be designed to modulate one or more properties of the polypeptide, with or without the loss of other functions or properties. Substitutions may be conservative, that is, one amino acid is replaced with one of similar shape and charge. Conservative substitutions can include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The vaccinia viruses provided herein contain additional insertions, mutations, deletions, or substitutions in the viral genome. A vaccinia virus of this disclosure may contain one or more additional insertions or partial insertions of exogenous nucleic acids that code for one or more of chemokine receptor, TRIF protein or a functional domain thereof, or one or more of leptin, interleukin-2 (IL2), interleukin-15/interleukin-15Ra (IL15/IL15Ra), interleukin-7 (IL-7), leptin-interleukin fusion protein (e.g., leptin-IL2 fusion protein shown in example 1 as L2). Modifications such as insertion of chemokine receptor can be insertion of wild type and/or mutant type CXCR4, CCR2, CCL2. A vaccinia virus may further contain one or more additional deletions or partial deletions of one or more genes from A52R, B15R, K7R, A46R. N1L, E3L, K1L, M2L, C16, N2R. B8R, B18R, VH1 and a functional domain or fragment or variant thereof, or any combinations thereof. In some examples, a modification comprises an exogenous nucleic acid which codes for a chemokine receptor, such as, a CXC receptor, a CC receptors, a CX3C receptor, a XC receptor, a functional fragment thereof or a variant thereof, or any combinations thereof. Examples of chemokine receptors includes, but are not limited to, CXCR1, CXCR2. CXCR3, CXCR4, CXCR5, CXCR6, CXCR7, CCR1, CCR2, CCR3. CCR4, CCR5, CCR6, CCR7, CCR8, CCR9, CCR10, CX3CR1, XCR1, a functional fragment thereof or a variant thereof, or any combinations thereof. In some instances, the exogenous nucleic acid which codes of the chemokine receptor comprises coding for more than one chemokine receptor. For example, a nucleic acid could encode for a CXCR4 and a CCR2 receptor, a CXCR2 and a CCR3 receptor, a CXCR4 and a CCR10 receptor, or any other combination thereof. In some instances, the exogenous nucleic acid which codes for the chemokine receptor comprises a codon optimized nucleic acid sequence for enhanced expression in a virus, e.g., a codon optimized variant of a human chemokine receptor coding sequence (such as a human CCR2 coding sequence). Non-limiting examples of a nucleic acid encoding a chemokine receptor is provided in SEQ ID NOs: 2 and 3, and in some embodiments, the exogenous nucleic acid encoding chemokine receptor, as described herein can comprise a sequence that is at least about 75%, about 80%, about 85%, about 90%, about 95%, about 96%, about 97%, about 98%, about 99%, or about 100% homologous to the sequence of SEQ ID NO: 2 or SEQ ID NO: 3. In some embodiments, the exogenous nucleic acid encoding a fusion protein as described herein (e.g., a leptin-IL2 fusion protein) comprises a sequence that is at least about 75%, about 80%, about 85%, about 90%, about 95%, about 96%, about 97%, about 98%, about 99%, or about 100% homologous to the sequence of SEQ ID NO: 1.

In some embodiments, the exogenous nucleic acid encoding a fusion protein described herein comprises a leptin polypeptide and an IL-2 polypeptide. In some embodiments, the leptin polypeptide comprises a sequence that is at least about 75%, about 80%, about 85%, about 90%, about 95%, about 96%, about 97%, about 98%, about 99%, or about 100% homologous to the sequence of SEQ ID NO: 4. In some embodiments, the IL-2 polypeptide comprises a sequence that is at least about 75%, about 80%, about 85%, about 90%, about 95%, about 96%, about 97%, about 98%, about 99%, or about 100% homologous to the sequence of SEQ ID NO: 5.

Delivery of Modified Oncolytic Viruses

Provided herein are methods of treating a condition by administering a modified oncolytic vaccinia virus as described herein.

In some embodiments, an amount of a modified oncolytic vaccinia virus of this disclosure administered to a subject can be between about $10^3$ and $10^{12}$ infectious viral particles or plaque forming units (PFU), or between about $10^5$ and $10^{10}$ PFU, or between about $10^5$ and $10^8$ PFU, or between about $10^8$ and $10^{10}$ PFU. In some embodiments, the amount of a modified oncolytic vaccinia virus of this disclosure administered to a subject can be between about $10^3$ and $10^{12}$ viral particles or plaque forming units (PFU), or between about $10^5$ and $10^{10}$ PFU, or between about $10^5$ and $10^8$ PFU, or between about $10^8$ and $10^{10}$ PFU. In some embodiments, a modified oncolytic vaccinia virus of this disclosure can be administered at a dose that can comprise about $10^3$ PFU/dose to about $10^4$ PFU/dose, about $10^4$ PFU/dose to about $10^5$ PFU/dose, about $10^5$ PFU/dose to about $10^6$ PFU/dose, about $10^7$ PFU/dose to about $10^8$ PFU/dose, about $10^9$ PFU/dose to about $10^{10}$ PFU/dose, about $10^{10}$ PFU/dose to about $10^{11}$ PFU/dose, about $10^{11}$ PFU/dose to about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In some embodiments, a modified oncolytic vaccinia virus of this disclosure can be administered at a dose that can comprise about $2\times10^3$ PFU/dose, $3\times10^3$ PFU/dose, $4\times10^3$ PFU/dose, $5\times10^3$ PFU/ dose, $6\times10^3$ PFU/dose, $7\times10^3$ PFU/dose, $8\times10^3$ PFU/dose, $9\times10^3$ PFU/dose, about $10^4$ PFU/dose, about $2\times10^4$ PFU/dose, about $3\times10^4$ PFU/dose, about $4\times10^4$ PFU/dose, about $5\times10^4$ PFU/dose, about $6\times10^4$ PFU/dose, about $7\times10^4$ PFU/dose, about $8\times10^4$ PFU/dose, about $9\times10^4$ PFU/dose, about $10^5$ PFU/dose, $2\times10^5$ PFU/dose, $3\times10^5$ PFU/dose, $4\times10^5$ PFU/dose, $5\times10^5$ PFU/dose, $6\times10^5$ PFU/dose, $7\times10^5$ PFU/dose, $8\times10^5$ PFU/dose, $9\times10^5$ PFU/dose, about $10^6$ PFU/dose, about $2\times10^6$ PFU/dose, about $3\times10^6$ PFU/dose, about $4\times10^6$ PFU/dose, about $5\times10^6$ PFU/dose, about $6\times10^6$ PFU/dose, about $7\times10^6$ PFU/dose, about $8\times10^6$ PFU/dose, about $9\times10^6$ PFU/dose, about $10^7$ PFU/dose, about $2\times10^7$ PFU/dose, about $3\times10^7$ PFU/dose, about $4\times10^7$ PFU/dose, about $5\times10^7$ PFU/dose, about $6\times10^7$ PFU/dose, about $7\times10^7$ PFU/dose, about $8\times10^7$ PFU/dose, about $9\times10^7$ PFU/dose, about $10^8$ PFU/dose, about $2\times10^8$ PFU/dose, about $3\times10^8$ PFU/dose, about $4\times10^8$ PFU/dose, about $5\times10^8$ PFU/dose, about $6\times10^8$ PFU/dose, about $7\times10^8$ PFU/dose, about $8\times10^8$ PFU/dose, about $9\times10^8$ PFU/dose, about $10^9$ PFU/dose, about $2\times10^9$ PFU/dose, about $3\times10^9$ PFU/dose, about $4\times10^9$ PFU/dose, about $5\times10^9$ PFU/dose, about $6\times10^9$ PFU/dose, about $7\times10^9$ PFU/dose, about $8\times10^9$ PFU/dose, about $9\times10^9$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{10}$ PFU/dose, about $2\times10^{10}$ PFU/dose, about $3\times10^{10}$ PFU/dose, about $4\times10^{10}$ PFU/dose, about $5\times10^{10}$ PFU/dose, about $6\times10^{10}$ PFU/dose, about $7\times10^{10}$ PFU/dose, about $8\times10^{10}$ PFU/dose, about $9\times10^{10}$ PFU/dose, about $10^{11}$ PFU/dose, about $2\times10^{11}$ PFU/dose, about $3\times1011$ PFU/dose, about $4\times10^{11}$ PFU/dose, about $5\times10^{11}$ PFU/dose, about $6\times10^{11}$ PFU/dose, about $7\times10^{11}$ PFU/dose, about $8\times10^{11}$ PFU/dose, about $9\times10^{11}$ PFU/dose, or about $10^{12}$ PFU/dose, about $10^{12}$ PFU/dose to about $10^{13}$ PFU/dose, about $10^{13}$ PFU/dose to about $10^{14}$ PFU/dose, or about $10^{14}$ PFU/dose to about $10^{15}$ PFU/dose. In some embodiments, a modified oncolytic vaccinia virus of this disclosure can be administered at a dose that can comprise $5\times10^9$ PFU/dose. In some embodiments, a modified oncolytic vaccinia virus of this disclosure can be administered at a dose that can comprise up to $5\times10^9$ PFU/dose.

In some embodiments, a modified oncolytic vaccinia virus of this disclosure, can be administered at a dose that can comprise about $10^3$ viral particles/dose to about $10^4$ viral particles/dose, about $10^4$ viral particles/dose to about $10^5$ viral particles/dose, about $10^5$ viral particles/dose to about $10^6$ viral particles/dose, about $10^7$ viral particles/dose to about $10^8$ viral particles/dose, about $10^9$ viral particles/dose to about $10^{10}$ viral particles/dose, about $10^{10}$ viral particles/dose to about $10^{11}$ viral particles/dose, about $10^{11}$ viral particles/dose to about $10^{12}$ viral particles/dose, about $10^{12}$ viral particles/dose to about $10^{13}$ viral particles/dose, about $10^{13}$ viral particles/dose to about $10^{14}$ viral particles/dose, or about $10^{14}$ viral particles/dose to about $10^{15}$ viral particles/dose.

In some embodiments, a modified oncolytic vaccinia virus of this disclosure can be administered at a dose that can comprise about $10^3$ PFU/kg to about $10^4$ PFU/kg, about $10^4$ PFU/kg to about $10^5$ PFU/kg, about $10^5$ PFU/kg to about $10^6$ PFU/kg, about $10^7$ PFU/kg to about $10^8$ PFU/kg, about $10^9$ PFU/kg to about $10^{10}$ PFU/kg, about $10^{10}$ PFU/kg to about $10^{11}$ PFU/kg, about $10^{11}$ PFU/kg to about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In some embodiments, a modified oncolytic vaccinia virus of this disclosure can be administered at a dose that can comprise about $2\times10^3$ PFU/kg, $3\times10^3$ PFU/kg, $4\times10^3$ PFU/kg, $5\times10^3$ PFU/kg, $6\times10^3$ PFU/kg, $7\times10^3$ PFU/kg, $8\times10^3$ PFU/kg, $9\times10^3$ PFU/kg, about $10^4$ PFU/kg, about $2\times10^4$ PFU/kg, about $3\times10^4$ PFU/kg, about $4\times10^4$ PFU/kg, about $5\times10^4$ PFU/kg, about $6\times10^4$ PFU/kg, about $7\times10^4$ PFU/kg, about $8\times10^4$ PFU/kg, about $9\times10^4$ PFU/kg, about $10^5$ PFU/kg, $2\times10^5$ PFU/kg, $3\times10^5$ PFU/kg, $4\times10^5$ PFU/kg, $5\times10^5$ PFU/kg, $6\times10^5$ PFU/kg, $7\times10^5$ PFU/kg, $8\times10^5$ PFU/kg, $9\times10^5$ PFU/kg, about $10^6$ PFU/kg, about $2\times10^6$ PFU/kg, about $3\times10^6$ PFU/kg, about $4\times10^6$ PFU/kg, about $5\times10^6$ PFU/kg, about $6\times10^6$ PFU/kg, about $7\times10^6$ PFU/kg, about $8\times10^6$ PFU/kg, about $9\times10^6$ PFU/kg, about $10^7$ PFU/kg, about $2\times10^7$ PFU/kg, about $3\times10^7$ PFU/kg, about $4\times10^7$ PFU/kg, about $5\times10^7$ PFU/kg, about $6\times10^7$ PFU/kg, about $7\times10^7$ PFU/kg, about $8\times10^7$ PFU/kg, about $9\times10^7$ PFU/kg, about $10^8$ PFU/kg, about $2\times10^8$ PFU/kg, about $3\times10^8$ PFU/kg, about $4\times10^8$ PFU/kg, about $5\times10^8$ PFU/kg, about $6\times10^8$ PFU/kg, about $7\times10^8$ PFU/kg, about $8\times10^8$ PFU/kg, about $9\times10^8$ PFU/kg, about $10^9$ PFU/kg, about $2\times10^9$ PFU/kg, about $3\times10^9$ PFU/kg, about $4\times10^9$ PFU/kg, about $5\times10^9$ PFU/kg, about $6\times10^9$ PFU/kg, about $7\times10^9$ PFU/kg, about $8\times10^9$ PFU/kg, about $9\times10^9$ PFU/kg, about $10^{10}$ PFU/kg, about $2\times10^{10}$ PFU/kg, about $3\times10^{10}$ PFU/kg, about $4\times10^{10}$ PFU/kg, about $5\times10^{10}$ PFU/kg, about $6\times10^{10}$ PFU/kg, about $7\times10^{10}$ PFU/kg, about $8\times10^{10}$ PFU/kg, about $9\times10^{10}$ PFU/kg, about $10^{10}$ PFU/kg, about $2\times10^{10}$ PFU/kg, about $3\times10^{10}$ PFU/kg, about $4\times10^{10}$ PFU/kg, about $5\times10^{10}$ PFU/kg, about $6\times10^{10}$ PFU/kg, about $7\times10^{10}$ PFU/kg, about $8\times10^{10}$ PFU/kg, about $9\times10^{10}$ PFU/kg, about $10^{11}$ PFU/kg, about $2\times10^{11}$ PFU/kg, about $3\times10^{11}$ PFU/kg, about $4\times1011$ PFU/kg, about $5\times10^{11}$ PFU/kg, about $6\times10^{11}$ PFU/kg, about $7\times10^{11}$ PFU/kg, about $8\times1011$ PFU/kg, about $9\times10^{11}$ PFU/kg, or about $10^{12}$ PFU/kg, about $10^{12}$ PFU/kg to about $10^{13}$ PFU/kg, about $10^{13}$ PFU/kg to about $10^{14}$ PFU/kg, or about $10^{14}$ PFU/kg to about $10^{15}$ PFU/kg. In some embodiments, a modified oncolytic vaccinia virus of this disclosure can be administered at a dose that can comprise $5\times10^9$ PFU/kg. In some embodiments, a modified oncolytic vaccinia virus of this disclosure can be administered at a dose that can comprise up to $5\times10^9$ PFU/kg.

In some embodiments, a modified oncolytic vaccinia virus of this disclosure can be administered at a dose that can comprise about $10^3$ viral particles/kg to about $10^4$ viral particles/kg, about 104 viral particles/kg to about $10^5$ viral particles/kg, about $10^5$ viral particles/kg to about $10^6$ viral particles/kg, about $10^7$ viral particles/kg to about $10^8$ viral particles/kg, about $10^9$ viral particles/kg to about $10^{10}$ viral particles/kg, about $10^{10}$ viral particles/kg to about $10^{11}$ viral particles/kg, about $10^{11}$ viral particles/kg to about $10^{12}$ viral particles/kg, about $10^{12}$ viral particles/kg to about $10^{13}$ viral particles/kg, about $10^{13}$ viral particles/kg to about $10^{14}$ viral particles/kg, or about $10^{14}$ viral particles/kg to about $10^{15}$ viral particles/kg.

A liquid dosage form of a modified oncolytic vaccinia virus as described herein can comprise, in certain embodiments, a viral dose of about $10^3$ PFU/mL to about $10^4$ PFU/mL, about $10^4$ PFU/mL to about $10^5$ PFU/mL, about $10^5$ PFU/mL to about $10^6$ PFU/mL, about $10^7$ PFU/mL to about $10^8$ PFU/mL, about $10^9$ PFU/mL to about $10^{10}$ PFU/mL, about $10^{10}$ PFU/mL to about $10^{11}$ PFU/mL, about $10^{11}$ PFU/mL to about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a modified oncolytic vaccinia virus of this disclosure can be administered at a dose that can comprise about $2\times10^3$ PFU/mL, $3\times10^3$ PFU/mL, $4\times10^3$ PFU/mL, $5\times10^3$ PFU/mL, $6\times10^3$ PFU/mL, $7\times10^3$ PFU/mL, $8 \times 10^3$ PFU/mL, $9 \times 10^3$ PFU/mL, about $10^4$ PFU/mL, about $2 \times 10^4$ PFU/mL, about $3 \times 10^4$ PFU/mL, about $4 \times 10^4$ PFU/mL, about $5 \times 10^4$ PFU/mL, about $6 \times 10^4$ PFU/mL, about $7 \times 10^4$ PFU/mL, about $8 \times 10^4$ PFU/mL, about $9) \times 10^4$ PFU/mL, about $10^5$ PFU/mL, $2 \times 10^5$ PFU/mL, $3 \times 10^5$ PFU/mL, $4 \times 10^5$ PFU/mL, $5 \times 10^5$ PFU/mL, $6 \times 10^5$ PFU/mL, $7 \times 10^5$ PFU/mL, $8 \times 10^5$ PFU/mL, $9 \times 10^5$ PFU/mL, about $10^6$ PFU/mL, about $2 \times 10^6$ PFU/mL, about $3 \times 10^6$ PFU/mL, about $4 \times 10^6$ PFU/mL, about $5 \times 10^6$ PFU/mL, about $6 \times 10^6$ PFU/mL, about $7 \times 10^6$ PFU/mL, about $8 \times 10^6$ PFU/mL, about $9) \times 10^6$ PFU/mL, about $10^7$ PFU/mL, about $2 \times 10^7$ PFU/mL, about $3 \times 10^7$ PFU/mL, about $4 \times 10^7$ PFU/mL, about $5 \times 10^7$ PFU/mL, about $6 \times 10^7$ PFU/mL, about $7 \times 10^7$ PFU/mL, about $8 \times 10^7$ PFU/mL, about $9 \times 10^7$ PFU/mL, about $10^8$ PFU/mL, about $2 \times 10^8$ PFU/mL, about $3 \times 10^8$ PFU/mL, about $4 \times 10^8$ PFU/mL, about $5 \times 10^8$ PFU/mL, about $6 \times 10^8$ PFU/mL, about $7 \times 10^8$ PFU/mL, about $8 \times 10^8$ PFU/mL, about $9 \times 10^8$ PFU/mL, about $10^9$ PFU/mL, about $2 \times 10^9$ PFU/mL, about $3 \times 10^9$ PFU/mL, about $4 \times 10^9$ PFU/mL, about $5 \times 10^9$ PFU/mL, about $6 \times 10^9$ PFU/mL, about $7 \times 10^9$ PFU/mL, about $8 \times 10^9$ PFU/mL, about $9 \times 10^9$ PFU/mL, about $10^{10}$ PFU/mL, about $2 \times 10^{10}$ PFU/mL, about $3 \times 10^{10}$ PFU/mL, about $4 \times 10^{10}$ PFU/mL, about $5 \times 10^{10}$ PFU/mL, about $6 \times 10^{10}$ PFU/mL, about $7 \times 10^{10}$ PFU/mL, about $8 \times 10^{10}$ PFU/mL, about $9 \times 10^{10}$ PFU/mL, about $10^{10}$ PFU/mL, about $2 \times 10^{10}$ PFU/mL, about $3 \times 10^{10}$ PFU/mL, about $4 \times 10^{10}$ PFU/mL, about $5 \times 10^{10}$ PFU/mL, about $6 \times 10^{10}$ PFU/mL, about $7 \times 10^{10}$ PFU/mL, about $8 \times 10^{10}$ PFU/mL, about $9) \times 10^{10}$ PFU/mL, about $10^{11}$ PFU/mL, about $2 \times 10^{11}$ PFU/mL, about $3 \times 10^{11}$ PFU/mL, about $4 \times 10^{11}$ PFU/mL, about $5 \times 10^{11}$ PFU/mL, about $6 \times 10^{11}$ PFU/mL, about $7 \times 10^{11}$ PFU/mL, about $8 \times 10^{11}$ PFU/mL, about $9 \times 10^{11}$ PFU/mL, or about $10^{12}$ PFU/mL, about $10^{12}$ PFU/mL to about $10^{13}$ PFU/mL, about $10^{13}$ PFU/mL to about $10^{14}$ PFU/mL, or about $10^{14}$ PFU/mL to about $10^{15}$ PFU/mL. In some embodiments, a modified oncolytic vaccinia virus of this disclosure can be administered at a dose that can comprise $5 \times 10^9$ PFU/mL. In some embodiments, a modified oncolytic vaccinia virus of this disclosure can be administered at a dose that can comprise up to $5 \times 10^9$ PFU/mL.

In some instances, where the modified oncolytic vaccinia virus can be administered by an injection, the dosage can comprise about $10^3$ viral particles per injection, $10^4$ viral particles per injection, $10^5$ viral particles per injection, $10^6$ viral particles per injection, $10^7$ viral particles per injection, $10^8$ viral particles per injection, $10^9$ viral particles per injection, $10^{10}$ viral particles per injection, $10^{11}$ viral particles per injection, $10^{12}$ viral particles per injection, $2 \times 10^{12}$ viral particles per injection, $10^{13}$ viral particles per injection, $10^{14}$ viral particles per injection, or $10^{15}$ viral particles per injection. In further instances, where the modified oncolytic vaccinia virus is administered by an injection, the dosage can comprise about $10^3$ infectious viral particles per injection, $10^4$ infectious viral particles per injection, $10^5$ infectious viral particles per injection, $10^6$ infectious viral particles per injection, $10^7$ infectious viral particles per injection, $10^8$ infectious viral particles per injection, $10^9$ infectious viral particles per injection, $10^{10}$ infectious viral particles per injection, $10^{11}$ infectious viral particles per injection, $10^{12}$ infectious viral particles per injection, $2 \times 10^{12}$ infectious viral particles per injection, $10^{13}$ infectious viral particles per injection, $10^{14}$ infectious viral particles per injection, or $10^{15}$ infectious viral particles per injection. In additional embodiments, a modified oncolytic vaccinia virus of this disclosure can be administered at a dose that can be about $10^3$ Tissue Culture Inhibitor Dose 50% ($TCID_{50}$)/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $10^4$ $TCID_{50}$/kg, $3 \times 10^8$ $TCID_{50}$/kg, $4 \times 10^8$ $TCID_{50}$/kg, $5 \times 10^8$ $TCID_{50}$/kg, $3 \times 10^9$ $TCID_{50}$/kg, $4 \times 10^9$ $TCID_{50}$/kg, $5 \times 10^9$ $TCID_{50}$/kg, $3 \times 10^{10}$ $TCID_{50}$/kg, $4 \times 10^{10}$ $TCID_{50}$/kg, or $4 \times 10^{10}$ $TCID_{50}$/kg. Note that herein $10^x$ is alternatively expressed as 1 eX. In certain embodiments, the modified oncolytic vaccinia virus can be administered in one or more doses. In certain embodiments, the virus can be administered in an amount sufficient to induce oncolysis in at least about 20% of cells in a tumor, in at least about 30% of cells in a tumor, in at least about 40% of cells in a tumor, in at least about 50% of cells in a tumor, in at least about 60% of cells in a tumor, in at least about 70% of cells in a tumor, in at least about 80% of cells in a tumor, or in at least about 90% of cells in a tumor.

In certain embodiments, a single dose of virus can refer to the amount administered to a subject or a tumor over a 1, 2, 5, 10, 15, 20 or 24 hour period. In certain embodiments, the dose can be spread over time or by separate injection. In certain embodiments, multiple doses (e.g., 2, 3, 4, 5, 6 or more doses) of the vaccinia virus can be administered to the subject, for example, where a second treatment can occur within 1, 2, 3, 4, 5, 6, 7 days or weeks of a first treatment. In certain embodiments, multiple doses of the modified oncolytic v can be administered to the subject over a period of 1, 2, 3, 4, 5, 6, 7 or more days or weeks. In certain embodiments, the oncolytic vaccinia virus or the pharmaceutical composition as described herein can be administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the oncolytic vaccinia virus or the pharmaceutical composition as described herein can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In some embodiments of the methods disclosed herein, the oncolytic vaccinia virus or the pharmaceutical composition can be administered, independently, in an initial dose for a first period of time, an intermediate dose for a second period of time, and a high dose for a third period of time. In some embodiments, the initial dose can be lower than the intermediate dose and the intermediate dose can be lower than the high dose. In some embodiments, the first, second, and third periods of time can be, independently, about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. In some embodiments, a modified oncolytic vaccinia virus as described herein can be administered using a prime-boost regimen.

In some examples, the subject can be put on a reduced carbohydrate diet, e.g., a ketogenic diet prior to, concurrent with, and following administration of the modified oncolytic vaccinia virus es or the pharmaceutical composition comprising the same, as described herein, according to any of the methods of treatment described herein. In certain embodiments, the subject can be put on a diet that can comprise consuming less than 500 grams of carbohydrates per day, less than 450 grams of carbohydrates per day, less than 450 grams of carbohydrates per day, less than 400 grams of carbohydrates per day, less than 350 grams of carbohydrates per day, less than 300 grams of carbohydrates per day, less than 250) grams of carbohydrates per day, less than 200 grams of carbohydrates per day, less than 150 grams of carbohydrates per day, less than 100 grams of carbohydrates per day, less than 90 grams of carbohydrates per day, less than 80 grams of carbohydrates per day, less than 70 grams of carbohydrates per day, less than 60 grams of carbohydrates per day, less than 50 grams of carbohydrates per day, less than 40 grams of carbohydrates per day, less than 30 grams of carbohydrates per day, less than 20 grams of carbohydrates per day, less or than 10 grams of carbohydrates per day.

An exemplary method for the delivery of a modified oncolytic vaccinia virus of the present disclosure or a pharmaceutical composition comprising the same, to cancer or tumor cells can be via intratumoral injection. However, alternate methods of administration can also be used, e.g., intravenous, via infusion, parenteral, intravenous, intradermal, intramuscular, transdermal, sublingual, rectal, intraurethral, intravaginal, intranasal, intrathecal, or intraperitoneal. The routes of administration can vary with the location and nature of the tumor. In certain embodiments, the route of administration can be intradental, transdermal, parenteral, intraperitoneal, intravenous, intramuscular, intranasal, subcutaneous, regional (e.g., in the proximity of a tumor, particularly with the vasculature or adjacent vasculature of a tumor), percutaneous, intrathecal, intratracheal, intraperitoneal, intraarterial, intravesical, intratumoral, inhalation, perfusion, by lavage or orally. An injectable dose of the modified oncolytic vaccinia virus can be administered as a bolus injection or as a slow infusion. In certain embodiments, the modified oncolytic vaccinia virus can be administered to the patient from a source implanted in the patient. In certain embodiments, administration of the modified oncolytic vaccinia virus can occur by continuous infusion over a selected period of time. In some instances, an oncolytic vaccinia virus as described herein, or a pharmaceutical composition containing the same can be administered at a therapeutically effective dose by infusion over a period of about 15 mins, about 30 mins, about 45 mins, about 50 mins, about 55 mins, about 60) minutes, about 75 mins, about 90 mins, about 100 mins, or about 120 mins or longer. The modified oncolytic vaccinia virus or the pharmaceutical composition of the present disclosure can be administered as a liquid dosage, wherein the total volume of administration is about 1 mL to about 5 mL, about 5 mL to 10 mL, about 15 mL to about 20 mL, about 25 mL to about 30) mL, about 30 mL to about 50 mL, about 50 mL to about 100 mL, about 100 mL to 150 mL, about 150 mL to about 200 mL, about 200 mL to about 250 mL, about 250 mL to about 300 mL, about 300 mL to about 350 mL, about 350) mL to about 400 mL, about 400 mL to about 450 mL, about 450) mL to 500 mL, about 500 mL to 750 mL, or about 750 mL to 1000 mL.

Combination Therapies

The methods of this disclosure comprise, in some aspects, administering a modified oncolytic virus as disclosed herein or a pharmaceutical composition containing the same, followed by, preceded by or in combination with one or more further therapy. Examples of the further therapy can include, but are not limited to, chemotherapy, radiation, oncolytic viral therapy with an additional virus, treatment with immunomodulatory proteins, an anti-cancer agent, or any combinations thereof. The further therapy can be administered concurrently or sequentially with respect to administration of the modified virus, such as oncolytic vaccinia virus. In certain embodiments, the methods of this disclosure can comprise administering a modified oncolytic virus as disclosed herein, followed by, preceded by, or in combination with one or more anti-cancer agents or cancer therapies. Anti-cancer agents can include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents. In certain embodiments, the cancer therapies can include chemotherapy, biological therapy, radiotherapy, immunotherapy, hormone therapy, anti-vascular therapy, cryotherapy, toxin therapy and/or surgery or combinations thereof. In certain embodiments, the methods of this disclosure can include administering a modified virus, disclosed herein, followed by, preceded by or in combination with an modified oncolytic virus of this disclosure. Combination of the modified oncolytic vaccinia virus with chemotherapy achieves a synergistic effect which is not seen in modified oncolytic viruses that do not comprise the modifications in the modified oncolytic virus. The synergistic effect of the above combination can be advantageously used to lower the dose of chemotherapy, such as Taxol®. Thus, the treatment method disclosed here, with the modified virus, can reduced toxicities associated with chemotherapy, e.g., patients who respond to chemotherapy but suffer side effects at therapeutic doses. The synergistic effect, can, in certain cases, results in a decrease in tumor growth compared to chemotherapy alone or oncolytic vaccinia virus alone. Exemplary decrease in tumor growth can be from about 2% to about 50%, such as about 5%, about 10%, about 20%, about 25%, about 35%, about 45% or about 50%.

In certain embodiments, treatment using a modified oncolytic virus can be used alone or in combination with one or immunomodulatory agents. An immunomodulatory agent can include any compound, molecule, or substance capable of suppressing antiviral immunity associated with a tumor or cancer. In certain embodiments, the immunomodulatory agent can be capable of suppressing innate immunity or adaptive immunity to the modified virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12. GM-CSF. IL-2. IFN3 and IFNγ, and chemokines, such as MIP-1. MCP-1, and IL-8. In certain embodiments, the immunomodulatory agent can include immune checkpoint modulators such as, but not limited to, anti-CTLA4, anti-PD-1, and anti-PD-L1 and TLR agonists (e.g., Poly I: C). In some examples, the immunomodulatory agent can include an immune checkpoint inhibitor, such as an antagonist of PD-1 (e.g., an antagonist antibody that binds to PD-1), an antagonist of PD-L1 (e.g., an antagonist antibody that binds to PD-L1), an antagonist of CTLA-4 (e.g., an antagonist antibody that binds to CTLA-4), an antagonist of A2AR (e.g., an antagonist antibody that binds to A2AR), an antagonist of B7-H3 (e.g., an antagonist antibody that binds to B7-H3), an antagonist of B7-H4 (e.g., an antagonist antibody that binds to B7-H4), an antagonist of BTLA (e.g., an antagonist antibody that binds to BTLA), an antagonist of IDO (e.g., an antagonist antibody that binds to IDO), an antagonist of KIR (e.g., an antagonist antibody that binds to KIR), an antagonist of LAG3 (e.g., an antagonist antibody that binds to LAG3), an antagonist of TIM-3 (e.g., an antagonist antibody that binds to TIM3). In some embodiments, the further therapy can comprise administering an immune checkpoint regulator. In one example, the immune checkpoint regulator can be TGN1412. In one example, the immune checkpoint regulator can be NKTR-214. In one example, the immune checkpoint regulator can be MEDI0562. In one example, the immune checkpoint regulator can be MEDI6469. In one example, the immune checkpoint regulator can be MEDI6383. In one example, the immune checkpoint regulator can be JTX-2011. In one example, the immune checkpoint regulator can be Keytruda (pembrolizumab). In one example, the immune checkpoint regulator can be Opdivo (nivolumab). In one example, the immune checkpoint regulator can be Yervoy (ipilimumab). In one example, the immune checkpoint regulator can be tremelimumab. In one example, the immune checkpoint regulator can be Tecentriq (atezolizumab). In one example, the immune checkpoint regulator can be MGA271. In one example, the immune checkpoint regulator can be indoximod. In one example, the immune checkpoint regulator can be Epacadostat. In one example, the immune checkpoint regulator can be lirilumab. In one example, the immune checkpoint regulator can be BMS-986016. In one example, the immune checkpoint regulator can be MPDL3280A. In one example, the immune checkpoint regulator can be avelumab. In one example, the immune checkpoint regulator can be durvalumab. In one example, the immune checkpoint regulator can be MEDI4736. In one example, the immune checkpoint regulator can be MEDI4737. In one example, the immune checkpoint regulator can be TRX518. In one example, the immune checkpoint regulator can be MK-4166. In one example, the immune checkpoint regulator can be urelumab (BMS-663513). In one example, the immune checkpoint regulator can be PF-05082566 (PF-2566).

In certain examples, where the further therapy is radiation exemplary doses can be 5,000 Rads (50 Gy) to 100,000 Rads (1000 Gy), or 50,000 Rads (500 Gy), or other appropriate doses within the recited ranges. Alternatively, the radiation dose can be about 30 to 60 Gy, about 40 to about 50 Gy, about 40 to 48 Gy, or about 44 Gy, or other appropriate doses within the recited ranges, with the dose determined, example, by means of a dosimetry study as described above. "Gy" as used herein can refer to a unit for a specific absorbed dose of radiation equal to 100 Rads. Gy is the abbreviation for "Gray."

In certain examples, where the further therapy is chemotherapy, exemplary chemotherapeutic agents can include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids). Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BICNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents can include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®, chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine. Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation. Oxaliplatin (Eloxatin®); Temozolomide (Temodar® and Temodal®); Dactinomycin (also known as actinomycin-D. Cosmegen®); Melphalan (also known as L-PAM, L-sarcolysin, and phenylalanine mustard, Alkeran®); Altretamine (also known as hexamethylmelamine (HMM), Hexalen®); Carmustine (BICNU®); Bendamustine (Treanda®); Busulfan (Busulfex®; and Myleran®); Carboplatin (Paraplatin®); Lomustine (also known as CCNU, CeeNU®); Cisplatin (also known as CDDP, Platinol®; and Platinol®-AQ); Chlorambucil (Leukeran®); Cyclophosphamide (Cytoxan®; and Neosar®); Dacarbazine (also known as DTIC, DIC and imidazole carboxamide. DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride. Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids can include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ®; and Velban®); and vinorelbine (Navelbine®).

Exemplary proteasome inhibitors can, but are not limited to, bortezomib (Velcade®); carfilzomib (PX-171-007, (S)-4-Methyl-N-((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoac etamido)-4-phenylbutanamido)-pentanamide); marizomib (NPI-0052); ixazomib citrate (MLN-9708); delanzomib (CEP-18770); and O-Methyl-N-[(2-methyl-5-thiazolyl) carbonyl]-L-seryl-O-methyl-N-[(IS)-2-[(2R)-2-methyl-2-oxiranyl]-2-oxo-1-(phenylmethyl)ethyl]-L-serinamide (ONX-0912).

"In combination with," as used herein, can mean that the modified virus, such as an oncolytic vaccinia virus as described herein or a pharmaceutical composition comprising the same, and the further therapy, such as a further therapy comprising one or more agents are administered to a subject as part of a treatment regimen or plan. In certain embodiments, being used in combination may not require that the modified oncolytic virus and the one or more agents are physically combined prior to administration or that they be administered over the same time frame. For example, and not by way of limitation, the modified oncolytic virus and the one or more agents can be administered concurrently to the subject being treated, or can be administered at the same time or sequentially in any order or at different points in time.

The further therapy can be administered, in various embodiments, in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In certain embodiments, the further therapy is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. The frequency of administration of the further therapy can be, in certain instances, once daily, twice daily, once every week, once every three weeks, once every four weeks (or once a month), once every 8 weeks (or once every 2 months), once every 12 weeks (or once every 3 months), or once every 24 weeks (once every 6 months). In certain embodiments, a method of treating a subject having a cancer can include administering, to the subject, an effective amount of a modified oncolytic virus, e.g., modified vaccinia virus, of this disclosure. In certain embodiments, the methods of this disclosure can further include administering to the subject an effective amount of one or more agents. For example, and not by way of limitation, the agent can be an anti-cancer agent, an immunomodulatory agent, or any combinations thereof, as described above.

Characterization of Modified Vaccinia Virus

As discussed above, in some embodiments, this disclosure provides a vaccine composition comprising a modified vaccinia virus that is non-replicating or poorly replicating.

In some embodiments, in order to determine whether a given virus is replication-competent or replication-defective in a cell type (e.g., in a fibroblast cell line), the cell type is infected with a known amount of the test virus, representing the "input" titer. The input titers are determined prior to assessment of replication properties using permissive cells for the titration of input virus by a method such as the TCID50 method. Virus inoculum are diluted appropriately to obtain the desired input titer. Infections of the cell types of choice are left for a total of about 4 days, after which time viral samples are prepared by lysis of the infected cells. These virus samples are then titrated on CEF indicator cells as described below. This is the "output" titer. A ratio of output to input titer below 1 indicates that the test virus is replication incompetent under the test conditions, whereas a ratio of output to input titer which is equal to or greater than 1 indicates that the test virus is replication competent under the test conditions.

For the TCID50 method, to determine the replication properties of a test virus, cells of choice can be seeded into 6-well-plates at a concentration of about $5 \times 10^5$ cells/well and incubated over night at 37° C., 5% CO2 in appropriate medium, such as DMEM (Gibco, Cat. No. 61965-026) plus 2% FCS. Cell culture medium can be removed, and cells may be incubated with the virus inoculum for one hour at 37° C., 5% CO2 atmosphere. The amount of virus used for each infection of the different cell types can be about $5 \times 10^4$ TCID50. This can be the "Input" titer of virus referred to above. After one hour at 37° C., the inoculum may be removed by aspiration and cells are then washed 3 times with DMEM and finally 1 ml DMEM, 2% FCS is added, and the plates are left to incubate for about 96 hours (4 days) at 37° C., 5% CO2. The infections are stopped by freezing the plates at −80° C. ready for titration analysis. The resulting cell lysate comprising the remainders of the infected cells and the incubation medium is the virus sample to be titrated for determination of the output titer. Thus, the sample contains intracellular as well as extracellular virus.

Titration analysis of virus samples from replication analyses (immunostaining with a vaccinia virus-specific antibody): For titration of viral output titer, CEF cells are seeded on 96-well-plates in RPMI (Gibco, Cat. No. 61870-010), 7% FCS, 1% Antibiotic/Antimycotic (Gibco, Cat. No. 15240-062) at a concentration of $1 \times 10^4$ cells/well and incubated over night at 37° C., 5% CO2. The 6-well plates containing the infection experiments may be frozen/thawed 3 times and dilutions of 10-1 to 10-12 can be prepared using RPMI growth medium. Virus dilutions may be distributed onto test cells in replicates of 8 and incubated for five days at 37° C., 5% CO2 to allow virus replication. Test cells may be fixed (e.g., using acetone/methanol 1:1) for 10 min, air-dried, washed once with washing buffer (PBS/0.05% Tween20) and incubated with polyclonal vaccinia virus-specific antibody (e.g., Quartett Berlin, Cat. No. 9503-2057) at a 1:1000 dilution in incubation buffer (PBS/3% FCS) for one hour at RT. After washing twice with washing buffer, the horseradish peroxidase (HRP)-coupled secondary anti-rabbit IgG antibody (Promega Mannheim, Cat. No. W4011) can be added at a 1:1000 dilution in incubation buffer for one hour at RT. Cells may again be washed twice with washing buffer and incubated with staining solution (3,3', 5,5' tetramethylbenzidine chromogenic substrate (1.2 mM; Seramun Diagnostic GmbH, Catalogue number S-002-5-TMB/) diluted 1:2 with PBS) for 15 min at RT. Plates can be washed once with washing buffer. Using a microscope, the plates can be scored for infected cells which appear purple (Refer to Appendix 3 for scoring sheets). Every well showing purple staining can be marked as positive for viral replication and the titer is calculated using the Spearman-Kaerber method (TCID50 assay). This is the "Output" titer. With values thus obtained for both Input and Output titers, the amplification ratio of Output: Input may be calculated as indicative of the extent of replication of a given virus in a given cell type. Using the above procedure, it may be easily determined whether, and to what extent, a particular virus, is replication competent in the cell line of choice, e.g., human fibroblast cells, chicken fibroblast cells, MRC-5 cells.

Other exemplary methods that can be performed to assess replication capacity of a modified vaccinia virus as described herein can include, a PCR assay using sera from a mammal or a rodent infected with the modified vaccinia virus, a viral plaque assay, or any combinations thereof.

One exemplary method for viral plaque assays is provided herein. Confluent monolayers of susceptible cells in tissue culture flasks are infected with vaccinia virus. After incubation, cytopathic effects (CPE) is observed and can be visualized through formation of a halo or circular clearing the cell monolayer. Cell culture media can be replaced with a solution that increases the viscosity. The replaced solution can include but is not limited to gelatin or carboxymethylcellulose. The susceptible cells include, but are not limited to, HeLa, BS-C-1, HuTK⁻ CEF, or BHK. The viral plaque assays can be visualized by staining with an agent that increases cell contrast by eye or by microscopy. Incubation following infection can be for 4, 5, 6, 7, 8, 9, 10, 11, 12, 24, 36, 48, or more hours before plaque can be observed. The staining agent can be Crystal Violet. The plaques can be at least 0.05 mm in diameter. The virus can be prepared as an inoculum, wherein the inoculum is preparation at different concentrations or dilutions of the stock virus. The dilution of the can be performed using a dilution factor of 10, 100, 1000, 10000, 1000000, 1000000 or more. The virus titer or concentration can be measured as plaque forming units per mL (pfu/mL).

One exemplary method for a PCR based assay is provided herein. Vaccinia virus content can be quantified using qPCR based approaches. To detect the presence of the vaccinia virus genome, qPCR is used to amplify DNA. To detect the presence of the expression products of said vaccinia virus genome, RT-qPCR can be used to amplify RNA. qPCR primers can be designed to amplify a region of the vaccinia virus genome. For RT-qPCR, primers can be designed to detect specific expression products of the vaccinia genome. The RT-qPCR and qPCR primers can be the same or can be different. The region can consist of 5, 10, 100, 200, 500, 1000, 5000, or more continuous base pairs. DNA and RNA can be isolated using methods known by one skilled in the art. For qPCR based approaches, a known standard is used to determine a concentration or titer of the virus present in the input.

Production of viruses can require quantification of the viral content in a virus composition, such as in a vaccine composition comprising a modified vaccinia virus as described herein. Viral quantification can include, but are not limited to, luminescence, fluorescence, protein, or PCR-based assays. Fluorescence-based assays for quantification can use flow cytometry. PCR-based assays for quantification of virus can include PCR based methods. The presence of the viral genome can be quantified and measured in order to determine the amount of virus present in the composition. The virus input can be lysed or inactivated prior to isolation of the nucleic acid genome. Quantification of the virus can be achieved by measurement of protein content. In some cases, the protein content can be measured by chromatographic assays, ELISA, quantitative immunoblots, or other suitable protein quantitation assays. The measured protein can be a microbial pathogenic antigen or a tumor-associated antigen.

Exemplary Embodiments

Provided herein is a modified oncolytic vaccinia virus comprising: (a) an exogenous nucleic acid encoding a fusion protein comprising a metabolic modulating protein or a functional fragment or a variant thereof. (b) an exogenous nucleic acid encoding a chemokine receptor or a functional fragment or a variant thereof, and (c) a genetic modification in the viral backbone. Further provided herein, wherein the exogenous nucleic acid encoding the chemokine receptor comprises a codon optimized variant of the human coding sequence of the chemokine receptor. Further provided herein are modified oncolytic vaccinia viruses, wherein the fusion protein further comprises a cytokine or a functional fragment or a variant thereof. Further provided herein are modified oncolytic vaccinia viruses, wherein the chemokine receptor comprises at least one of: a CXC receptor, a CC receptors, a CX3C receptor, a XC receptor, a functional fragment thereof or a variant thereof, or any combinations thereof. Further provided herein are modified oncolytic vaccinia viruses, wherein the chemokine receptor comprises a least one of: CXCR1, CXCR2, CXCR2, CXCR3, CXCR4, CXCR5, CXCR6, CXCR7, CCR1, CCR2. CCR3, CCR4, CCR5, CCR6, CCR7, CCR8, CCR9, CCR10, CX3CR1, XCR1, a functional fragment thereof or a variant thereof, or any combinations thereof. Further provided herein are modified oncolytic vaccinia viruses, wherein the chemokine receptor comprises the CXC receptor, and wherein the CXC receptor comprises CXCR4. Further provided herein are modified oncolytic vaccinia viruses, wherein the chemokine receptor is CCR2. Further provided herein are modified oncolytic vaccinia viruses, wherein the chemokine receptor comprises a codon optimized CCR2. Further provided herein are modified oncolytic vaccinia viruses, wherein the genetic modification in the viral backbone is a mutation or a deletion of the A52R gene. Further provided herein are modified oncolytic vaccinia viruses, wherein the deletion is a complete or a partial deletion. Further provided herein are modified oncolytic vaccinia viruses, wherein the oncolytic vaccinia virus further comprises a deletion of thymidine kinase gene. Further provided herein are modified oncolytic vaccinia viruses, wherein the vaccinia virus is a Western Reserve strain Vaccinia virus (ATCC VR-1354), a Copenhagen strain, an IHD strain, a Wyeth strain (ATCC VR-1536), a NYCBOH strain, a Tian Tan strain, a Lister strain, an Ankara strain (ATCC VR-1508 or ATCC VR-1566), a USSR strain, an ACAM2000 strain, a Paris strain, a Bern strain, a Temple of Heaven strain, a Dairen strain, an EM-63 strain, an Evans strain, a King strain, a Patwadangar strain, or a Tash Kent strain. Further provided herein are modified oncolytic vaccinia viruses, wherein the exogenous nucleic acid encoding the fusion protein is cloned into the locus of thymidine kinase gene. Further provided herein are modified oncolytic vaccinia viruses, wherein the exogenous nucleic acid encoding the chemokine receptor is cloned into the locus of A52R gene. Further provided herein are modified oncolytic vaccinia viruses, wherein the exogenous nucleic acid encoding the fusion protein comprising a metabolic modulating protein or a functional fragment or a variant thereof comprises a sequence that is at least about 75%, about 80%, about 85%, about 90%, about 95%, about 96%, about 97%, about 98%, about 99%, or about 100% homologous to the sequence of SEQ ID NO: 1. Further provided herein are modified oncolytic vaccinia viruses, wherein the exogenous nucleic acid encoding the chemokine receptor or a functional fragment or a variant thereof comprises a sequence that is at least about 75%, about 80%, about 85%, about 90%, about 95%, about 96%, about 97%, about 98%, about 99%, or about 100% homologous to the sequence of SEQ ID NO: 2 or SEQ ID NO: 3. Further provided herein are modified oncolytic vaccinia viruses further comprising an exogenous nucleic acid encoding a hyaluronidase. Further provided herein are modified oncolytic vaccinia viruses, wherein the hyaluronidase is PH-20 or HysA.

Provided herein is a modified oncolytic vaccinia virus comprising (a) an exogenous nucleic acid encoding a leptin-interleukin (IL)-2 fusion protein; (b) an exogenous nucleic acid encoding CCR2, and (c) a deletion of A52R gene. Further provided herein is the modified oncolytic vaccinia virus wherein the vaccinia virus is Western Reserve strain Vaccinia virus (ATCC VR-1354). Further provided herein is the modified oncolytic vaccinia virus, wherein the oncolytic vaccinia virus further comprises a deletion of a thymidine kinase gene. Further provided herein is the modified oncolytic vaccinia virus, wherein the exogenous nucleic acid encoding the leptin-interleukin (IL)-2 fusion protein is cloned into the locus of the thymidine kinase gene. Further provided herein is the modified oncolytic vaccinia virus, wherein the nucleic acid encoding CCR2 is cloned into the locus of A52R gene. Further provided herein is the modified oncolytic vaccinia virus further comprising a mutation or a deletion of a viral gene selected from the group consisting of: A1, A2, VH1, A33, 17, K7R. B8R, C12L, B15R, B14R, K1L, N1L, M2L, A49R, A46R, E3L, C4, C16, and a functional domain or a fragment or a variant thereof, or any combinations thereof. Further provided herein is the modified oncolytic vaccinia virus further comprising an exogenous nucleic acid coding for at least one of: HMGB1, PIAS3, LIGHT, fractalkine, ITAC, IL15, IL15Ralpha, CCL5, a functional domain or a fragment or a variant thereof, or any combinations thereof.

Provided herein is a pharmaceutical composition comprising a modified oncolytic virus according to the present disclosure. Further provided herein is the pharmaceutical composition further comprising at least one of: a solubilizing agent, an excipient, or a pharmaceutically acceptable carrier. Further provided herein is the pharmaceutical composition, wherein the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combinations thereof. Further provided herein is the pharmaceutical composition, wherein the excipient comprises di-sodium hydrogen phosphate dihydrate, sodium dihydrogen phosphate dihydrate, sodium chloride, myo-inositol, sorbitol, or any combinations thereof. Further provided herein is the pharmaceutical composition that does not comprise a preservative. Further provided herein is the pharmaceutical composition further comprising one or more of a preservative, a diluent, and a carrier. Further provided herein are pharmaceutical compositions further comprising an additional active ingredient or a salt thereof. Further provided herein is the pharmaceutical composition, wherein the solubilizing agent is sterile water. Further provided herein is the pharmaceutical composition further comprising an additional active ingredient, wherein the additional active ingredient is an anti-cancer agent or a further oncolytic virus.

Provided herein is a kit comprising the modified oncolytic vaccinia virus of the present disclosure.

Provided herein is a kit comprising the pharmaceutical composition of the present disclosure. Further provided herein is said kit further comprising at least one of: an anti-cancer agent or an additional oncolytic virus.

Provided herein is a method of enhancing therapeutic effect of a modified oncolytic vaccinia virus upon systemic delivery of the modified oncolytic vaccinia virus to a subject, relative to a systemic administration of a reference vaccinia virus comprising a TK mutation but not the exogenous nucleic acid encoding the fusion protein or the exogenous nucleic acid encoding the chemokine receptor, comprising a systemic administration of a modified oncolytic vaccinia virus according to or a pharmaceutical composition according to the present disclosure.

Provided herein is a method of treatment comprising administering to a subject an oncolytic vaccinia virus according to the present disclosure, or a pharmaceutical composition of the present disclosure, wherein the administering results in an enhanced systemic immune response in the subject, relative to administering to subject a reference oncolytic vaccinia virus that comprises a deletion of a thymine kinase gene (TK−), does not comprise any one of (a) and (b). Further provided herein is said method, wherein the administering is a systemic administration. Further provided herein is said method, wherein the systemic administration comprises at least one of: an oral administration, an intravenous administration, an intranasal administration, a sublingual administration, a rectal administration, a transdermal administration, or any combinations thereof. Further provided herein is said method, wherein the subject has a cancer.

Provided herein is a method of treating a cancer in a subject, said method comprising administering to said subject a therapeutically effective amount of the modified oncolytic vaccinia virus of the present disclosure. Further provided herein is said method of the present disclosure, wherein the cancer is at least one of: a melanoma, a hepatocellular carcinoma, a breast cancer, a lung cancer, a Non-small lung cancer, a peritoneal cancer, a prostate cancer, a bladder cancer, an ovarian cancer, a leukemia, a lymphoma, a renal cell carcinoma, a pancreatic cancer, an epithelial carcinoma, a gastric/GE junction adenocarcinoma, a cervical cancer, a colon carcinoma, a colorectal cancer, a duodenal cancer, a pancreatic adenocarcinoma, an adenoid cystic, a sarcoma, a mesothelioma, a glioblastoma multiforme, a astrocytoma, a multiple myeloma, a prostate carcinoma, a hepatocellular carcinoma, a cholangiocarcinoma, a pancreatic adenocarcinoma, a head and neck squamous cell carcinoma, a cervical squamous-cell carcinoma, an osteosarcoma, an epithelial ovarian carcinoma, an acute lymphoblastic lymphoma, a myeloproliferative neoplasm, or any combinations thereof. Further provided herein is said method of the present disclosure, wherein the modified oncolytic virus, or the pharmaceutical composition is administered at a dosage that comprises about $10^6$ PFU/mL to about $10^{10}$ PFU/mL of the oncolytic vaccinia virus. Further provided herein is said method of the present disclosure, wherein the modified oncolytic virus, or the pharmaceutical composition is administered at a dosage that comprises about $5\times10^9$ PFU/mL of the oncolytic vaccinia virus. Further provided herein is said method of the present disclosure, wherein the modified oncolytic virus, or the pharmaceutical composition is administered, independently, in an initial dose for a first period of time, an intermediate dose for a second period of time, and a high dose for a third period of time. Further provided herein is said method comprising administration of the initial, the intermediate, and the high dose, independently, wherein the initial dose is lower than the intermediate dose and the intermediate dose is lower than the high dose. Further provided herein is said method, wherein the first, second, and third periods of time are each from about 1 week to about 3 weeks. Further provided herein is said method, wherein the modified oncolytic virus, and the pharmaceutical composition independently comprises a liquid dosage form that is administered at a volume of about 1 mL to about 5 mL, about 5 mL to 10 mL, about 15 mL to about 20 mL, about 25 mL to about 30 mL, about 30 mL to about 50 mL, about 50 mL to about 100 mL, about 100 mL to 150 mL, about 150) mL to about 200 mL, about 200 mL to about 250 mL, about 250) mL to about 300 mL, about 300 mL to about 350 mL, about 350) mL to about 400 mL, about 400 mL to about 450) mL, about 450 mL to 500 mL, about 500 mL to 750 mL, or about 750) mL to 1000 mL. Further provided herein is said method, wherein the modified oncolytic virus, the oncolytic vaccinia virus, or a pharmaceutical composition is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein is said method, wherein the modified oncolytic virus, the oncolytic vaccinia virus, or the pharmaceutical composition is administered for a duration of about 1 week, about 2 weeks, about 3 weeks, about 4 weeks, about 6 weeks, about 7 weeks, about 8 weeks, about 9 weeks, about 10, weeks, or about 12 weeks. Further provided herein is said method, wherein the modified oncolytic virus, or the pharmaceutical composition is administered once daily, twice daily, once every week, once every two weeks, or once every three weeks. Further provided herein is said method, wherein the modified oncolytic virus, or the pharmaceutical composition is administered intravenously, intraperitoneally, or by an intratumoral injection. Further provided herein is said method, wherein the modified oncolytic virus, the oncolytic vaccinia virus, or the pharmaceutical composition is administered as a bolus injection or a slow infusion. Further provided herein, is said method, wherein the administration of the modified oncolytic virus, the oncolytic vaccinia virus, or the pharmaceutical composition results in a first peak viral load after about 1 hour to about 3 days and a second peak viral load after about 3 days to about 10 days from administration of a first dose. Further provided herein is said method, comprising administration of a further therapy, wherein the further therapy is administered for a duration of about 1 week, about 2 weeks, about 3 weeks, about 4 weeks, about 6 weeks, about 7 weeks, about 8 weeks, about 9 weeks, about 10, weeks, or about 12 weeks. Further provided herein is said method, wherein the further therapy is administered once daily, once every week, once every two weeks, or once every three weeks. Further provided herein is said method, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein is said method, wherein the further therapy is administered for a duration of about 1 week, about 2 week, about 3 weeks, about 4 weeks, about 6 weeks, about 7 weeks, about 8 weeks, about 9 weeks, about 10, weeks, or about 12 weeks. Further provided herein is said method, wherein the further therapy is administered once daily, once every week, once every two weeks, or once every three weeks. Further provided herein is said method, wherein the further therapy is administered in a liquid dosage form, a solid dosage form, an inhalable dosage form, an intranasal dosage form, a liposomal formulation, a dosage form comprising nanoparticles, a dosage form comprising microparticles, a polymeric dosage form, or any combinations thereof. Further provided herein is said method, wherein the further therapy is administered orally, intravenously, by an intratumoral injection, or by radiation. Further provided herein is said method, wherein the subject is human. Further provide herein is said method, wherein prior to administration of the modified oncolytic virus, the oncolytic vaccinia virus, or the pharmaceutical composition the subject has been diagnosed with a cancer. Further provided herein is said method, wherein prior to administration of the modified oncolytic virus, the oncolytic vaccinia virus, or the pharmaceutical composition or the further therapy the subject has been diagnosed with a cancer. Further provided herein is said method, wherein the further therapy comprises chemotherapy, radiation, oncolytic viral therapy with an additional virus, treatment with immunomodulatory proteins, a CAR T cellular therapy, an anti-cancer agent, or any combinations thereof. Further provided herein is said method, wherein the further therapy comprises administration of an immunomodulatory agent comprising anti-CD33 antibody and variable region thereof, an anti-CD11b antibody and variable region thereof, a COX2 inhibitor, a cytokine, a chemokine, an anti-CTLA4 antibody or an antigen binding fragment thereof, an anti-PD-1 antibody or an antigen binding fragment thereof, an anti-PD-L1 antibody or an antigen binding fragment thereof, or a TLR agonist. Further provided herein is said method comprising administration of the further therapy, wherein the further therapy comprises administration of the anti-cancer agent, wherein the anti-cancer agent is a chemotherapeutic agent.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

For a better understanding of the present disclosure and of its many advantages, the following examples are given by way of illustration and without limiting the scope of this disclosure.

Example 1: Exemplary Modified Vaccinia Virus Modified to Delete A52R and TK Genes and Inserting CCR2 and Leptin-IL-2 Shows Enhanced Therapeutic Effect and Systemic Delivery in LLC Tumor Models The aim of this study was to explore the therapeutic effect and systemic delivery of a modified vaccinia virus as described herein. A modification was introduced in the genome of the Western reserve strains of Vaccinia Virus (WR) by deleting the A52R gene and Thymidine Kinase (TK) gene and inserting the exogenous nucleic acid encoding CCR2 and exogenous nucleic acid encoding Leptin-Interleukin (IL)-2 fusion protein (referred to herein as WR.Tk-.A52R-.CCR2.Leptin-IL2; also abbreviated as "MMC").

Figure 2B:
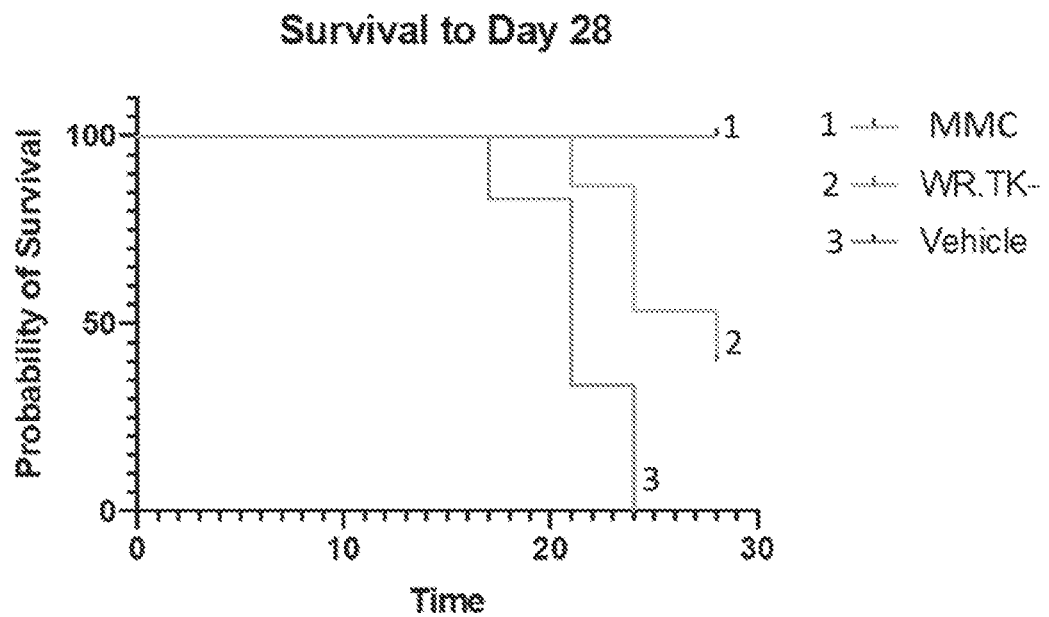
Figure 2C:
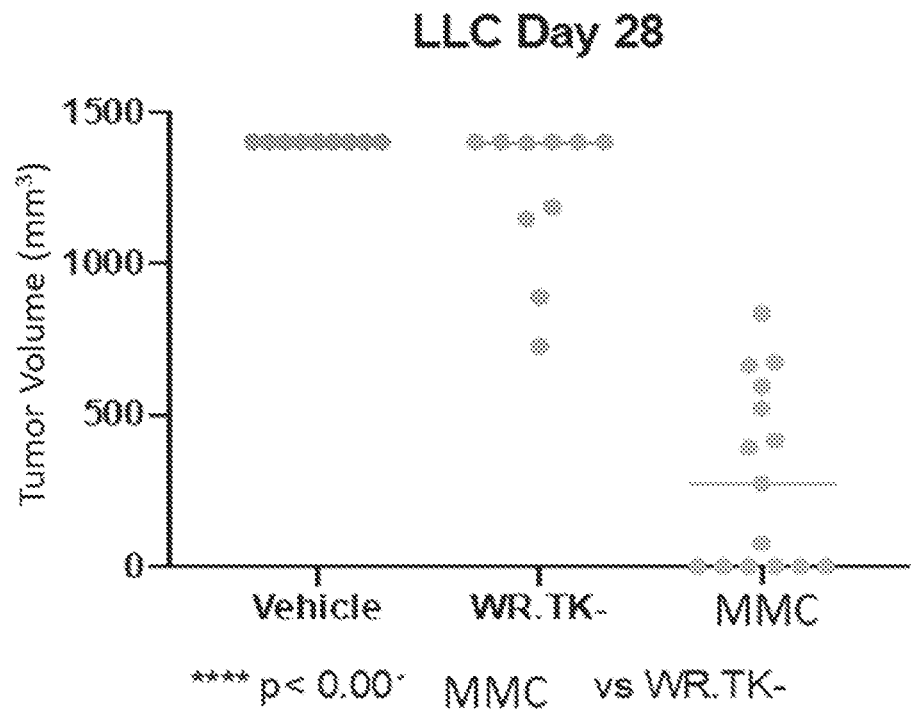

One study was performed in LLC Tumor models for comparing the example modified vaccinia virus with a reference virus that was a Western Reserve strain of vaccinia virus with TK deletion (referred to as WR.TK-) and a vehicle (buffered saline) as control. A dose of $2\times10^7$ PFU was administered intravenously to treat mice (C57/B6) implanted subcutaneously with LLC tumors on days 0) and 3 when tumors reached a size of 50-100 $MM^3$ [results shown in FIG. 2A, FIG. 2B and FIG. 2C]. It was noted that the example modified vaccinia virus administered intravenously led to a significant delay in tumor volume growth as shown in FIG. 2A, as compared to control and the reference virus. Further, FIG. 2B also showed that the probability of survival of mouse was also significantly improved by the administration of the example modified vaccinia virus. The result shows an enhanced therapeutic effect of the example modified vaccinia virus. Additionally, the tumor volumes were measured 28 days after the virus administration for each group receiving the example modified vaccinia virus, or the reference virus, which was the WR.TK- virus, or a control [FIG. 2C]. The results shown in FIGS. 2A, 2B and 2C display a significant enhancement in the therapeutic activity with administration of the example modified vaccinia virus.

Figure 2D:
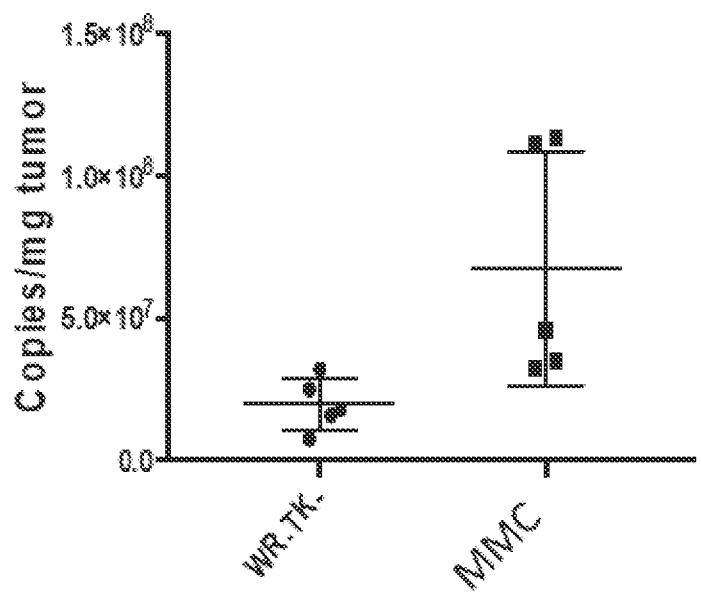

Another study was performed in LLC Tumor models to compare the systemic delivery to tumor of the example modified vaccinia virus with the reference virus (WR.TK- vaccinia virus strain). A dose of $1\times10^7$ PFU was administered intravenously to mice (C57/B6) with subcutaneously implanted LLC tumors. Tumors were harvested 24 hours after IV delivery, and the number of viral genomes per milligram of tumor quantified by qPCR [FIG. 2D]. The results as shown in FIG. 2D indicates a significantly enhanced systemic delivery of the example modified vaccinia virus compared to the reference, the WR. TK-virus.

The above example clearly indicates that the example modified vaccinia virus shows a significantly enhanced therapeutic activity for tumors and high systemic delivery to tumor sites.

Example 2—Exemplary Modified Vaccinia Virus of this Disclosure Shows Enhanced Therapeutic Effect and Systemic Delivery in Pre-Immunized Mice in LLC Tumor Models The aim of this study was to explore the therapeutic effect and systemic delivery of an exemplary modified vaccinia virus according to this disclosure in pre-immunized mice as compared to non-immunized mice.

In this study a C57/B6 mice bearing subcutaneous LLC tumors was used. One group of mice was administered an immunization of a reference virus, which was the vaccinia virus strain WR.TK-, at a dose of $1\times10^6$ PFU, through one injection 30 days prior to tumor implant (labeled as "MMC immunized" in FIG. 3A) and the other group was not immunized (labeled as "MMC" in FIG. 3A).

Figure 3A:
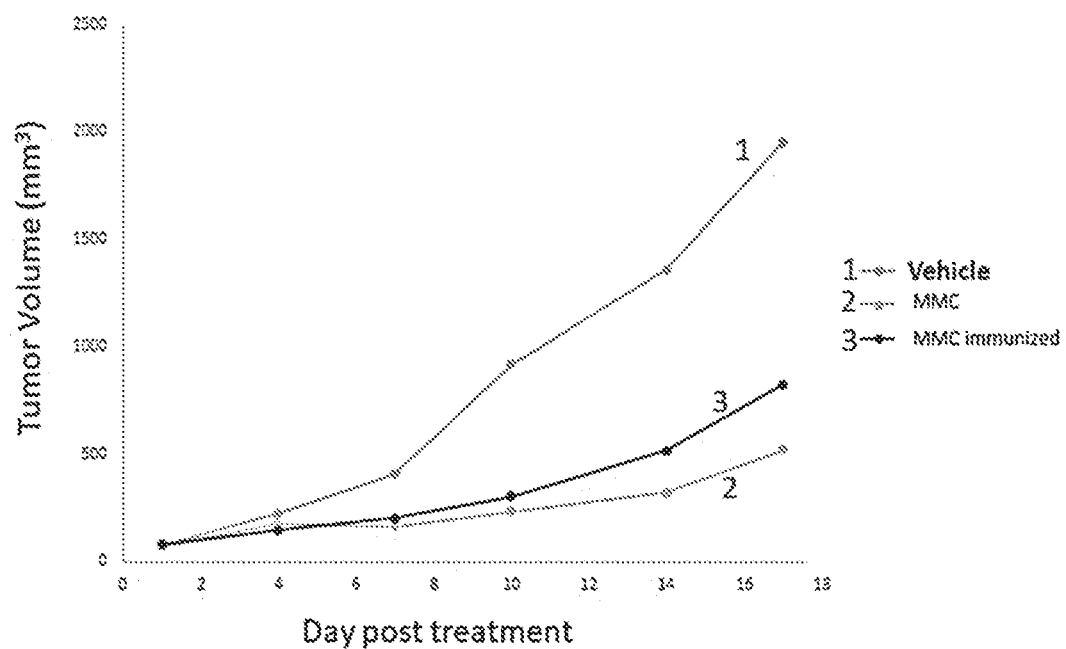
FIG. 3A-3B show exemplary modified vaccinia virus (abbreviated as "MMC") shows enhanced therapeutic effect and systemic delivery in pre-immunized mice in LLC tumor models.

Two intravenous injections of either virus were given to the mice (2 doses of $1\times10^7$ PFU/mL, 3 days apart) when tumors had reached 50-100 $mm^3$, approximately 10 days after implantation. The results of average tumor volume studied is shown in FIG. 3A. The results indicate that the example modified vaccinia virus displayed a good therapeutic activity in the tumors in both immunized and non-immunized mice, compared to the mice administered a vehicle.

Figure 3B:
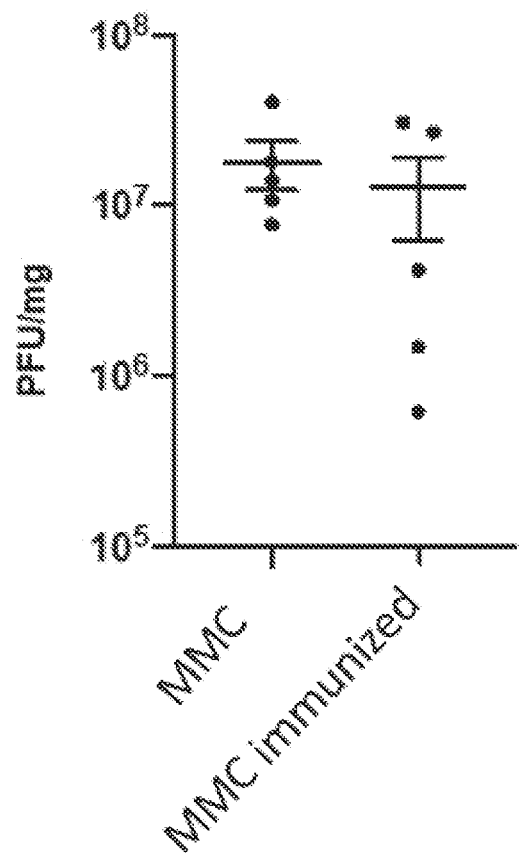

In another study LLC Tumor models was studied to compare the systemic delivery to tumor for the example modified vaccinia virus immunized and un-immunized mice. Two groups of C57/B6 mice bearing subcutaneous tumor were selected. One group administered an immunization of a reference virus, which was the vaccinia virus strain WR.TK-, at a dose of $1\times10^6$ PFU, with one injection 30 days prior to tumor implant and the other group was naive mice bearing subcutaneous LLC tumors, and the other group was not immunized. A dose of $1\times10^7$ PFU was administered intravenously to both groups and tumors were harvested 24 hours after IV delivery. The number of viral genomes per milligram of tumor quantified by qPCR was studied [FIG. 3B]. The results as shown in FIG. 3B indicate good systemic delivery of the example modified vaccinia virus in both the pre-immunized ("MMC immunized") and non-immunized ("MMC") groups.

The above studies suggest the example modified vaccinia virus shows enhanced delivery and therapeutic efficacy both with and without pre-immunization, relative to control viruses.

Example 3—Exemplary Modified Vaccinia Virus of this Disclosure Shows Enhanced Therapeutic Effect in Renca Tumor Models The aim of this study was to explore the therapeutic effect of an example modified vaccinia virus according to the present disclosure (comprising modifications as described in the previous example) in the RENCA tumor models.

Figure 4:
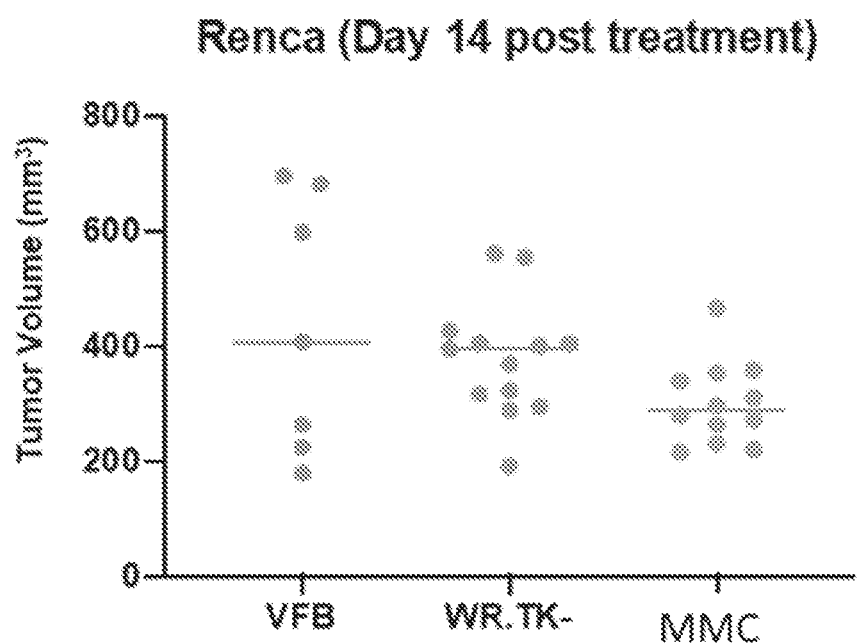
FIG. 4 shows exemplary modified vaccinia virus (abbreviated as "MMC") shows enhanced therapeutic effect in RENCA tumor models.

The study was performed in RENCA Tumor models for comparing the therapeutic activity of the example modified vaccinia virus with the reference virus, which was a Western Reserve strain of vaccinia virus with TK deletion (referred to as WR.TK-), and a vehicle (buffered saline) as control. A dose of $2\times10^7$ PFU of either of the virus or the control was administered intravenously to treat BALB/c mice implanted with subcutaneous RENCA tumors when tumors reached a size of 50-100 $MM^3$ [FIG. 4]. The result for the individual mouse tumor sizes at day 14 after first treatment are shown in FIG. 4. The results in FIG. 4 showed that the example modified vaccinia virus, administered intravenously, resulted in significantly smaller tumor sizes as compared to the reference WR.TK- strain of vaccinia virus and the control.

Example 4—a Biodistribution Study of the Exemplary Modified Vaccinia Virus of this Disclosure Shows Higher Tumor Selectivity a Low Accumulation in Normal Tissues The aim of this study was to study the biodistribution of the example modified vaccinia virus (labeled as NT428N in FIG. 5A and FIG. 5B, comprising modifications as described above in Example 1) as compared to a reference virus (WR.TK-A52R-) vaccinia virus strains (shown as NT202N in FIG. 5A and FIG. 5B) in tumors as compared to all other tissues in LLC Tumor models.

In this study, the example modified vaccinia virus (NT428N) or a vaccinia virus with deletion of TK and A52R genes without expressing CCR2 or Leptin (control virus referred as NT202N) were delivered at a dose of 1×10⁷ PFU via tail vein to two groups of mice. Once group of mice was C57/B6 mice with no tumor [FIG. 5A] and the other group was C57/B6 mice bearing subcutaneous LLC tumors [FIG. 5B]. The mice were sacrificed at 72 hours after the delivery and organs (liver, spleen, brain, heart, kidney, GI tract, bone marrow, lungs, and tumor) were collected and a viral genome was titled by qPCR for no tumor and LLC tumor groups [FIG. 5A and FIG. 5B]. Subsequently, the mice were sacrificed at 10 days after delivery and organs (liver, spleen, brain, heart, kidney, GI tract, bone marrow, lungs, and tumor) were collected for H&E staining. The H&E stains were run, and a full pathology report was obtained [Table 1].

Figure 5A:
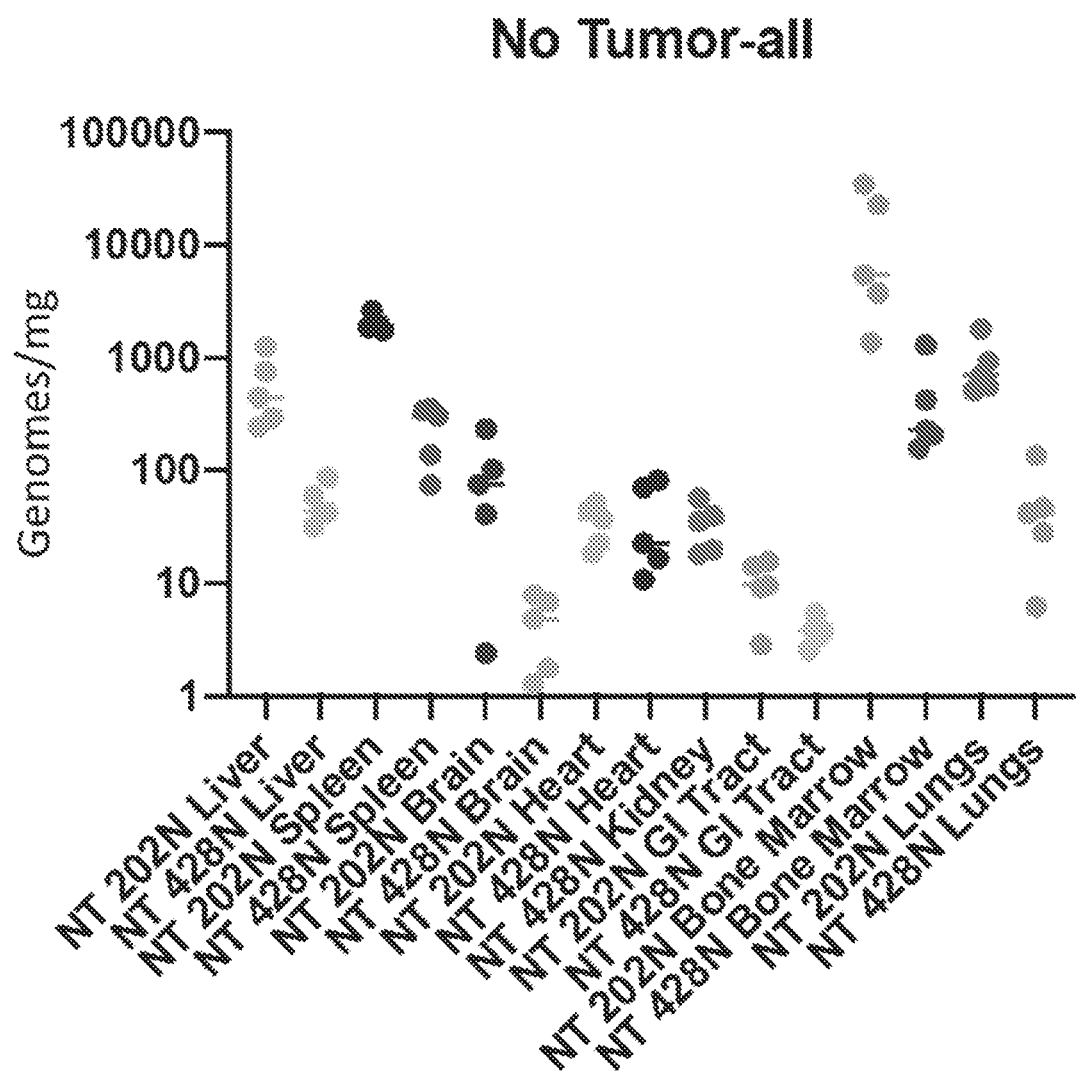
FIG. 5A-5B show a biodistribution study of an exemplary modified vaccinia virus (abbreviated as "NT428N") which shows a higher tumor selectivity a low accumulation in normal tissues.
Figure 5B:
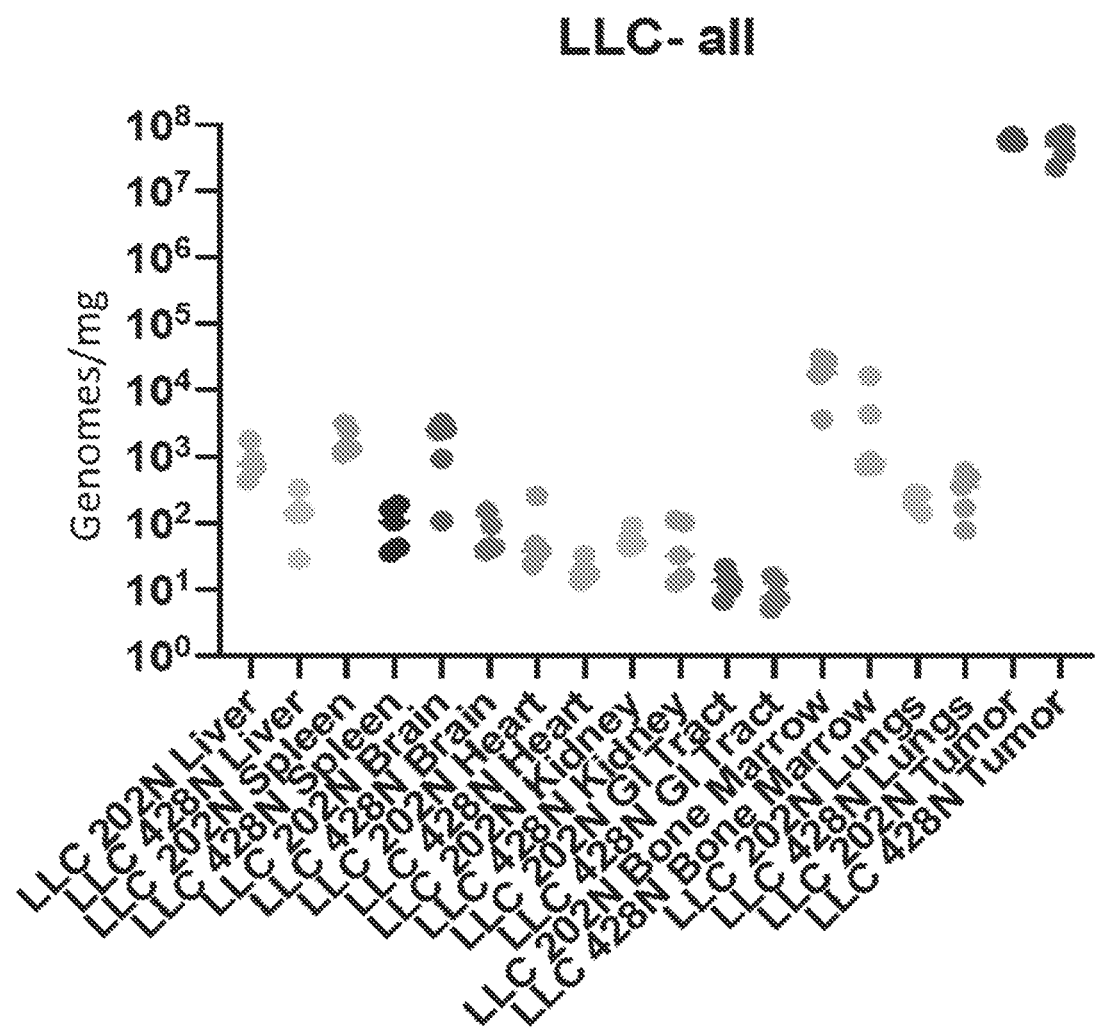

The biodistribution study of FIG. 5A and FIG. 5B show that the example modified vaccinia virus (NT428N) showed a lower titer in all tissues as compared to the control virus (NT202N) and no tissue showed an increase in viral load when CCR2 was expressed. In tumor bearing mice, viral genome in the tumor was significantly higher than any other tissue or organs.

The pathology study in Table 1 shows that the example modified vaccinia virus was well tolerated and would be expected to be safer than similar viruses currently being used in a clinical setting.

TABLE 1

Pathology report at 10 days post treatment

| ORGANS | REPORT |
|---|---|
| Brain | No significant findings |
| Heart | One mouse (of 6) in the control virus (202) groups displayed focal myocardial degeneration; none seen in the NT428N groups |
| Lungs | No significant findings |
| Liver | Some fatty change and microvesicular lipidosis in all viral treatment groups, not increased with NT428N. No change in AST/ALT seen in blood. |
| Kidney | No significant findings |
| Spleen | Extramedullary hematopoiesis and lymphoid hyperplasia in LLC + NT202N group; Not seen with LLC + NT428N. |
| GI Tract | No significant findings |
| Tumor | Necrosis and inflammation were seen with both virus treatments but had the highest mean score for LLC + NT428N. Mitotic rate was also assessed but was not possible in LLC + NT428N group as not enough live tumor cells remained, thereby indicating that the NT428N virus was more effective in destroying tumor cells relative to the control virus NT202N. |

```
SEQUENCES
(leptin-IL2 fusion- nucleic acid sequence)
                                         SEQ ID NO: 1
ATGCATTGGGGAACCCTGTGCGGATTCTTGTGGCTTTGGCCCTATCTTTTCTATGT

CCAAGCTGTGCCCATCCAAAAAGTCCAAGATGACACCAAAACCCTCATCAAGAC

AATTGTCACCAGGATCAATGACATTTCACACACGCAGTCAGTCTCCTCCAAACAG

AAAGTCACCGGTTTGGACTTCATTCCTGGGCTCCACCCCATCCTGACCTTATCCA

AGATGGACCAGACACTGGCAGTCTACCAACAGATCCTCACCAGTATGCCTTCCA

GAAACGTGATCCAAATATCCAACGACCTGGAGAACCTCCGGGATCTTCTTCACGT

GCTGGCCTTCTCTAAGAGCTGCCACTTGCCCTGGGCCAGTGGCCTGGAGACCTTG

GACAGCCTGGGGGGTGTCCTGGAAGCTTCAGGCTACTCCACAGAGGTGGTGGCC

CTGAGCAGGCTGCAGGGGTCTCTGCAGGACATGCTGTGGCAGCTGGACCTCAGC

CCTGGGTGCGGAGGTGGCGGATCCGGCGGAGGTGGCTCAGGTGGCGGTGGATCA

GGAGGAGGTGGATCAGCTAGCGCACCTACTTCAAGTTCTACAAAGAAAACACAG

CTACAACTGGAGCATTTACTGCTGGATTTACAGATGATTTTGAATGGAATTAATA

ATTACAAGAATCCCAAACTCACCAGGATGCTCACATTTAAGTTTTACATGCCCAA

GAAGGCCACAGAACTGAAACATCTTCAGTGTCTAGAAGAAGAACTCAAACCTCT

GGAGGAAGTGCTAAATTTAGCTCAAAGCAAAAACTTTCACTTAAGACCCAGGGA

CTTAATCAGCAATATCAACGTAATAGTTCTGGAACTAAAGGGATCTGAAACAAC

ATTCATGTGTGAATATGCTGATGAGACAGCAACCATTGTAGAATTTCTGAACAGA

TGGATTACCTTTTGTCAAAGCATCATCTCAACACTGACTTGA (Nucleic acid sequence that encodes CCR2, variant 467):
                                         SEQ ID NO: 2
ATGCTGTCCACATCTCGTTCTCGGTTTATCAGAAATACCAACGAGAGCGGTGAAG

AAGTCACCACCTTTTTTGATTATGATTACGGTGCTCCCTGTCATAAATTTGACGTG

AAGCAAATTGGGGCCCAACTCCTGCCTCCGCTCTACTCGCTGGTGTTCATCTTTG
```

-continued

```
GTTTTGTGGGCAACATGCTGGTCGTCCTCATCTTAATAAACTGCAAAAAGCTGAA

GTGCTTGACTGACATTTACCTGCTCAACCTGGCCATCTCTGATCTGCTTTTTCTTA

TTACTCTCCCATTGTGGGCTCACTCTGCTGCAAATGAGTGGGTCTTTGGGAATGC

AATGTGCAAATTATTCACAGGGCTGTATCACATCGGTTATTTTGGCGGAATCTTC

TTCATCATCCTCCTGACAATCGATAGATACCTGGCTATTGTCCATGCTGTGTTTGC

TTTAAAAGCCAGGACGGTCACCTTTGGGGTGGTGACAAGTGTGATCACCTGGTTG

GTGGCTGTGTTTGCTTCTGTCCCAGGAATCATCTTTACTAAATGCCAGAAAGAAG

ATTCTGTTTATGTCTGTGGCCCTTATTTTCCACGAGGATGGAATAATTTCCACACA

ATAATGAGGAACATTTTGGGGCTGGTCCTGCCGCTGCTCATCATGGTCATCTGCT

ACTCGGGAATCCTGAAAACCCTGCTTCGGTGTCGAAACGAGAAGAAGAGGCATA

GGGCAGTGAGAGTCATCTTCACCATCATGATTGTTTACTTTCTCTTCTGGACTCCC

TATAATATTGTCATTCTCCTGAACACCTTCCAGGAATTCTTCGGCCTGAGTAACTG

TGAAAGCACCAGTCAACTGGACCAAGCCACGCAGGTGACAGAGACTCTTGGGAT

GACTCACTGCTGCATCAATCCCATCATCTATGCCTTCGTTGGGGAGAAGTTCAGA

AGCCTTTTTCACATAGCTCTTGGCTGTAGGATTGCCCCACTCCAAAAACCAGTGT

GTGGAGGTCCAGGAGTGAGACCAGGAAAGAATGTGAAAGTGACTACACAAGGA

CTCCTCGATGGTCGTGGAAAAGGAAAGTCAATTGGCAGAGCCCCTGAAGCCAGT

CTTCAGGACAAAGAAGGAGCCTAG (Nucleic acid sequence that encodes CCR2, variant 502):
                                                 SEQ ID NO: 3
ATGCTGTCCACATCTCGTTCTCGGTTTATCAGAAATACCAACGAGAGCGGTGAAG

AAGTCACCACCTTTTTTGATTATGATTACGGTGCTCCCTGTCATAAATTTGACGTG

AAGCAAATTGGGGCCCAACTCCTGCCTCCGCTCTACTCGCTGGTGTTCATCTTTG

GTTTTGTGGGCAACATGCTGGTCGTCCTCATCTTAATAAACTGCAAAAAGCTGAA

GTGCTTGACTGACATTTACCTGCTCAACCTGGCCATCTCTGATCTGCTgTTcCTTAT

TACTCTCCCATTGTGGGCTCACTCTGCTGCAAATGAGTGGGTCTTTGGGAATGCA

ATGTGCAAATTATTCACAGGGCTGTATCACATCGGTTATTTTGGCGGAATCTTCTT

CATCATCCTCCTGACAATCGATAGATACCTGGCTATTGTCCATGCTGTGTTTGCTT

TAAAAGCCAGGACGGTCACCTTTGGGGTGGTGACAAGTGTGATCACCTGGTTGG

TGGCTGTGTTTGCTTCTGTCCCAGGAATCATCTTTACTAAATGCCAGAAAGAAGA

TTCTGTTTATGTCTGTGGCCCTTATTTTCCACGAGGATGGAATAATTTCCACACAA

TAATGAGGAACATTTTGGGGCTGGTCCTGCCGCTGCTCATCATGGTCATCTGCTA

CTCGGGAATCCTGAAAACCCTGCTTCGGTGTCGAAACGAGAAGAAGAGGCATAG

GGCAGTGAGAGTCATCTTCACCATCATGATTGTTTACTTTCTCTTCTGGACTCCCT

ATAATATTGTCATTCTCCTGAACACCTTCCAGGAATTCTTCGGCCTGAGTAACTGT

GAAAGCACCAGTCAACTGGACCAAGCCACGCAGGTGACAGAGACTCTTGGGATG

ACTCACTGCTGCATCAATCCCATCATCTATGCCTTCGTTGGGGAGAAGTTCAGAA

GCCTTTTTCACATAGCTCTTGGCTGTAGGATTGCCCCACTCCAAAAACCAGTGTG
```

-continued
```
TGGAGGTCCAGGAGTGAGACCAGGAAAGAATGTGAAAGTGACTACACAAGGAC

TCCTCGATGGTCGTGGAAAAGGAAAGTCAATTGGCAGAGCCCCTGAAGCCAGTC

TTCAGGACAAAGAAGGAGCCTAG
```

(Nucleic acid sequence encoding leptin)

SEQ ID NO: 4
```
GTAGGAATCGCAGCGCCAGCGGTTGCAAGGCCCAAGAAGCCCATCCTGGGAAGG

AAAATGCATTGGGGAACCCTGTGCGGATTCTTGTGGCTTTGGCCCTATCTTTTCTA

TGTCCAAGCTGTGCCCATCCAAAAAGTCCAAGATGACACCAAAACCCTCATCAA

GACAATTGTCACCAGGATCAATGACATTTCACACACGCAGTCAGTCTCCTCCAAA

CAGAAAGTCACCGGTTTGGACTTCATTCCTGGGCTCCACCCCATCCTGACCTTAT

CCAAGATGGACCAGACACTGGCAGTCTACCAACAGATCCTCACCAGTATGCCTTC

CAGAAACGTGATCCAAATATCCAACGACCTGGAGAACCTCCGGGATCTTCTTCAC

GTGCTGGCCTTCTCTAAGAGCTGCCACTTGCCCTGGGCCAGTGGCCTGGAGACCT

TGGACAGCCTGGGGGGTGTCCTGGAAGCTTCAGGCTACTCCACAGAGGTGGTGG

CCCTGAGCAGGCTGCAGGGGTCTCTGCAGGACATGCTGTGGCAGCTGGACCTCA

GCCCTGGGTGCTGAGGCCTTGAAGGTCACTCTTCCTGCAAGGACTACGTTAAGGG

AAGGAACTCTGGCTTCCAGGTATCTCCAGGATTGAAGAGCATTGCATGGACACC

CCTTATCCAGGACTCTGTCAATTTCCCTGACTCCTCTAAGCCACTCTTCCAAAGGC

ATAAGACCCTAAGCCTCCTTTTGCTTGAAACCAAAGATATATACACAGGATCCTA

TTCTCACCAGGAAGGGGGTCCACCCAGCAAAGAGTGGGCTGCATCTGGGATTCC

CACCAAGGTCTTCAGCCATCAACAAGAGTTGTCTTGTCCCCTCTTGACCCATCTC

CCCCTCACTGAATGCCTCAATGTGACCAGGGGTGATTTCAGAGAGGGCAGAGGG

GTAGGCAGAGCCTTTGGATGACCAGAACAAGGTTCCCTCTGAGAATTCCAAGGA

GTTCCATGAAGACCACATCCACACACGCAGGAACTCCCAGCAACACAAGCTGGA

AGCACATGTTTATTTATTCTGCATTTTATTCTGGATGGATTTGAAGCAAAGCACCA

GCTTCTCCAGGCTCTTTGGGGTCAGCCAGGGCCAGGGGTCTCCCTGGAGTGCAGT

TTCCAATCCCATAGATGGGTCTGGCTGAGCTGAACCCATTTTGAGTGACTCGAGG

GTTGGGTTCATCTGAGCAAGAGCTGGCAAAGGTGGCTCTCCAGTTAGTTCTCTCG

TAACTGGTTTCATTTCTACTGTGACTGATGTTACATCACAGTGTTTGCAATGGTGT

TGCCCTGAGTGGATCTCCAAGGACCAGGTTATTTTAAAAAGATTTGTTTTGTCAA

GTGTCATATGTAGGTGTCTGCACCCAGGGGTGGGAATGTTTGGGCAGAAGGGA

GAAGGATCTAGAATGTGTTTTCTGAATAACATTTGTGTGGTGGGTTCTTTGGAAG

GAGTGAGATCATTTTCTTATCTTCTGCAATTGCTTAGGATGTTTTTCATGAAAATA

GCTCTTTCAGGGGGGTTGTGAGGCCTGGCCAGGCACCCCCTGGAGAGAAGTTTCT

GGCCCTGGCTGACCCCAAAGAGCCTGGAGAAGCTGATGCTTTGCTTCAAATCCAT

CCAGAATAAAACGCAAAGGGCTGAAAGCCATTTGTTGGGGCAGTGGTAAGCTCT

GGCTTTCTCCGACTGCTAGGGAGTGGTCTTTCCTATCATGGAGTGACGGTCCCAC

ACTGGTGACTGCGATCTTCAGAGCAGGGGTCCTTGGTGTGACCCTCTGAATGGTC

CAGGGTTGATCACACTCTGGGTTTATTACATGGCAGTGTTCCTATTTGGGGCTTGC

ATGCCAAATTGTAGTTCTTGTCTGATTGGCTCACCCAAGCAAGGCCAAAATTACC

AAAAATCTTGGGGGGTTTTTACTCCAGTGGTGAAGAAAACTCCTTTAGCAGGTGG

TCCTGAGACCTGACAAGCACTGCTAGGCGAGTGCCAGGACTCCCCAGGCCAGGC
```

-continued

CACCAGGATGGCCCTTCCCACTGGAGGTCACATTCAGGAAGATGAAAGAGGAGG

TTTGGGGTCTGCCACCATCCTGCTGCTGTGTTTTTGCTATCACACAGTGGGTGGTG

GATCTGTCCAAGGAAACTTGAATCAAAGCAGTTAACTTTAAGACTGAGCACCTG

CTTCATGCTCAGCCCTGACTGGTGCTATAGGCTGGAGAAGCTCACCCAATAAACA

TTAAGATTGAGGCCTGCCCTCAGGGATCTTGCATTCCCAGTGGTCAAACCGCACT

CACCCATGTGCCAAGGTGGGGTATTTACCACAGCAGCTGAACAGCCAAATGCAT

GGTGCAGTTGACAGCAGGTGGGAAATGGTATGAGCTGAGGGGGGCCGTGCCCAG

GGGCCCACAGGGAACCCTGCTTGCACTTTGTAACATGTTTACTTTTCAGGGCATC

TTAGCTTCTATTATAGCCACATCCCTTTGAAACAAGATAACTGAGAATTTAAAAA

TAAGAAAATACATAAGACCATAACAGCCAACAGGTGGCAGGACCAGGACTATA

GCCCAGGTCCTCTGATACCCAGAGCATTACGTGAGCCAGGTAATGAGGGACTGG

AACCAGGGAGACCGAGCGCTTTCTGGAAAAGAGGAGTTTCGAGGTAGAGTTTGA

AGGAGGTGAGGGATGTGAATTGCCTGCAGAGAGAAGCCTGTTTTGTTGGAAGGT

TTGGTGTGTGGAGATGCAGAGGTAAAAGTGTGAGCAGTGAGTTACAGCGAGAGG

CAGAGAAAGAAGAGACAGGAGGGCAAGGGCCATGCTGAAGGGACCTTGAAGGG

TAAAGAAGTTTGATATTAAAGGAGTTAAGAGTAGCAAGTTCTAGAGAAGAGGCT

GGTGCTGTGGCCAGGGTGAGAGCTGCTCTGGAAAATGTGACCCAGATCCTCACA

ACCACCTAATCAGGCTGAGGTGTCTTAAGCCTTTTGCTCACAAAACCTGGCACAA

TGGCTAATTCCCAGAGTGTGAAACTTCCTAAGTATAAATGGTTGTCTGTTTTTGTA

ACTTAAAAAAAAAAAAAAAGTTTGGCCGGGTGCGGTGGCTCACGCCTGTAATC

CCAGCACTTTGGGAGGCCAAGGTGGGGGGATCACAAGGTCACTAGATGGCGAGC

ATCCTGGCCAACATGGTGAAACCCCGTCTCTACTAAAAACACAAAAGTTAGCTG

AGCGTGGTGGCGGGCGCCTGTAGTCCCAGCCACTCGGGAGGCTGAGACAGGAGA

ATCGCTTAAACCTGGGAGGCGGAGAGTACAGTGAGCCAAGATCGCGCCACTGCA

CTCCGGCCTGATGACAGAGCGAGATTCCGTCTTAAAAAAAAAAAAAAAAAAGTT

TGTTTTTAAAAAAATCTAAATAAAATAACTTTGCCCCCTGCAAAAAAAAAAAAA

AAAA (Nucleic acid sequence encoding IL-2) (ENA No. E00257.1)
SEQ ID NO: 5
AATTCTATGGCTCCGACTTCAAGTTCTACCAAGAAGACCCAGCTTCAATTAGAAC

ATTTACTTCTAGATTTACAAATGATTCTGAATGGTATCAACAATTATAAGAATCC

AAAGCTTACTCGTATGTTGACCTTTAAATTCTATATGCCTAAGAAGGCTACTGAA

TTAAAACACCTGCAGTGTTTAGAAGAAGAGCTCAAACCGTTAGAAGAAGTTCTG

AATCTGGCTCAATCTAAAAACTTCCATTTACGTCCACGAGATCTTATCTCTAATAT

TAACGTAATCGTTTTGGAACTTAAAGGATCCGAAACTACCTTCATGTGTGAATAT

GCTGACGAAACCGCTACGATCGTAGAATTTCTTAATCGATGGATTACTTTCTGTC

AATCTATTATCTCTACCTTAACTTGAGTCGACG

The invention claimed is:

1. A modified oncolytic virus comprising:
an exogenous nucleic acid encoding a fusion protein comprising a metabolic modulating protein, wherein the exogenous nucleic acid encoding for the fusion protein comprises:
a region encoding for an IL-2 polypeptide, and
a region encoding for a leptin polypeptide;
an exogenous nucleic acid encoding a chemokine receptor, wherein the chemokine receptor is CCR2; and
a genetic modification in a viral genome of the modified oncolytic virus, wherein the modified oncolytic virus provides for enhanced tumor volume reduction upon systemic delivery to a subject compared to systemic administration of an otherwise identical oncolytic virus not comprising the exogenous nucleic acid encoding the fusion protein.

2. The modified oncolytic virus of claim 1, wherein the exogenous nucleic acid encoding the chemokine receptor comprises a codon optimized variant of a human coding sequence of the chemokine receptor.

3. The modified oncolytic virus of claim 2, wherein the fusion protein further comprises a cytokine.

4. The modified oncolytic virus of claim 3, wherein the genetic modification is a mutation or a deletion of an A52R gene.

5. The modified oncolytic virus of claim 4, wherein the deletion is a complete or a partial deletion.

6. The modified oncolytic virus of claim 5, wherein the oncolytic virus further comprises a deletion of a thymidine kinase gene.

7. The modified oncolytic virus of claim 6, wherein the oncolytic virus comprises measles virus, poliovirus, poxvirus, vaccinia virus, adenovirus, adeno-associated virus, herpes simplex virus, vesicular stomatitis virus, reovirus, Newcastle disease virus, Seneca virus, lentivirus, mengovirus, or myxoma virus.

8. The modified oncolytic virus of claim 7, wherein the oncolytic virus is a poxvirus.

9. The modified oncolytic virus of claim 8, wherein the poxvirus is a vaccinia virus.

10. The modified oncolytic virus of claim 9, wherein the vaccinia virus is a Western Reserve strain Vaccinia virus, a Copenhagen strain, an IHD strain, a Wyeth strain, a NYCBOH strain, a Tian Tan strain, a Lister strain, an Ankara strain, a USSR strain, an ACAM2000 strain, a Paris strain, a Bern strain, a Temple of Heaven strain, a Dairen strain, an EM-63 strain, an Evans strain, a King strain, a Patwadangar strain, or a Tash Kent strain.

11. The modified oncolytic virus of claim 1, wherein the exogenous nucleic acid encoding the fusion protein is cloned into a locus of a thymidine kinase gene.

12. The modified oncolytic virus of claim 1, wherein the exogenous nucleic acid encoding the chemokine receptor is cloned into a locus of an A52R gene.

13. The modified oncolytic virus of claim 12, further comprising an exogenous nucleic acid encoding a hyaluronidase.

14. The modified oncolytic virus of claim 13, further comprising a mutation or a deletion of a viral gene selected from the group consisting of: A1, A2, VH1, A33, 17, K7R, B8R, C12L, B15R, B14R, K1L, N1L, M2L, A49R, A46R, E3L, C4, C16, and a functional domain or a fragment or a variant thereof, or any combinations thereof.

15. The modified oncolytic virus of claim 14, further comprising an exogenous nucleic acid coding for at least one of: HMGB1, PIAS3, LIGHT, fractalkine, ITAC, IL 15, IL15Ralpha, CCL5, a functional domain or a fragment or a variant thereof, or any combinations thereof.

16. The modified oncolytic virus of claim 1, wherein the region encoding for the IL-2 polypeptide comprises a sequence having at least about 75%, about 80%, about 85%, about 90%, about 95%, about 96%, about 97%, about 98%, about 99%, or about 100% identity to the sequence of SEQ ID NO: 5.

17. The modified oncolytic virus of claim 1, wherein the exogenous nucleic acid encoding the fusion protein comprises a sequence having at least about 75%, about 80%, about 85%, about 90%, about 95%, about 96%, about 97%, about 98%, about 99%, or about 100% identity to the sequence of SEQ ID NO: 1.

18. The modified oncolytic virus of claim 1, wherein the exogenous nucleic acid encoding the chemokine receptor comprises a sequence having at least about 75%, about 80%, about 85%, about 90%, about 95%, about 96%, about 97%, about 98%, about 99%, or about 100% identity to the sequence of SEQ ID NO: 2 or SEQ ID NO: 3.

19. A pharmaceutical composition comprising the modified oncolytic virus of claim 1.

20. The pharmaceutical composition of claim 19, further comprising at least one of: a solubilizing agent, an excipient, or a pharmaceutically acceptable carrier.

21. The pharmaceutical composition of claim 20, wherein the excipient comprises one or more of a buffering agent, a stabilizer, an antioxidant, a binder, a diluent, a dispersing agent, a rate controlling agent, a lubricant, a glidant, a disintegrant, a plasticizer, a preservative, or any combinations thereof.

22. The pharmaceutical composition of claim 21, wherein the excipient comprises di-sodium hydrogen phosphate dihydrate, sodium dihydrogen phosphate dihydrate, sodium chloride, myo-inositol, sorbitol, or any combinations thereof.

23. The pharmaceutical composition of claim 22, further comprising one or more of a preservative, a diluent, and a carrier.

24. The pharmaceutical composition of claim 23, further comprising an additional active ingredient or a salt thereof.

25. The pharmaceutical composition of claim 24, wherein the solubilizing agent is sterile water.

26. The modified oncolytic virus of claim 1, wherein the oncolytic virus is a poxvirus.

27. The modified oncolytic virus of claim 26, wherein the poxvirus is a vaccina virus.

* * * * *

SEQUENCE LISTING

```
Sequence total quantity: 5
SEQ ID NO: 1             moltype = DNA   length = 969
FEATURE                  Location/Qualifiers
misc_feature             1..969
                         note = Description of Artificial Sequence:
                         Syntheticpolynucleotide
source                   1..969
                         mol_type = other DNA
                         organism = synthetic construct
SEQUENCE: 1
atgcattggg gaaccctgtg cggattcttg tggctttggc cctatctttt ctatgtccaa    60
gctgtgccca tccaaaaagt ccaagatgac accaaaaccc tcatcaagac aattgtcacc   120
aggatcaatg acatttcaca cacgcagtca gtctcctcca aacagaaagt caccggtttg   180
gacttcattc ctgggctcca ccccatcctg acctatccaa agatggacca gacactggca   240
gtctaccaac agatcctcac cagtatgcct tccagaaacg tgatccaaat atccaacgac   300
ctggagaacc tccgggatct tcttcacgtg ctggccttct ctaagagctg ccacttgccc   360
tgggccagtg gcctggagac cttggacagc ctggggggtg tcctggaagc ttcaggctac   420
tccacagagg tggtggccct gagcaggctg cagggggtctc tgcaggacat gctgtggcag   480
ctggacctca gccctgggtg cggaggtggc ggatccggcc gaggtggctc aggtggcggt   540
ggatcaggag gaggtggatc agctagcgca cctacttcaa gttctacaaa gaaaacacag   600
ctacaactgg agcatttact gctggattta cagatgattt tgaatggaat taataattac   660
aagaatccca aactcaccag gatgctcaca tttaagtttt acatgcccaa gaaggccaca   720
gaactgaaac atcttcagtg tctagaagaa gaactctcga ggaa agtgctaaat           780
ttagctcaaa gcaaaaactt tcacttaaga cccagggact taatcagcaa tatcaacgta   840
atagttctgg aactaaaggg atctgaaaca acattcatgt gtgaatatgc tgatgagaca   900
gcaaccattg tagaatttct gaacagatgg attacctttt gtcaaagcat catctcaaca   960
ctgacttga                                                            969

SEQ ID NO: 2             moltype = DNA   length = 1125
FEATURE                  Location/Qualifiers
misc_feature             1..1125
                         note = Description of Artificial Sequence:
                         Syntheticpolynucleotide
source                   1..1125
                         mol_type = other DNA
                         organism = synthetic construct
SEQUENCE: 2
atgctgtcca catctcgttc tcggtttatc agaaatacca acgagagcgg tgaagaagtc    60
accaccttt tgattatga ttcggtgct ccctgtcata aatttgacgt gaagcaaatt      120
ggggcccaac tcctgcctcc gctctactcg ctggtgttca tctttggttt tgtgggcaac   180
atgctggtcg tcctcatctt aataaactgc aaaaagctga agtgcttgac tgacatttac   240
ctgctcaacc tggccatctc tgatctgctt tttcttatta ctctcccatt gtgggctcac   300
tctgctgcaa atgagtgggt ctttgggaat gcaatgtgca attattcac agggctgtat    360
cacatcggtt atttttggcgg aatcttcttc atcatcctcc tgacaatcga tagataccctg  420
gctattgtcc atgctgtgtt tgctttaaaa gccaggacgg tcacctttgg ggtggtgaca   480
agtgtgatca cctggttggt ggctgtgttt gcttctgtcc caggaatcat ctttactaaa   540
tgccagaaag aagattctgt ttatgtctgt ggcccttatt ttccacgagg atggaataat   600
ttccacacaa taatgaggaa cattttgggg ctggtcctgc cgctgctcat catggtcatc   660
tgctactcgg gaatcctgaa aaccctgctt cggtgtcgaa acgagaagaa gaggcatagg   720
gcagtgagag tcatcttcac catcatgatt gtttactttc tcttctggac tcctataat    780
attgtcattc tcctgaacac cttccaggaa ttcttcggcc tgagtaactg tgaaagcacc   840
agtcaactgg accaagccac gcaggtgaca gagactcttg ggatgactca ctgctgcatc   900
aatcccatca tctatgcctt cgttggggag aagttcagaa gccttttttca catgctctt    960
ggctgtagga ttgccccact ccaaaaacca gtgtgtggag gtccaggagt gagaccagga  1020
aagaatgtga aagtgactac acaaggactc ctcgatggtc gtggaaaagg aaagtcaatt  1080
ggcagagccc tgaagccag tcttcaggac aaagaaggag cctag                    1125

SEQ ID NO: 3             moltype = DNA   length = 1125
FEATURE                  Location/Qualifiers
misc_feature             1..1125
                         note = Description of Artificial Sequence:
                         Syntheticpolynucleotide
source                   1..1125
                         mol_type = other DNA
                         organism = synthetic construct
SEQUENCE: 3
atgctgtcca catctcgttc tcggtttatc agaaatacca acgagagcgg tgaagaagtc    60
accaccttt tgattatga ttcggtgct ccctgtcata aatttgacgt gaagcaaatt      120
ggggcccaac tcctgcctcc gctctactcg ctggtgttca tctttggttt tgtgggcaac   180
atgctggtcg tcctcatctt aataaactgc aaaaagctga agtgcttgac tgacatttac   240
ctgctcaacc tggccatctc tgatctgctg ttccttatta ctctcccatt gtgggctcac   300
tctgctgcaa atgagtgggt ctttgggaat gcaatgtgca attattcac agggctgtat    360
cacatcggtt atttttggcgg aatcttcttc atcatcctcc tgacaatcga tagataccctg  420
gctattgtcc atgctgtgtt tgctttaaaa gccaggacgg tcacctttgg ggtggtgaca   480
agtgtgatca cctggttggt ggctgtgttt gcttctgtcc caggaatcat ctttactaaa   540
tgccagaaag aagattctgt ttatgtctgt ggcccttatt ttccacgagg atggaataat   600
ttccacacaa taatgaggaa cattttgggg ctggtcctgc cgctgctcat catggtcatc   660
tgctactcgg gaatcctgaa aaccctgctt cggtgtcgaa acgagaagaa gaggcatagg   720
```

```
gcagtgagag tcatcttcac catcatgatt gtttactttc tcttctggac tccctataat   780
attgtcattc tcctgaacac cttccaggaa ttcttcggcc tgagtaactg tgaaagcacc   840
agtcaactgg accaagccac gcaggtgaca gagactcttg ggatgactca ctgctgcatc   900
aatcccatca tctatgcctt cgttgggag aagttcagaa gccttttttca catagctctt   960
ggctgtagga ttgccccact ccaaaaacca gtgtgtggag gtccaggagt gagaccagga  1020
aagaatgtga aagtgactac acaaggactc ctcgatggtc gtggaaaagg aaagtcaatt  1080
ggcagagccc ctgaagccag tcttcaggac aaagaaggag cctag                 1125
```

| SEQ ID NO: 4 | moltype = DNA   length = 3444 |
|---|---|
| FEATURE | Location/Qualifiers |
| misc_feature | 1..3444 |
| | note = Description of Artificial Sequence: Syntheticpolynucleotide |
| source | 1..3444 |
| | mol_type = other DNA |
| | organism = synthetic construct |

```
SEQUENCE: 4
gtaggaatcg cagcgccagc ggttgcaagg cccaagaagc ccatcctggg aaggaaaatg    60
cattggggaa ccctgtgcgg attcttgtgg ctttggccct atctttttcta tgtccaagct   120
gtgcccatcc aaaaagtcca agatgacacc aaaaccctca tcaagacaat tgtcaccagg   180
atcaatgaca tttcacacac gcagtcagtc tcctccaaac agaaagtcac cggtttggac   240
ttcattcctg ggctccaccc catcctgacc ttatccagac tggaccagac actggcagtc   300
taccaacaga tcctcaccag tatgccttcc agaaacgtga tccaaatatc caacgacctg   360
gagaacctcc gggatcttct tcacgtgctg gccttctcta agagctgcca cttgccctgg   420
gccagtggcc tggagacctt ggacagcctg ggggtgtcc tggaagcttc aggctactcc   480
acagaggtgg tggccctgag caggctgcag gggtctctgc aggacatgct gtggcagctg   540
gacctcagcc ctgggtgctg aggcctttgaa ggtcactctt cctgcaagga ctacgttaag   600
ggaaggaact ctggcttcca ggtatctcca ggattgaaga gcattgcatg gacacccctt   660
atccaggact ctgtcaattt ccctgactcc tctaagccac tcttccaaag gcataagacc   720
ctaagcctcc ttttgcttga aaccaaagat atatacacag gatcctattc tcaccaggaa   780
gggggtccac ccagcaaaga gtgggctgca tctgggattc ccaccaaggt cttcagccat   840
caacaagagt tgtcttgtcc cctcttgacc catctccccc tcactgaatg cctcaatgtg   900
accagggtg atttcagaga gggcagaggg gtaggcagag cctttggatg accagaacaa   960
ggttccctct gagaattcca aggagttcca tgaagaccaa atccacacac gcagcaactc  1020
ccagcaacac aagctggaag cacatgttta tttattctgc attttattct ggatggattt  1080
gaagcaaagc accagcttct ccaggctctt tggggtcagc cagggccagg ggtctccctg  1140
gagtgcagtt tccaatccca tagatgggtc tggctgagct gaacccattt tgagtgactc  1200
gagggttggg ttcatctgag caagagctgg caaaggtggc tctccagtta gttctctcgt  1260
aactggtttc atttctactg tgactgatgt tacatccaag tgtttgcaat ggtgttgccc  1320
tgagtggatc tccaaggacc aggttatttt aaaaagattt gttttgtcaa gtgtcatatg  1380
taggtgtctg cacccagggg tggggaatgt ttgggcagaa gggagaagga tctagaatgt  1440
gttttctgaa taacatttgt gtggtgggtt ctttggaagg agtgagatca ttttcttatc  1500
ttctgcaatt gcttaggatg ttttttcatga aaatagctct ttcagggggg ttgtgaggcc  1560
tggccaggca cccctggag agaagtttct ggcctggct gaccccaaag agcctggaga  1620
agctgatgct ttgcttcaaa tccatccaga ataaaacgca aagggctgaa agccatttgt  1680
tggggcagtg gtaagctctg gctttctccg actgctaggg agtggtcttt cctatcatgg  1740
agtgacggtc ccacactggt gactgcgatc ttcagagcag ggtccttgg tgtgaccctc  1800
tgaatggtcc agggttgatc acactctggg tttattacat ggcagtgttc ctatttgggg  1860
cttgcatgcc aaattgtagt tctttgtctga ttggctcacc caagcaaggc caaaattacc  1920
aaaaatcttg ggggttttt actccagtgg tgaagaaaac tcctttagca ggtggtcctg  1980
agacctgaca agcactgcta ggcgagtgcc aggactccc aggccaggcc accaggatgg  2040
cccttcccac tggaggtcac attcaggaag atgaaagagg aggtttgggg tctgccacca  2100
tcctgctgct gtgttttttgc tatcacacag tgggtggtgg atctgtccaa ggaaacttga  2160
atcaaagcag ttaactttaa gactgagcac ctgcttcatg ctcagccctg actggtgcta  2220
taggctggag aagctcaccc aataaacatt aagattgagg cctgccctca gggatcttgc  2280
attcccagtg gtcaaaccgc actcacccat gtgccaaggt ggggtattta ccacagcagc  2340
tgaacagcca aatgcatggt gcagttgaca gcaggtggga aatggtatga gctgaggggg  2400
gccgtgccca ggggcccaca gggaaccctg cttgcacttt gtaacatgtt tacttttcag  2460
ggcatcttag cttctattat agccacatcc ctttgaaaca agataactga gaattttaaaa  2520
ataagaaaat acataagacc ataacagcca acaggtggca ggaccaggac tatagcccag  2580
gtcctctgat acccagagca ttacgtgagc caggtaatga gggactggaa ccagggagac  2640
cgagcgcttt ctgaaaaaga ggagtttcga ggtagagttt gaaggaggtg agggatgtga  2700
attgcctgca gagagaagcc tgttttgttg gaaggtttgg tgtgtggaga tgcagaggta  2760
aaagtgtgag cagtgagtta cagcgagagg cagagaacga gggcaaggc  2820
catgctgaag ggaccttgaa gggtaaagaa gtttgatatt aaaggagtta agagtagcaa  2880
gttctagaga agaggctggt gctgtggcca gggtgagagc tgctctggaa aatgtgaccc  2940
agatcctcac aaccacctaa tcaggctgag gtgtcttaag ccttttgctc acaaaacctg  3000
gcacaatggc taattcccag agtgtgaaac ttcctaagta taaatggttg tctgtttttg  3060
taacttaaaa aaaaaaaaaa aagtttggcc gggtgcggtg gctcacgcct gtaatcccag  3120
cactttggga ggccaaggtg gggggatcac aaggtcacta gatggcgagc atcctgggca  3180
acatggtgaa accccgtctc tactaaaaac acaaaagtta gctgagcgtg gtggcgggcg  3240
cctgtagtcc cagccactcg ggaggctgag acaggagaat cgcttaaacc tgggaggcgg  3300
agagtacagt gagccaagat cgcgccactg cactccggcc tgatgacaga gcgagattcc  3360
gtcttaaaaa aaaaaaaaaa aagtttgtt tttaaaaaaa tctaaataaa ataactttgc  3420
cccctgcaaa aaaaaaaaaa aaaa                                        3444
```

| SEQ ID NO: 5 | moltype = DNA   length = 418 |
|---|---|
| FEATURE | Location/Qualifiers |
| misc_feature | 1..418 |

```
                note = Description of Artificial Sequence:
                      Syntheticpolynucleotide
source          1..418
                mol_type = other DNA
                organism = synthetic construct
SEQUENCE: 5
aattctatgg ctccgacttc aagttctacc aagaagaccc agcttcaatt agaacattta    60
cttctagatt tacaaatgat tctgaatggt atcaacaatt ataagaatcc aaagcttact   120
cgtatgttga cctttaaatt ctatatgcct aagaaggcta ctgaattaaa acacctgcag   180
tgtttagaag aagagctcaa accgttagaa gaagttctga atctggctca atctaaaaac   240
ttccatttac gtccacgaga tcttatctct aatattaacg taatcgtttt ggaacttaaa   300
ggatccgaaa ctaccttcat gtgtgaatat gctgacgaaa ccgctacgat cgtagaattt   360
cttaatcgat ggattacttt ctgtcaatct attatctcta ccttaacttg agtcgacg    418
```